(12) United States Patent
Shraibom et al.

(10) Patent No.: US 11,344,598 B2
(45) Date of Patent: May 31, 2022

(54) HERBAL NANOFORMULATIONS FOR TREATING PSORIASIS AND OTHER SKIN CONDITIONS

(71) Applicant: Sirbal Ltd., Limassol (CY)

(72) Inventors: Nadav Shraibom, Herzelia (IL); Eran Steinberg, San Francisco, CA (US); Manu Jaggi, DLF (IN); Anu T. Singh, Noida (IN); Ritu Verma, Ghaziabad (IN); Alka Madaan, Ghaziabad (IN)

(73) Assignee: Sirbal Limited, Limassol (CY)

( * ) Notice: Subject to any disclaimer, the term of this patent is extended or adjusted under 35 U.S.C. 154(b) by 788 days.

(21) Appl. No.: 16/301,732

(22) PCT Filed: Mar. 27, 2017

(86) PCT No.: PCT/US2017/024378
§ 371 (c)(1),
(2) Date: Nov. 15, 2018

(87) PCT Pub. No.: WO2017/172648
PCT Pub. Date: Oct. 5, 2017

(65) Prior Publication Data
US 2019/0321430 A1    Oct. 24, 2019

Related U.S. Application Data

(60) Provisional application No. 62/325,993, filed on Apr. 21, 2016, provisional application No. 62/313,709, filed on Mar. 26, 2016.

(51) Int. Cl.
| | | |
|---|---|---|
| *A61K 36/355* | (2006.01) | |
| *A61K 8/9789* | (2017.01) | |
| *A61P 17/06* | (2006.01) | |
| *A61K 8/04* | (2006.01) | |
| *A61K 8/81* | (2006.01) | |
| *A61K 36/708* | (2006.01) | |
| *A61K 36/804* | (2006.01) | |
| *A61K 47/10* | (2017.01) | |
| *A61K 47/22* | (2006.01) | |
| *A61K 47/32* | (2006.01) | |
| *A61K 47/36* | (2006.01) | |
| *A61Q 19/00* | (2006.01) | |

(52) U.S. Cl.
CPC ............ *A61K 36/355* (2013.01); *A61K 8/042* (2013.01); *A61K 8/8147* (2013.01); *A61K 8/9789* (2017.08); *A61K 36/708* (2013.01); *A61K 36/804* (2013.01); *A61K 47/10* (2013.01); *A61K 47/22* (2013.01); *A61K 47/32* (2013.01); *A61K 47/36* (2013.01); *A61P 17/06* (2018.01); *A61Q 19/00* (2013.01); *A61K 2800/5922* (2013.01); *A61K 2800/92* (2013.01)

(58) Field of Classification Search
None
See application file for complete search history.

(56) References Cited

U.S. PATENT DOCUMENTS

| | | |
|---|---|---|
| 8,597,695 B1 | 12/2013 | Shraibom |
| 8,734,859 B1 | 5/2014 | Shraibom |
| 2003/0108501 A1 | 6/2003 | Hofrichter et al. |
| 2007/0202069 A1 | 8/2007 | Tamareselvy et al. |
| 2007/0275021 A1 | 11/2007 | Lee et al. |
| 2008/0145883 A1 | 6/2008 | Baumruker et al. |
| 2009/0123564 A1 | 5/2009 | Jain et al. |
| 2009/0234153 A1 | 9/2009 | Aoki et al. |
| 2014/0205685 A1 | 7/2014 | Shraibom |
| 2016/0184381 A1 | 6/2016 | Shraibom |

FOREIGN PATENT DOCUMENTS

| | | |
|---|---|---|
| CN | 104667070 A | 6/2005 |
| WO | 2008/069604 A1 | 6/2008 |
| WO | 2015/082950 A1 | 6/2015 |
| WO | 2017/172648 A1 | 10/2017 |

OTHER PUBLICATIONS

PCT Notification of Transmittal or Search Report and Written Opinion of the ISA, or the Declaration, for PCT Application No. PCT/US17/24378, dated Aug. 14, 2017, 23 Pages.
PCT Notification of Transmittal of International Preliminary Report on Patentability Chapter I, and International Preliminary Report on Patentability Chapter I, for PCT Application No. PCT/US17/24378, dated Oct. 2, 2018, 15 pages.
Machine-Translation of Chinese published application CN 104667070 A; Publication date: Jun. 3, 2005; for: A medicine for treating skin diseases and a preparation method thereof, 5 pages.

*Primary Examiner* — Michael Barker
(74) *Attorney, Agent, or Firm* — SF Bay Area Patents, LLC; Andrew V. Smith

(57) ABSTRACT

A medicinal composition includes an active herbal component that is prepared by cooking a combination of Sheng Di Huang, Da Huang and Jin Yin Hua and has an average particulate size between 100-300 nm. Example formulations include topical gels, tablets and capsules.

20 Claims, 43 Drawing Sheets

Results

| | Diam.(nm) | % Intensity | Width(nm) |
|---|---|---|---|
| Z-Average (d.mm): 320.6 mm  Peak 1: | 270.2 | 100.0 | 27.83 |
| Pdl: 0.204  Peak 2: | 0.000 | 0.0 | 0.000 |
| Intercept: 0.954  Peak 3: | 0.000 | 0.0 | 0.000 |

| | Diam.(nm) | % Intensity | Width(nm) |
|---|---|---|---|
| Z-Average (d.mm): 258.7 mm  Peak 1: | 472.1 | 100.0 | 47.85 |
| Pdl: 0.298  Peak 2: | 0.000 | 0.0 | 0.000 |
| Intercept: 0.864  Peak 3: | 0.000 | 0.0 | 0.000 |

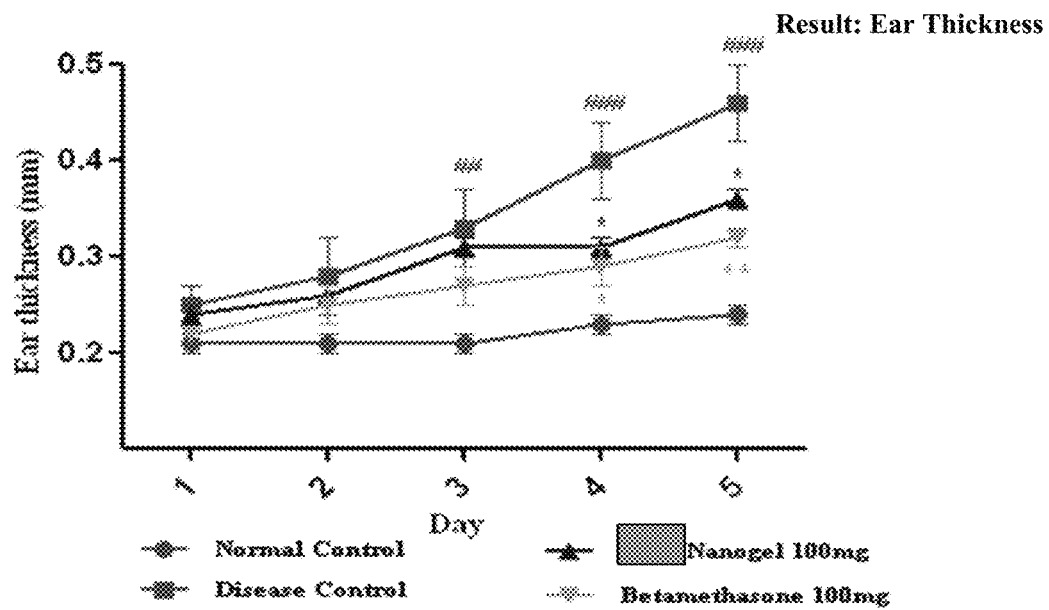

:p<0.01,###:p<0.001; Two way ANOVA followed by Bonferroni's test Vs Normal control
*:p<0.05,**:p<0.01; Two way ANOVA followed by Bonferroni's Vs Disease control
• 3HX Nanogel : 21.6% Reduction seen in ear thickness
• Betamethasone (0.1% w/w) : 30.9% Reduction in ear thickness

Figure 27

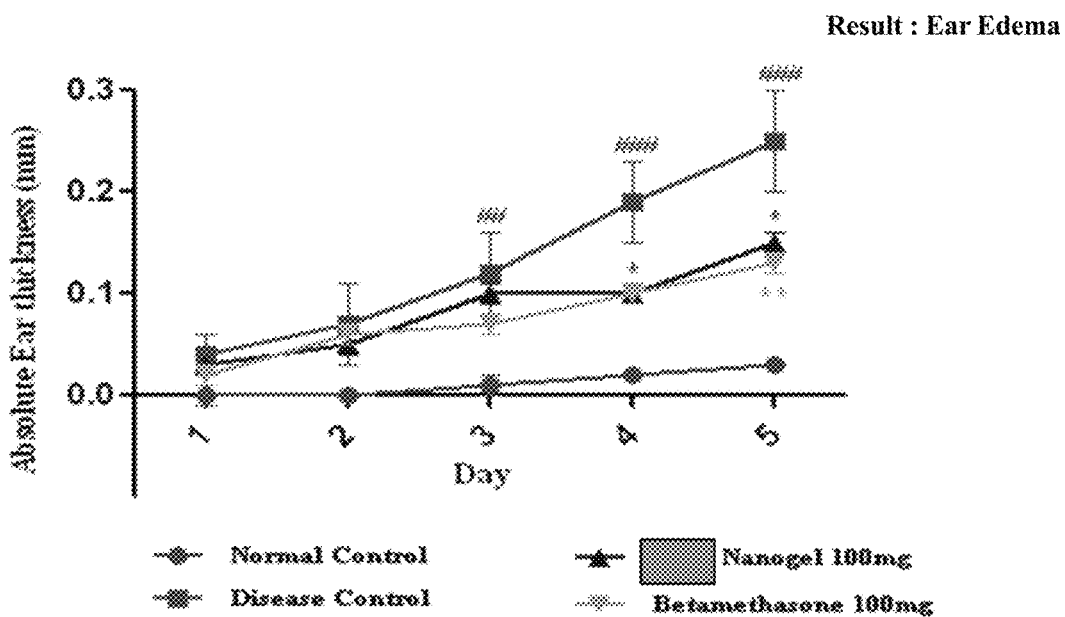

:p<0.01,###:p<0.001; Two way ANOVA followed by Bonferrni's test Vs Normal Control
*:p<0.05,**:p<0.01; Two way ANOVA followed by Bonferrni's Vs Disease control
• 3HX Nanogel : 40.1% Reduction seen edema caused by inflammation
• Betamethasone (0.1% w/w) : 49.6% Reduction in ear edema

Figure 28

:p<0.0; One way ANOVA followed by Dunnett's test Vs Normal control
*:p<0.05; One way ANOVA followed by Dunnett's test Vs Disease control
• 3HX Nanogel : 37.5% Reduction in biopsy weight
• Betamethasone (0.1% w/w) : 26.1% Reduction

Experimental findings : Ear Edema

| Treatment | Day-1 | Day-2 | Day-3 | Day-4 | Day-5 | Day-6 | Day-7 | Day-8 | Day-9 | Day-10 |
|---|---|---|---|---|---|---|---|---|---|---|
| G1; Normal Control | 0.00 | 0.00 | 0.00 | 0.01 | 0.00 | 0.00 | 0.00 | 0.00 | 0.01 | 0.00 |
| G2; Disease Control | 0.054 | 0.072 | 0.094 | 0.124 | 0.165 | 0.168 | 0.168 | 0.178 | 0.170 | 0.182 |
| G3, 3 HX NANOGEL ,b.i.d | 0.051 | 0.067 | 0.079 | 0.078 | 0.085 | 0.085* | 0.102 | 0.100 | 0.109 | 0.111 |
| G4, 3 HX Cream ,b.i.d | 0.041 | 0.062 | 0.079 | 0.096 | 0.105 | 0.109 | 0.116 | 0.112 | 0.120 | 0.108 |
| G5, TPA + 0.1% Betamethasone | 0.008 | 0.019 | 0.022 | 0.041 | 0.047 | 0.053 | 0.079 | 0.078 | 0.066 | 0.066 |

*p<0.05

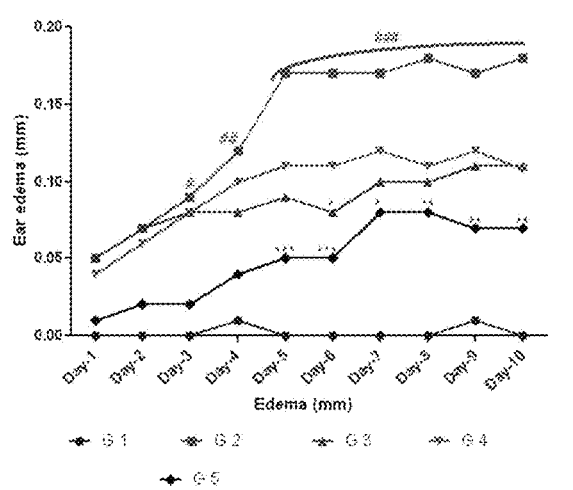

- Two way ANOVA followed by Bonferrni posthoc multiple comparison test
- ### denotes the statistical significance in comparison to G1 group
- ***denotes the statistical significance in comparison to G2 group
- Treatment group (G4; 3HX-NanoGel) showed significant reduction in ear edema

Figure 32

Experimental findings : % Inhibition of ear edema

| Treatment | Day-1 | Day-2 | Day-3 | Day-4 | Day-5 | Day-6 | Day-7 | Day-8 | Day-9 | Day-10 |
|---|---|---|---|---|---|---|---|---|---|---|
| G1; Normal Control | NA | NA | NA | NA | NA | NA | NA | NA | NA | NA |
| G2; Disease Control | 0.00 | 0.00 | 0.00 | 0.00 | 0.00 | 0.00 | 0.00 | 0.00 | 0.00 | 0.00 |
| G3, 3 HX NANOGEL ,b.i.d | 5.43 | 7.51 | 16.37 | 37.88 | 48.61 | 48.80 | 39.36 | 43.43 | 36.83 | 38.76 |
| G4, 3 HX Cream ,b.i.d | 23.26 | 13.87 | 16.37 | 22.82 | 36.52 | 35.07 | 31.19 | 37.09 | 29.17 | 40.83 |
| G5, TPA + 0.1% Betamethasone | 86.05 | 73.41 | 76.55 | 67.11 | 71.79 | 68.66 | 52.97 | 56.10 | 61.27 | 63.53 |

✓ Compared to G4 (3-HX Cream); G3 (3-HX Nanogel) shows good inhibitory activity

Experimental findings : Ear punch biopsy

| | G1; Normal Control | G2; Disease control | G3, 3 HX NANOGEL, b.i.d | G4, 3 HX Cream, b.i.d | G5, TPA + 0.1% Betamethasone |
|---|---|---|---|---|---|
| Mean | 2.88 | 6.25 | 4.50 | 4.50 | 3.25 |
| SD | 0.64 | 0.89 | 0.53 | 0.93 | 0.71 |
| SEM | 0.23 | 0.31 | 0.19 | 0.33 | 0.25 |

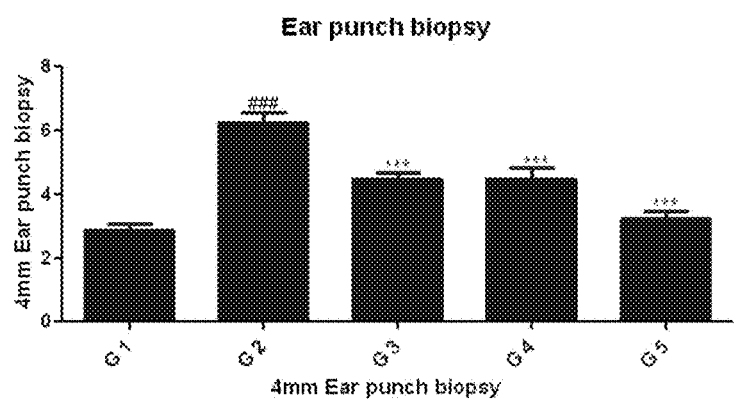

- One way ANOVA followed by Dunnett's multiple comparison test
- ### denotes the statistical significance in comparison to G1 group
- ***denotes the statistical significance in comparison to G2 group
- All the treatment group showed significant reduction in ear punch biopsy weight

Figure 34

HERBAL NANOFORMULATIONS FOR TREATING PSORIASIS AND OTHER SKIN CONDITIONS

PRIORITY AND RELATED APPLICATIONS

This application is a 371 of PCT/US17/24378, filed Mar. 27, 2017; which claims priority to U.S. provisional patent application Ser. Nos. 62/313,709, filed Mar. 26, 2016, and U.S. Ser. No. 62/325,993, filed Apr. 21, 2016; which are each incorporated by reference.

This application is related to U.S. patent application Ser. Nos. 14/981,899, 14/946,724, 14/872,138, 14/815,892, 14/815,705, 14/754,266, 13/900,525, 13/361,978, 13/900,525, 13/900,526, 14/144,928, 14/144,931, 14/710,836, 14/710,865, 14/737,485, 14/751,664, 14/752,344, 14/752,539, 62/268,226, 62/259,056, 62/297,796, and 62/198,637; and U.S. Pat. Nos. 9,066,974, 9,095,606, 8,541,382; 8,597,695; and 8,734,859. Each of these related patents and patent applications is incorporated by reference.

BACKGROUND OF THE INVENTION

1. Field of the Invention

The present invention relates generally to disease treatments, including treatments for psoriasis, eczema, melanoma and other skin disorders, inflammatory and autoimmune ailments and cancer. More specifically it concerns the use of combinations of certain herbs, certain herbal extracts and/or certain herbal molecular components alone or in combination with known antimetabolite, antifolate, anti-inflammatory, or autoimmune treatments and other known and/or described treatments, particularly to treat psoriasis or reduce psoriatic suffering and symptoms, or to treat eczema or blisters, redness or eczematic soreness or itching or crusty skin caused by eczema, or to treat inflammation or an inflammatory condition, or to treat melanoma or other cancer, or to reduce white cell count, tumor size or painfulness from cancer, or to treat or reduce suffering from another skin ailment, or to treat an autoimmune disease or disorder, or otherwise to treat or to reduce suffering from one or more of diseases causing or stemming from inflammation or autoimmune disease or to administer along with a known or discovered treatment to enhance effectiveness, reduce toxicity or side effects and/or to facilitate weening from a known or discovered treatment. Examples include herbal formulas including one or more of, or a combination of two or more of, Da Huang, Sheng Di Huang, and Jin Yin Hua, and/or combinations including one or more of Mu Dan Pi, Di Gu Pi, Xian He Cao, and/or Chun Gen Pi., and/or another herb, molecule or extract, or combination of herbs, molecules or extracts described herein.

2. Description of the Related Art

Herbal medicines are prevalent, and serve the medicinal needs of a large population around the world. The global herbal medicine market is currently worth around $30 billion. There is also an increased effort for the isolation of bioactive phytochemicals from herbs for their possible usefulness in the control of various ailments.

Approximately ⅓ of persons having a psoriasis condition suffer from head or scalp psoriasis. Often, it is not detected because it is not visible underneath the hair of the person who is suffering with psoriasis. Sometimes, head or scalp psoriasis is confused with dandruff or other head or scalp conditions that are sometimes deemed to be treatable with ordinary shampoos and conditions.

There exist treatments for psoriatic and eczematic scalp conditions which are steroid-based. Steroid-based treatments are sometimes effective, but can also sometimes have serious negative short-term or long-term side effects. Clobex shampoo (0.05%), by Galderma Labs USA, is an example of a steroid, specifically a corticosteroid, based shampoo that was approved by FDA for treatment of scalp psoriasis. CLOBEX® (clobetasol propionate) Shampoo, 0.05%, contains clobetasol propionate, a synthetic fluorinated corticosteroid, for topical dermatologic use. The corticosteroids constitute a class of primarily synthetic steroids used topically as anti-inflammatory and antipruritic agents. Clobetasol propionate is a white to practically white crystalline, odorless powder insoluble in water. While Clobex shampoo has been shown to be effectiveness in treating scalp psoriasis in a significant percentage of test subjects, a large percentage of test subjects were also subjected to serious negative side effects. It is desired to have an effective and safe, non-steroidal medicinal formulation for treating psoriatic and eczematic scalp conditions.

It is also desired to have such a safe and effective medicinal formulation that may be a useful component in a treatment regimen for patients suffering with or without a diagnosis from one or more other inflammatory, autoimmune, oncological and/or dermatological conditions.

It is desired to provide a safe and effective herbal formulation that exhibits advantageously high percentage of cumulative active component release.

It is also desired to provide a safe and effective herbal formulation that exhibits advantageously high permeability, particularly into dermal layers.

It is desired to provide a safe and effective herbal formulation that exhibits advantageous extrudability.

It is desired to provide a safe and effective herbal formulation that exhibits advantageous spreadability.

It is desired to provide a safe and effective herbal formulation that exhibits advantageous viscosity.

It is desired to provide a safe and effective herbal formulation that exhibits advantageous adhesiveness.

It is desired to provide a safe and effective herbal formulation that exhibits advantageous bioavailability, particularly in a tablet, capsule or other oral formulation, and also in a topical, sub-dermal or IV formulation.

It is desired to provide more reliable, efficient medical kits that include diagnostic test kits and safe and effective medicines for treating a patient in accordance with an indication provided by the test kit.

It is desired to provide more reliable prognostic kits that include efficient medicinal formulations and prognostic measuring devices and prognostic indicators.

It is also desired to provide prognostic test kits configured to measure levels of certain panels of one or more prognostic markers that are most indicative of a patient's tendency to respond safely and effectively to certain treatments or combinations of treatments that are efficiently formulated, particularly for psoriatic, eczematic and other inflammatory skin conditions, and for certain autoimmune, oncological, dermatological and/or inflammatory diseases, conditions, disorders or complications.

It is also desired to have an herbal and/or molecular combination that is efficiently formulated for administering to a patient as a safe and effective treatment of a condition.

It is also desired to have an herbal and/or molecular combination that is efficiently formulated for administering to a patient before, during and/or after a typical, known or discovered treatment regimen to enhance the effectiveness of such known or discovered treatments, and/or to reduce side effects of such known or discovered treatments and/or for weening a patient from a dependence on such known or discovered treatments.

BRIEF DESCRIPTION OF THE DRAWINGS

FIG. 2A: Zero order; Fraction DR and Time, y=0.0311x+0.188 and $R^2$=0.8951
FIG. 2B: First order, Log % D Remaining to Time, y=−0.0346x+1.9442 and $R^2$=0.9666
FIG. 2C: Higuchi Matrix, Fraction DR to Square root of time, y=0.1748x+0.0203 and $R^2$=0.9827
FIG. 2D: Peppas Korsemeyer, log fraction drug release to log time, y=0.5514x−0.7773 and $R^2$=0.9561
FIG. 2E: Hixon Crowell, $(Mo)^{1/3}-(Mt)^{1/3}$ to Time, y=0.0176x+3.6965 and $R^2$=0.9703
FIG. 4A: n Shear Rate y, [Herschel-Bulkley I] tau0=51.728 Pa; b=41.86; p=0.44812; n Viscosity
FIG. 4B: t to Shear Rate y; d=0.1 mm; T Shear Stress; [Herschel-Bulkley I]; Tau0=51.728 Pa; b=41.86; p=0.44812; t Shear Stress
FIG. 4C: n to Time t; d=0.1 mm; n Viscosity
FIG. 11A: Dissolution Profile Batch 1
FIG. 11B: Dissolution Profile Batch 2
FIG. 11C: Dissolution Profile Batch 3
FIG. 11D: Dissolution Profile Batch 4
FIG. 11E: Dissolution Profile Batch 5
FIG. 11F: Dissolution Profile Batch 6
FIG. 13A: Higuchi Matrix, Fraction DR to Square root of time, y=0.9142x−0.347 and $R^2$=0.9572
FIG. 13B: Zero order, Fraction DR to Time, y=0.4576x+0.0657 and $R^2$=0.9069
FIG. 13C: First order, Log % D Remaining to Time, y=−0.5316x+2.1083 and $R^2$=0.9805
FIG. 13D: Peppas Korsemeyer, log fraction drug release to log time, y=1.0834x−0.2819 and $R^2$=0.9536
FIG. 13E: Hixon Crowell, $(Mo)-1/3-(Mt)-1/3$ to Time, y=0.1282x+3.7142 and $R^2$=0.3718
FIG. 17A: Zero order
FIG. 17B: First order
FIG. 17C: Higuchi Matrix
FIG. 17D: Peppas Korsemeyer
FIG. 17E: Hixon Crowell
FIG. 18A
FIG. 18B
FIG. 18C
FIG. 19A: Evaluation of the example formulation (F3)
FIG. 27 includes plots of ear thickness for 100 mg 3HX nanogel and betamethasone formulations in accordance with certain embodiments.
FIG. 28 includes plots of ear edema for 100 mg 3HX nanogel and betamethasone formulations in accordance with certain embodiments.
FIG. 32 includes plots of ear edema for 3HX nanogel, 3HX cream and betamethasone formulations in accordance with certain embodiments.
FIG. 34 is a graph showing ear punch biopsy weights for 3HX nanogel, 3HX cream and betamethasone formulations in accordance with certain embodiments.

BRIEF DESCRIPTION OF THE TABLES

Figure 1:
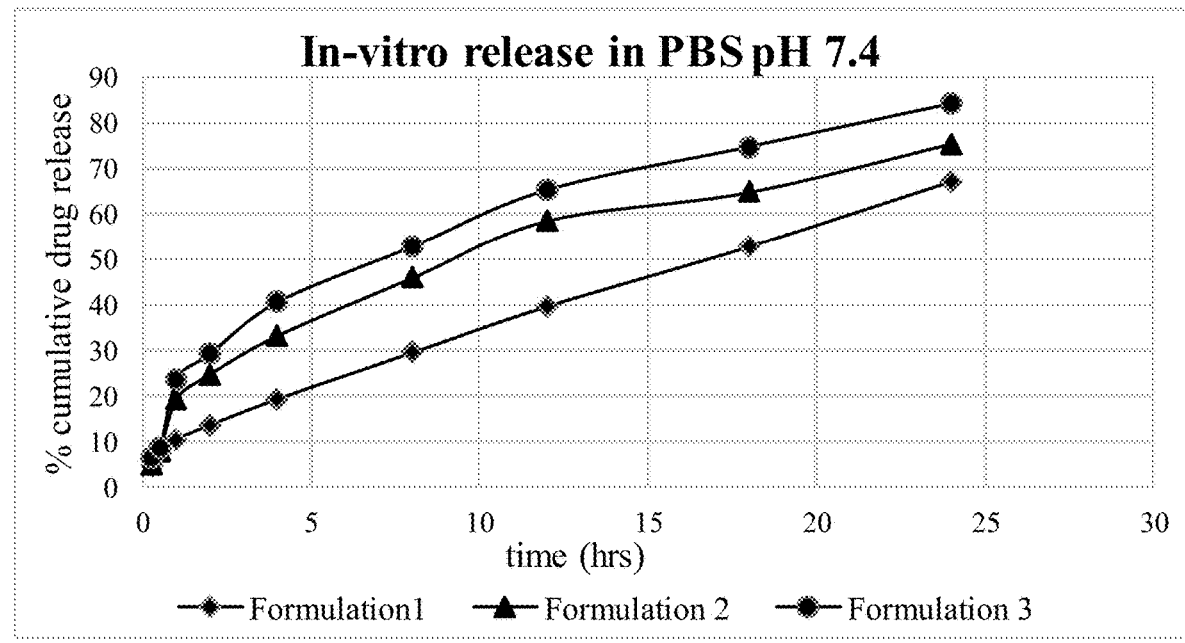
FIG. 1: In vitro release profile of example topical gels

Table 1A: Composition of example topical gel
Table 1B: T.A Settings
Table 2: Characterization of different example formulations
Table 3: pH and % drug content of different formulations (n=3)

Table 4: In vitro release model fitting in terms of linear regression coefficient (R2) values corresponding to FIGS. 2A-2E.

Table 5: Texture profile of the example formulation F3 corresponding to FIG. 6.

Table 6: Tablet Preparation, Ingredients of tablets and capsule

Table 7: Organoleptic Evaluation

Table 8: In vitro Release Studies, Equation for Peppas Model and Peppas Model

Table 9: Preparation of Topical formulation gel

Table 10: Results: Physical parameters of the prepared gels

Table 11: Topical Preparation (gel); pH and % drug content of the formulations:

Table 12: Preparation of Topical formulation gel

Table 13: In-vitro drug release study (Time (hrs) and % Cumulative release)

Table 14: In-vitro drug release study (Time (hrs) and % Cumulative release)

Table 15: Evaluation of the example formulation (F3); T.A Settings

Table 16: Evaluation of the example formulation (F3); Texture analysis

Table 17: Drug Loading Studies

Table 18: Organoleptic evaluation

DETAILED DESCRIPTIONS OF THE EMBODIMENTS

Psoriasis is a common T-cell-mediated immune disorder characterized by circumscribed, red, thickened plaques with an overlying silver-white scale. Psoriasis is regarded as an autoimmune disease in which genetic and environmental factors have a significant role. The name of the disease is derived from Greek word 'psora' which means itch. Psoriasis is a non-contagious, dry, inflammatory and ugly skin disorder, which can involve entire system of person. It is mostly inherited and mainly characterized by sharply marginated scaly, erythematous plaques that develop in a relatively symmetrical distribution. The most commonly affected sites are the scalp, tips of fingers and toes, palms, soles, umbilicus, gluteus, under the breasts and genitals, elbows, knees, shins and sacrum.

Gel as semisolid, being either suspensions of small inorganic particles or large organic molecules interpenetrated with liquid. A gel is a semisolid system of at least two interpenetrating phases: a gelling agent and a liquid. Gels that contain water are called hydrogels, while those that contain an organic liquid are called organogels. Hydrogels, in the broad sense, include the matrix of water-soluble materials such as cellulose derivatives and natural gums.

2. Materials and Methods 2.1. Materials

Drug 3HX was provided by Dabur research foundation.

2.2. Example Preparation of Nanogel

Gels were prepared by cold mechanical method. A polymer (Carbopol Ultraze 21) was weighed and it was sprinkled slowly on the surface of purified water with continuous stirring for 2 hr. After which it was stirred continuously by mechanical stirrer, till polymer soaked in the water. Now Propylene glycol and Polyethylene glycol 400 (PEG 400), which behaves as penetration enhancers and DMDM Hydantoin as preservative was added to the gel, followed by menthol and isopropyl alcohol. Now the drug "3HX" in the studied example embodiment described herein includes 100 wt. % of a combination of Da Huang, Sheng Di Huang and Jin Yin Hua. In certain embodiments, an herbal nanoformulation may include between 57 wt. %-100 wt. % of a combination of Da Huang, Sheng Di Huang and Jin Yin Hua. The nanoformulations may be formulated with smaller than 500 nm particulate sizes, or smaller than 400 nm, or smaller than 300 nm, or smaller than 200 nm, or smaller than 100 nm, or less. Further embodiments include the two herb combinations of Da Huang and Sheng Di Huang, Da Huang and Jin Yin Hua, and Sheng Di Huang and Jin Yin Hua, and a single herb combination may include Da Huang, Sheng Di Huang or Jin Yin Hua, and combinations with one or two or more other herbs or other active treatments or ingredients, including those described in the patents and patent applications referenced above.

In the studied example embodiment, 3HX was added to the gel with continuous stirring till drug get dispersed in gel completely. Finally with continuous stirring, triethanolamine was added to neutralize the gel and it maintains the pH of the gel.

TABLE 1A

Composition of example topical gel

| Ingredients | F1 | F2 | F3 |
|---|---|---|---|
| Drug (3HX) (gm) | 2.5 | 2.5 | 2.5 |
| Carbopol Ultraze 21 (% w/v) | 2 | 2 | 2 |
| Polyethylene glycol 400 (PEG 400) (% v/v) | 5 | 5 | 10 |
| Propylene glycol (% v/v) | — | 5 | 10 |
| Menthol (% w/v) | 0.05 | 0.05 | 0.05 |
| Isopropyl alcohol (% v/v) | 0.1 | 0.1 | 0.1 |
| DMDM Hydantoin (% v/v) | 0.075 | 0.075 | 0.075 |
| Triethanolamine | q.s | q.s | q.s |
| Distilled water (ml) | 100 | 100 | 100 |

2.3. Characterization of Nanogel

All the prepared formulations were evaluated for various parameters.

2.3.1. Colour

The color and appearance of the gel formulations F1, F2 and F3 were visually analyzed.

2.3.2. Consistency

It was determined manually by applying on the skin.

2.3.3. Homogeneity

All the developed were tested for homogeneity by visual inspection. They were tested for the presence of any aggregates or lumps.

2.3.4. Grittiness

The formulated gels i.e F1, F2 and F3 were evaluated for the presence of any gritty particles by applying it on the skin.

2.3.5. Phase Separation

The formulated gels F1, F2 and F3 were observed for any phase separation by visual observation for 1 week.

2.3.6. pH Determination

The pH of the prepared gel was determined using a digital pH meter at room temperature. Accurately weighed 2.5 gm of gel was weighed and dispersed in 25 ml of distilled water and then pH meter was dipped in the dispersion. The measurement of pH of the formulated gel was done in triplicate and average values were calculated.

2.3.7. Drug Content Determination 1 gm of gel was dissolved in 50 ml of distilled water. Drug content was determined at 280 nm using UV-visible spectrophotometer and was calculated using the equation obtained by linear regression analysis of calibration curve.

2.3.8. In Vitro Drug Release Study by Artificial Membrane

The cellophane membrane was cut to size and washed with distilled water for 1. Finally, it was soaked in pH 7.4 phosphate buffer saline for 24 h. Diffusion studies were carried out by using Franz type diffusion cell for formulation F1, F2 and F3 in pH 7.4 phosphate buffer solution. 500 mg of gel (F1) was placed on the cellophane membrane which was then mounted on the Franz diffusion cell. The receptor medium with the pH 7.4 phosphate buffer was maintained at constant temperature of 37° C. The medium was stirred continuously on a magnetic stirrer at 100 rpm. 2 ml of aliquots were withdrawn at present time intervals and replaced by an equal volume of fresh dissolution medium. The samples were then analyzed for using UV-visible method spectrophotometry.

On the basis of in vitro drug release study the formulation having the best release was selected. The amount of the drug released was incorporated into various release kinetic models as Zero order model, first-order model, Higuchi model, Hixcon-Crowell model and Korsmeyer—Peppas model, among them the best fit model was determined on the basis of regression co-efficient ($R^2$) value.

Drug Release Kinetic Study

To analyze the mechanism of drug release from the topical gel, the release data were fitted to the following equations:

Zero—Order Equation:

$$Q = k_o t$$

Where Q is the amount of drug released at time t, and $k_0$ is the zero—order release rate.

First—Order Equation:

$$ln(100-Q) = ln\ 100 - k_1 t$$

Where Q is the percent of drug release at time t, and $k_1$ is the first—order release rate constant.

Higuchi's Equation:

$$Q = k_2 \sqrt{t}$$

Where Q is the percent of drug release at time t, and $k_2$ is the diffusion rate constant.

2.3.9. Permeation Studies Using Rat Skin

The abdominal skin of full thickness was excised from the rat free from any visible sign of disease. The skin was mounted in the donor compartment of Franz diffusion cell. The example gel formulation (F3) was placed over it and permeation studies were carried out. The receptor medium with pH 7.4 phosphate buffer was maintained at constant temperature of 37° C. with a constant stirring of 100 rpm for 24 hr. Then aliquot of about 2 ml was taken at different time interval which was replaced by fresh solvent. The analysis was done using UV spectrophotometry at 280 nm.

2.4. Evaluation of Example Nanogel (F3)

2.4.1. Determination of Viscosity

The viscosity of the example formulation (F3) was measured using rheometer (MCR 101. Rheoplus, Anton Paar India Pvt. Ltd., India). It was done by using cone plate probe and carried out for 6 seconds.

2.4.2. Determination of Extrudability

It is test to measure the force to extrude the gel from the tube. On application of weight, the amount of gel extruded from the aluminium tube was determined. The gel extruded should be at least 0.5 cm ribbon in 10 s. More quantity of gel extruded better is extrudability. The extrudability of the example formulation was measured in triplicate.

2.4.3. Spreadability Analysis by Using Texture Analyzer

Spreadability of the gel was determined by using TA.XT2 texture analyzer (Stable Micro Systems, Goldalming, UK). The Spreadability test was performed using Spreadability rig coding HDP/SR. Data acquisition and mathematical was done using Texture Expert® software. Spreadability value was determined for the example formulation (F3).

TABLE 1B

| T.A Settings | |
|---|---|
| Test Mode | Compression |
| Test speed | 3.0 mm/s |
| Post test speed | 10.0 mm/s |
| Target Mode | Distance |
| Distance | 23 mm |
| Trigger type | Button |
| Break Mode | Off |
| Stop Plot At | Start position |
| Tare mode | Auto |

2.4.4. Texture Analysis by Using Texture Analyzer (Tensile Strength Measurement)

Tensile strength of the gel was determined by using TA.XT2 texture analyzer (Stable Micro Systems, Goldalming, UK). The mechanical properties have been assessed using the texture analyzer with a load of 5 kg loaded cell. Data acquisition and mathematical was done using Texture Expert® software. Cohesiveness, firmness and consistency were determined for the example formulation (F3).

2.4.5. Bio-Adhesive Strength Measurement

Bio-adhesion measurement was done by means of a tensile test, which indicates the gel bio-adhesive potential. The maximum force for detaching a piece of skin from gel, after an initial period of the contact was determined. The forces involved in the process were measured by texture analyzer. Average maximum positive force (adhesiveness) was determined for the example gel formulation (F3). Sample was placed on the blank plate of Heavy Duty Plate. A holed plate is then placed on top of the sample, central to the probe, allowing passage. This plate provides weight around the test region to prevent lifting of the sample when the probe is withdrawn, hence avoiding stickiness. The adhesive test is then commenced. The probe should be cleaned between the tests.

3. Results and Discussion

3.1. Characterization of Nanogel

TABLE 2

Characterization of different example formulations

| Parameters | F1 | F2 | F3 |
|---|---|---|---|
| Color & appearance | Brownish color | Brownish color | Brownish color |
| Homogeneity | Good | Good | Good |
| Phase Separation | No | No | No |
| Grittiness | No | No | No |

3.2. pH and % Drug Content Determination

TABLE 3 pH and % drug content of different formulations (n = 3)

| Formulation | pH | % Drug content |
|---|---|---|
| F1 | 6.7 ± 0.09 | 98.4 ± 0.5 |
| F2 | 6.82 ± 0.04 | 98.9 ± 0.2 |
| F3 | 6.89 ± 0.20 | 99.3 ± 0.4 |

3.3. In Vitro Drug Release Study by Artificial Membrane

The drug release behavior of gel formulation F1, F2 and F3 was investigated using a cellophane membrane in pH 7.4 PBS (37±0.5° C.). In FIG. 1 F1, F2 and F3 showed cumulative % drug release of 75.54 and 84.23 respectively. On the basis of in-vitro drug release study, the release profile of F3 was found to be best among these three.

FIG. 1: In vitro release profile of example topical gels

The amount of the drug released was incorporated into various release kinetic models as Zero order model, first-order model, Higuchi model, Hixcon-Crowell model and Korsmeyer—Peppas model, among them the best fit model was determined on the basis of regression co-efficient ($R^2$) value. The observed best fit model was Higuchi model followed by First order release model with $R^2$ 0. 9827 and 0.9666 respectively. Therefore, for the further evaluation formulation F3 was selected. These various kinetic models are given in FIG. 2 and $R^2$ values for all the models are presented in the Table 4.

FIGS. 2A-2E: In vitro release profile of topical gel

Figure 2A:
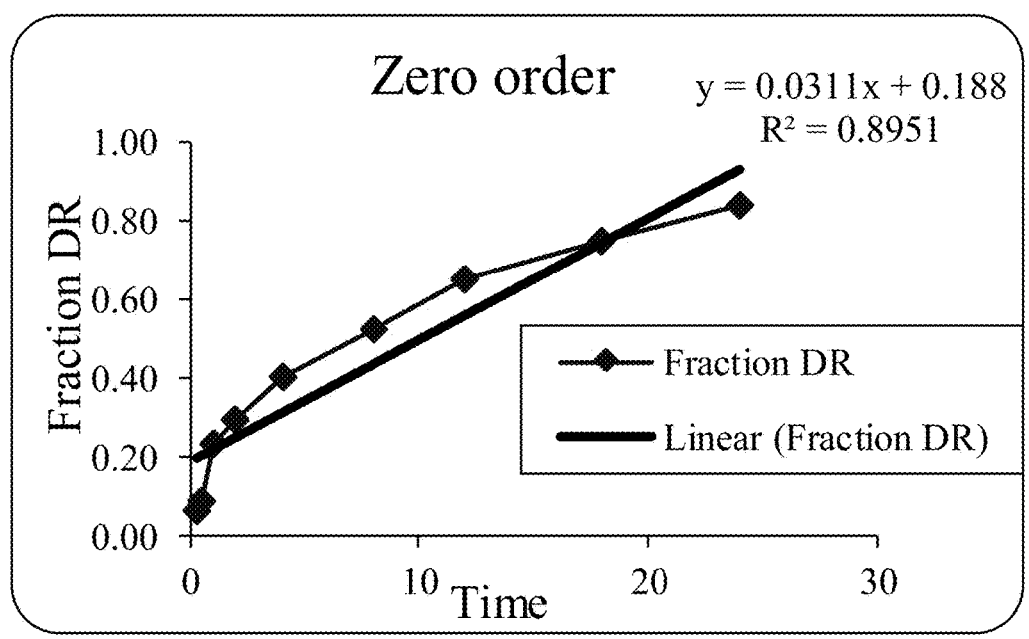
FIGS. 2A-2E: In vitro release profile of topical gel

FIG. 2A: Zero order; Fraction DR and Time, y=0.0311x+0.188 and $R^2$=0.8951

Figure 2B:
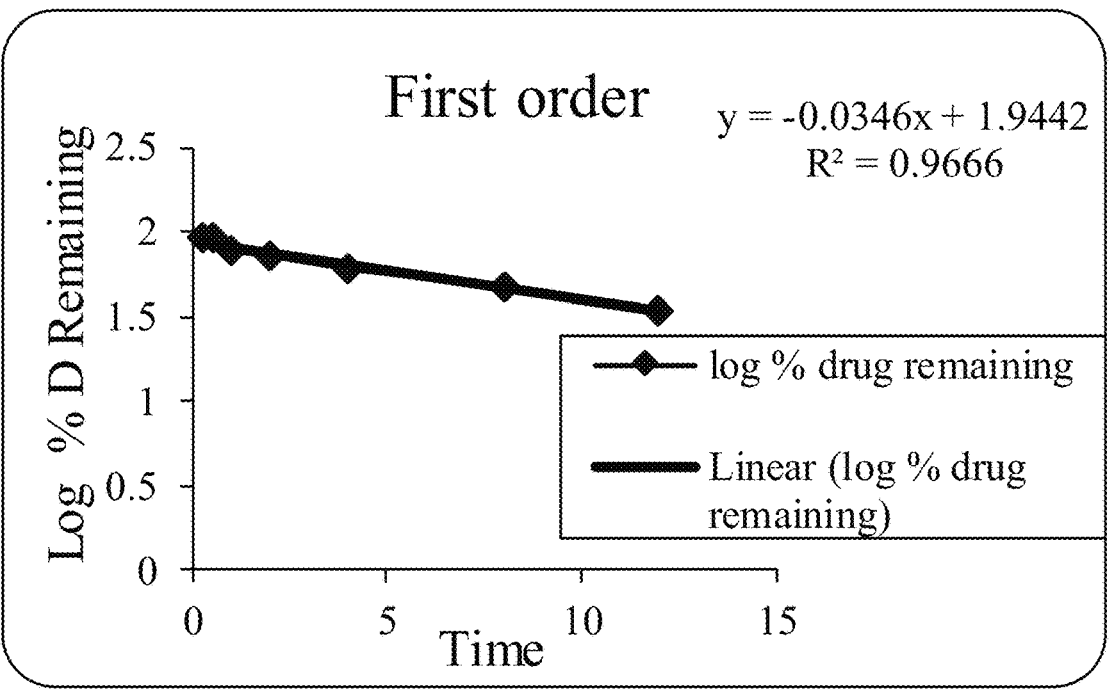

FIG. 2B: First order, Log % D Remaining to Time, y=−0.0346x+1.9442 and $R^2$=0.9666.

Figure 2C:
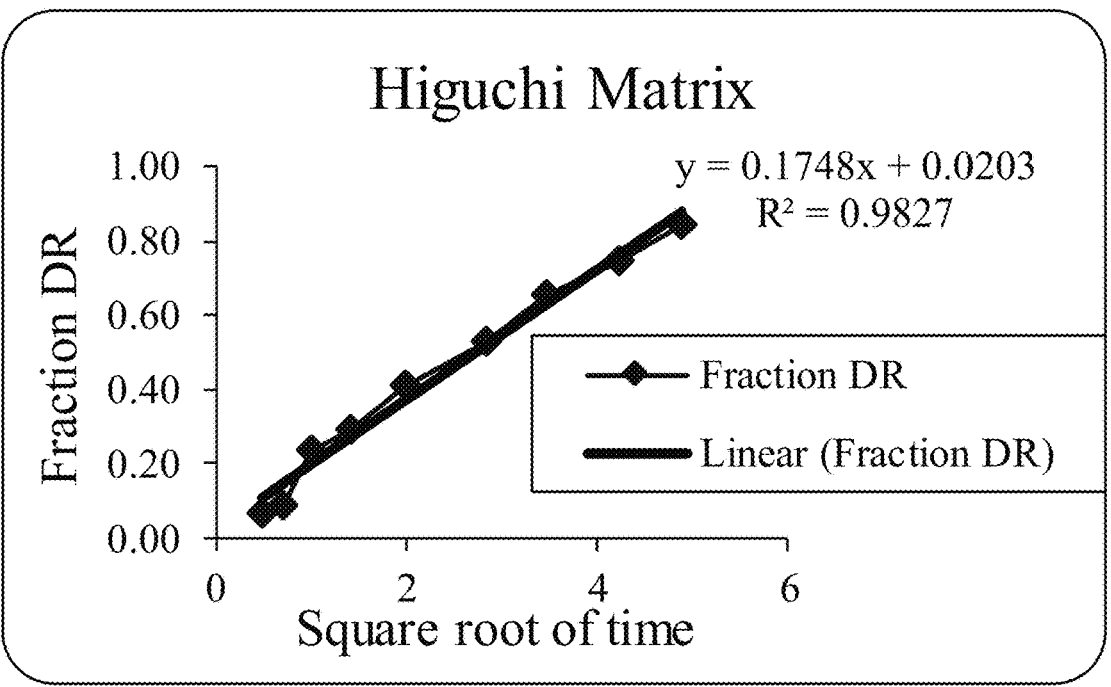

FIG. 2C: Higuchi Matrix, Fraction DR to Square root of time, y=0.1748x+0.0203 and $R^2$=0.9827.

Figure 2D:
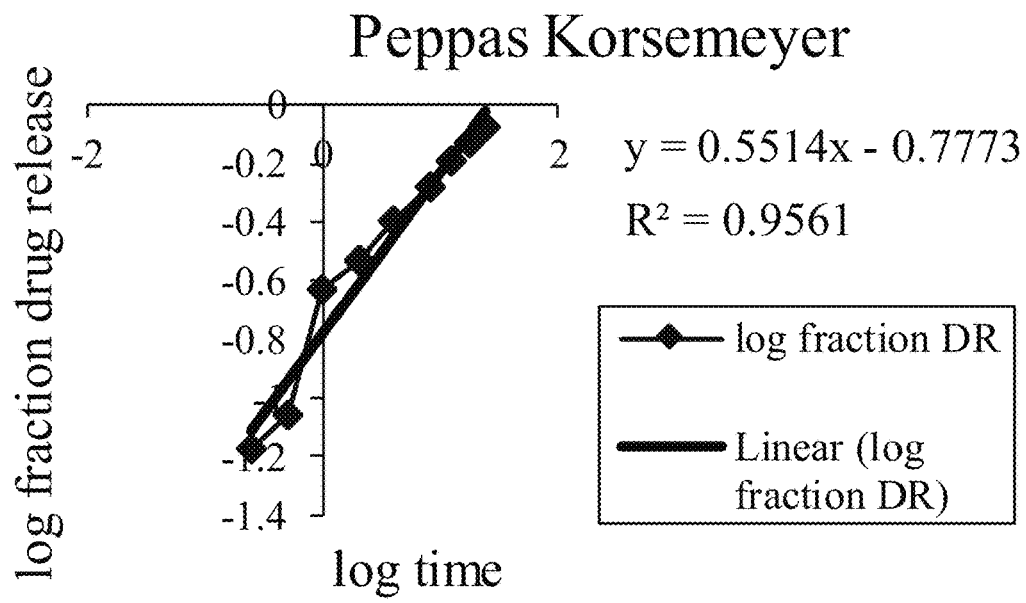

FIG. 2D: Peppas Korsemeyer, log fraction drug release to log time, y=0.5514x−0.7773 and $R^2$=0.9561.

Figure 2E:
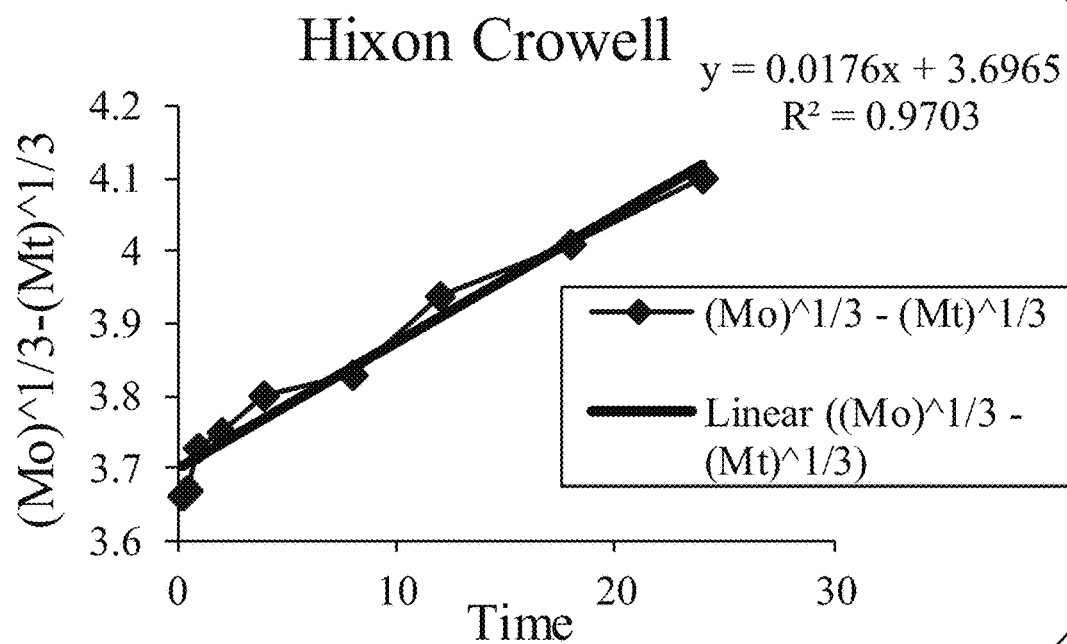

FIG. 2E: Hixon Crowell, (Mo)-⅓-(Mt)-⅓ to Time, y=0.0176x+3.6965 and $R^2$=0.9703.

TABLE 4

| In vitro release model fitting in terms of linear regression coefficient ($R_2$) values | |
|---|---|
| Model | R2 |
| Zero Order | 0.8951 |
| First Order | 0.9666 |
| Higuchi | 0.9827 |
| Peppas Kors | 0.9561 |
| Hixon Crowell | 0.9703 |

3.4. Permeation Studies Using Rat Skin

Permeation studies through rat skin was carried out for example formulation F3. The permeation drug from the nanogel was found to be 79.94±2.88%.

Figure 3:
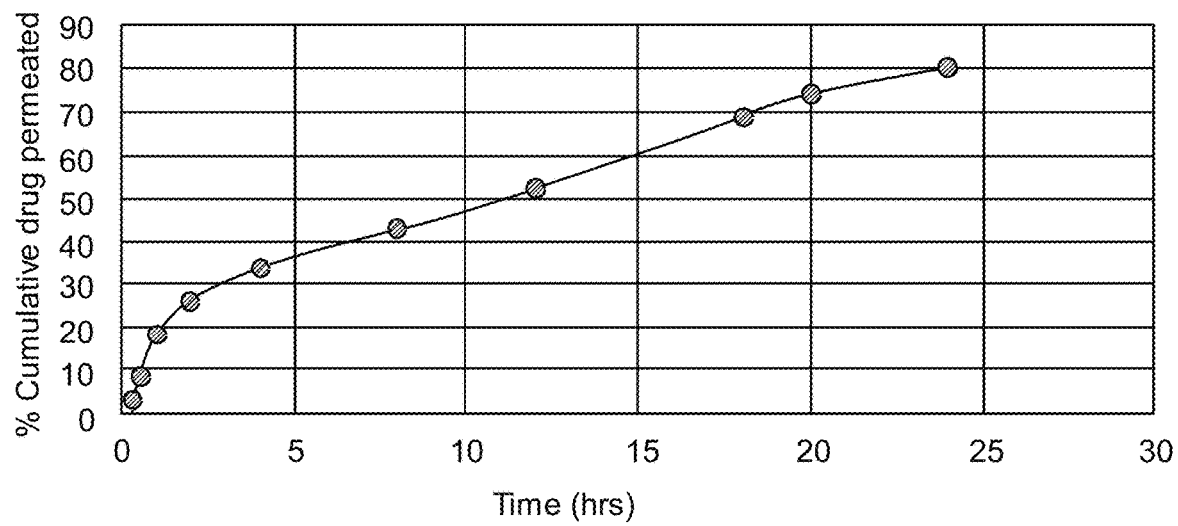
FIG. 3: Skin permeation studies of topical gel

FIG. 3: Skin permeation studies of topical gel

3.5. Evaluation of Nanogel

3.5.1. Viscosity Determination

The viscosity of the example formulation F3 was found to be 3830 cP. The viscosity results helped to study the influence of various formulation parameters on viscosity of the preparations. It was observed from FIG. 4 (*b*) that with an increase in shear, the viscosity was decreased in the formulation.

Figure 4A:
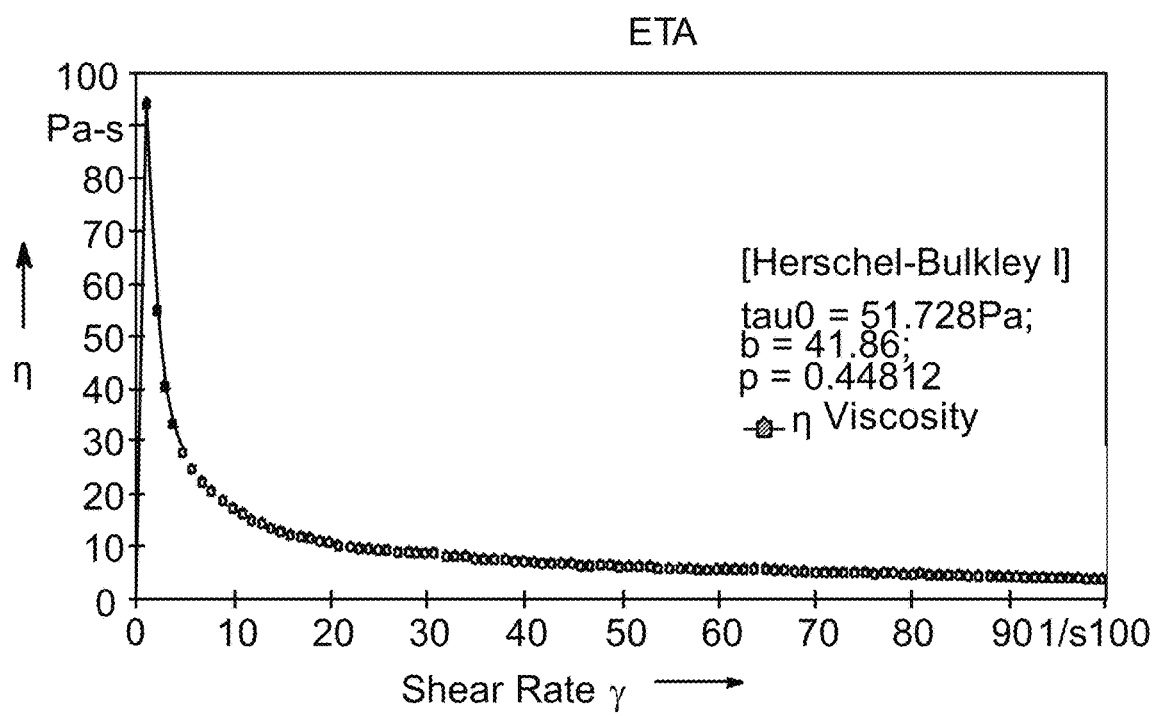
FIGS. 4A-4C: Rheograms of formulation F3
Figure 4B:
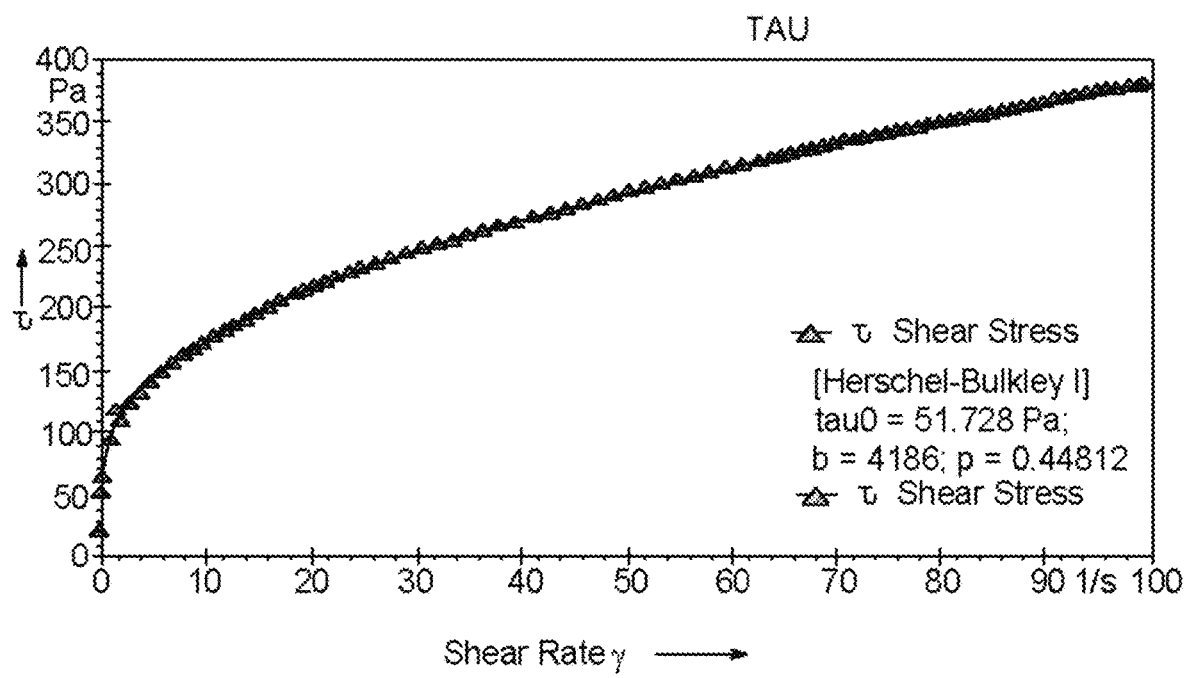
Figure 4C:
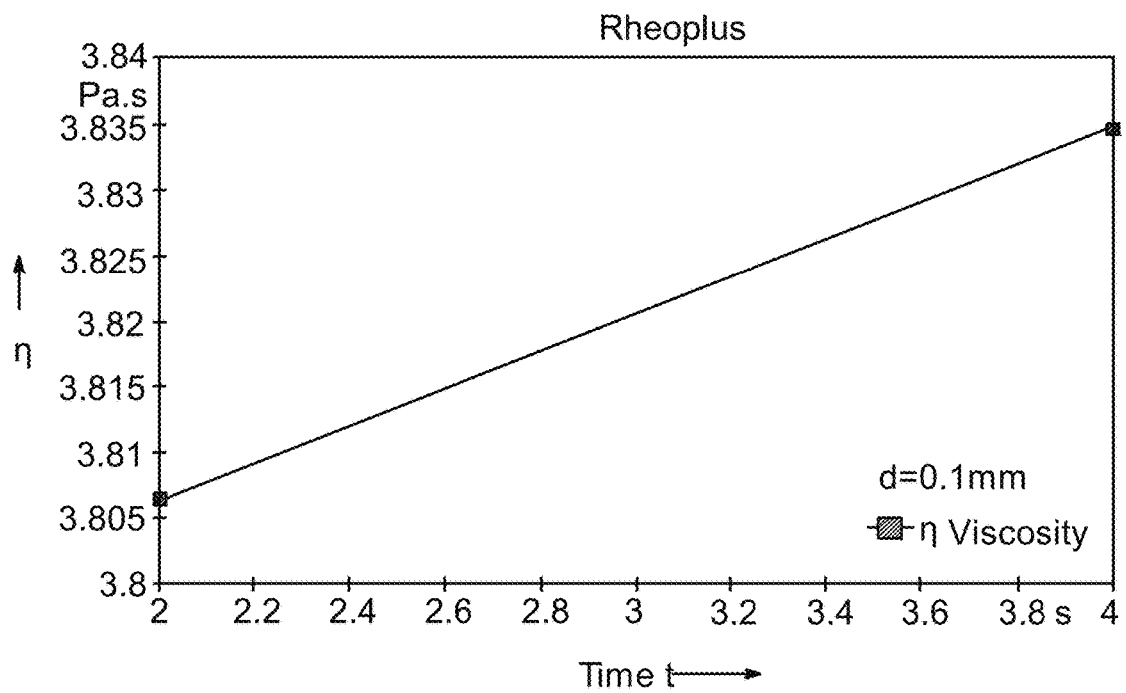

FIGS. 4A-4C: Rheograms of Formulation F3

3.5.2. Determination of Extrudability

The extrudability of the example formulation F3 was found to be 1.5±0.65 (g/cm$^2$). It was found that extrudability of nanogel was a function of concentration of Carbopol Ultraze 21. Extrudability decreases with an increase in the concentration of Carbopol Ultraze 21.

3.5.3. Determination of Spreadability

Spreadability of the example formulation F3 was found to be 443 g. The value of spreadibility indicate that the nanogel is easily spreadable by small amount of the shear. On increasing the concentration of gelling agent, there is a decrease in spreadibility.

Figure 5:
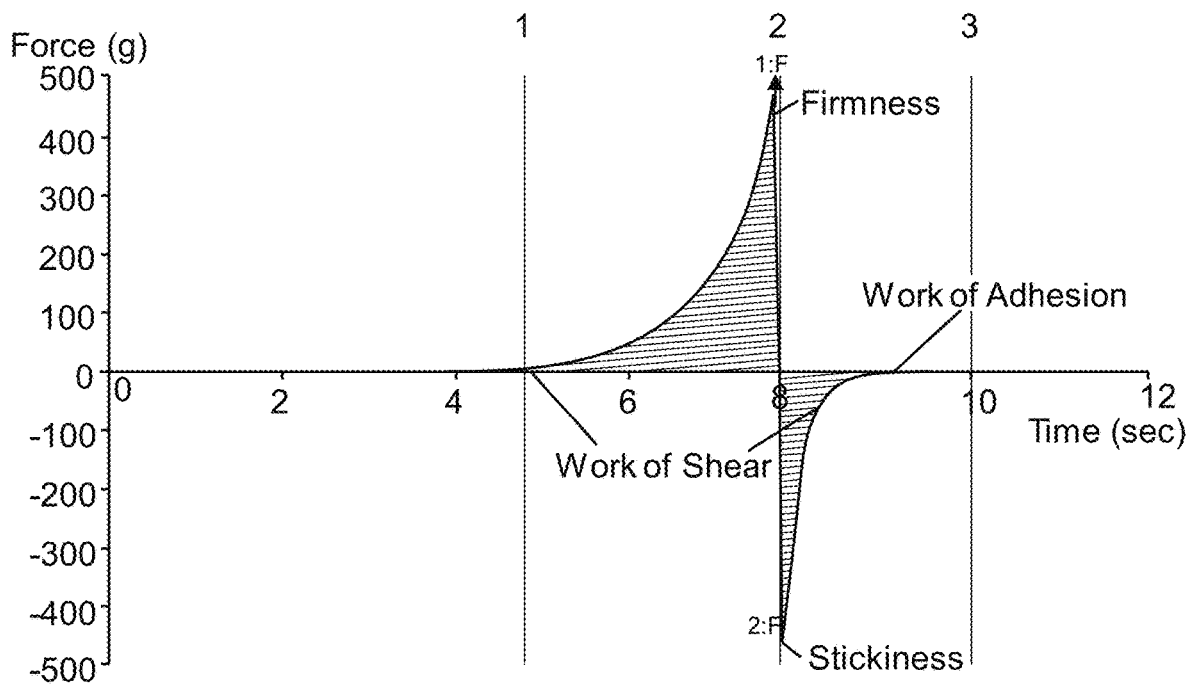
FIG. 5: Texture analysis of the example formulation F3

FIG. 5: Texture analysis of the example formulation F3

3.5.4. Texture Analysis by Using Texture Analyzer

Texture analysis of the example formulation F3 was performed and determined parameters such as firmness, consistency and cohesiveness of the formulation are presented in Table 5 higher the value of consistency, thicker is the sample. The negative area which is a measure of the total resistance to the withdrawal force indicates sample consistency.

Figure 6:
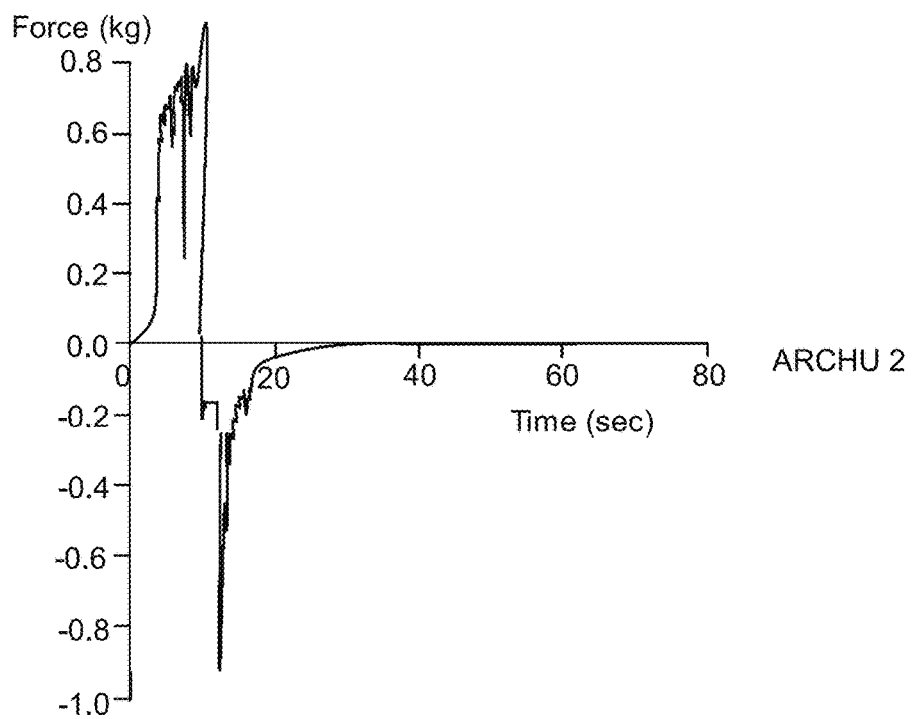
FIG. 6: Texture analysis of the example formulation F3

FIG. 6: Texture analysis of the example formulation F3

TABLE 5

| Texture profile of the example formulation F3 | |
|---|---|
| Texture profile | Gel |
| Firmness (g) | 0.8*1000 |
| Consistency (gs) | 0.45*1000 |
| Cohesiveness (−value) (g) | −0.8*1000 |

3.5.5. Bio-Adhesive Strength Measurement

The Mean Maximum Positive Force "Adhesiveness" (g)=6.613±0.85. The bio-adhesive strength of nanogel depends upon the concentration of gelling agent, Carbopol Ultraze 21. The properties like polymer chain flexibility, ability to form hydrogen bonds and/or the extent of swelling of polymer influence the bio-adhesive strength of the formulation.

Figure 7:
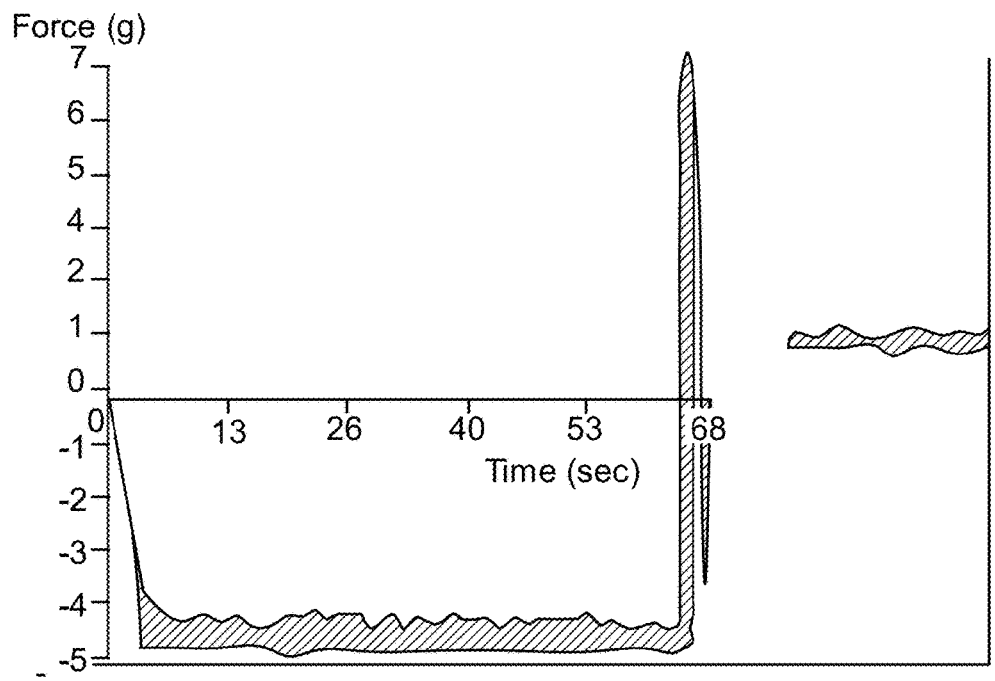
FIG. 7: Bio-adhesive strength measurement of the example formulation F3
FIG. 8 Calibration plot in distilled water; Standard Plot of 3HX in distilled water
FIG. 9 Calibration plot in Phosphate Buffer pH 7.4; Standard Plot of 3HX in PBS pH 7.4

FIG. 7: Bio-adhesive strength measurement of the example formulation F3

Conclusion

In the present work, drug 3HX loaded nanogel was developed by employing Carbopol Ultraze 21 as a gelling agent. Different penetration enhancers such as propylene glycol, polyethylene glycol and menthol were used to enhance the permeation of the drug from the nanogel. Varying the concentration of the penetration enhancer, three different formulations were prepared. The formulations were also evaluated for Color & appearance, Homogeneity, Phase Separation, Grittiness, pH and % drug content. All three formulations (F1, F2 and F3) were evaluated for in vitro release study which was carried out for 24 h. Among all the three formulations, F3 showed the highest % cumulative drug release of 84.23%. Therefore, for the further evaluation formulation F3 was selected. The amount of the drug released was incorporated into various release kinetic models. The observed best fit model was Higuchi model followed by First order release model with $R^2$ 0. 9827 and 0.9666 respectively. Skin permeation study was carried out for the example formulation F3 with 79.94±2.88% of cumulative amount of drug permeated. Rheological properties like viscosity extrudability, Spreadability, texture analysis and bio-adhesion was carried out for the example formulation F3 and results found were satisfactory for all.

Calibration Plot of 3HX Using UV-VIS Spectrophotometry

Calibration plot was prepared after taking readings for absorbance in triplicate Plots were prepared in distilled water and phosphate buffer pH 7.4

Dilutions of 100, 200, 300, 400 and 500 µg/ml were made for distilled water and phosphate buffer pH 7.4

The dilutions were scanned for determining the max

The λmax of 3HX was found to be 280 nm

Figure 8:
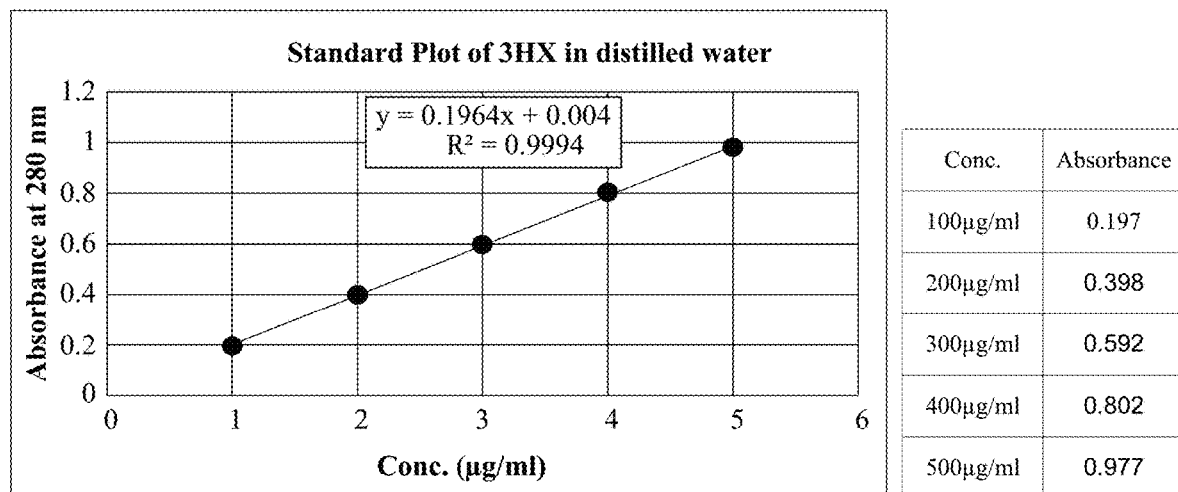

FIG. 8: Calibration plot in distilled water

Figure 9:
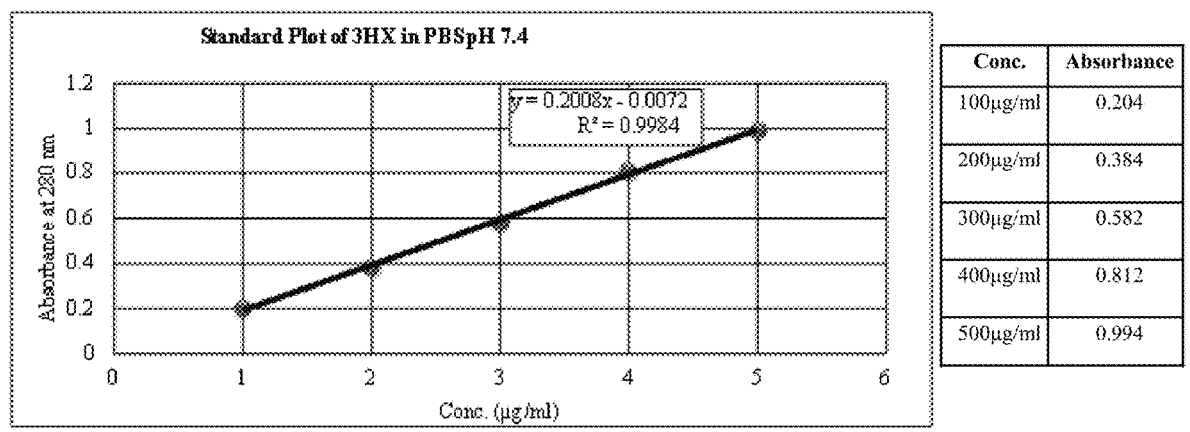

FIG. 9: Calibration plot in Phosphate Buffer pH 7.4

Figure 10:
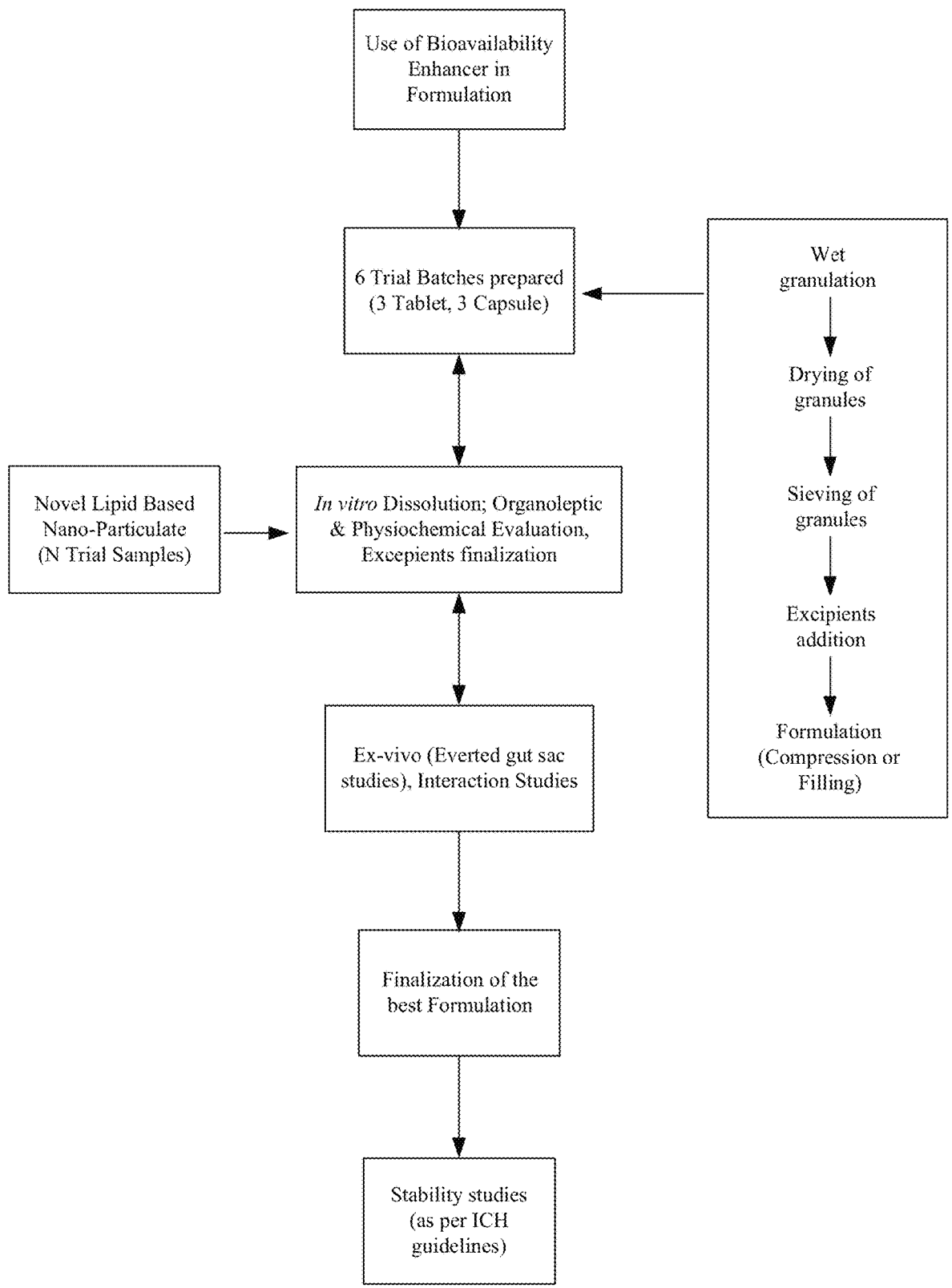
FIG. 10: Oral Formulation; Strategy, Design & Method (Oral Formulation)

FIG. 10: Oral Formulation; Strategy, Design & Method (Oral Formulation)

Tablet Preparation

The extract was homogenized and particle size of 250 nm was achieved

This was in turn mixed with a surfactant and used for tableting with excipients

Different ratios of bioenhancers were used for different batches.

Malvern zeta size results for nanosizing are still with the lab personnel

We would furnish them as soon as he hands them over to us

Ingredients of Tablets and Capsule

TABLE 6

Ingredients of tablets and capsule

| Name | Function |
| --- | --- |
| Lactose monohydrate | Diluent |
| Polyvinyl povidone k-30 | Binder |
| Magnesium stearate | Glidant |
| Piperine | Bioavailability enhancer |
| Fulvic acid | Bioavailability enhancer |
| Inulin | Bioavailability enhancer |
| Talc | Glidant |

Preparation of Granules

PVP K-30 acts as a binder

Tablets were prepared by varying the concentration of piperine and fulvic acid and keeping other things constant Granulation was done by wet granulation method for tablets the granules were sieved through 40 mesh sieve and for capsules the granules were sieved through 80 mesh sieve.

Organoleptic Evaluation

TABLE 7

Organoleptic Evaluation

| Parameters | Results |
| --- | --- |
| Colour | Brown |
| Odour | Distinct, as that of extract |
| Hygroscopicity | Not hygroscopic as that of extract |
| Texture | Smooth |

Different Prepared Batches

Batch 1—tablet with equal concentration of piperine and fulvic acid

Batch 2—capsules with equal concentration of piperine and fulvic acid

Batch 3—tablet with high fulvic acid concentration

Batch 4—capsule with high fulvic acid concentration

Batch 5—tablet with high piperine concentration

Batch 6—capsule with high piperine concentration

FIGS. 11A-11F: Dissolution Profiles of different batches

Dissolution Test Apparatus

Figure 11A:
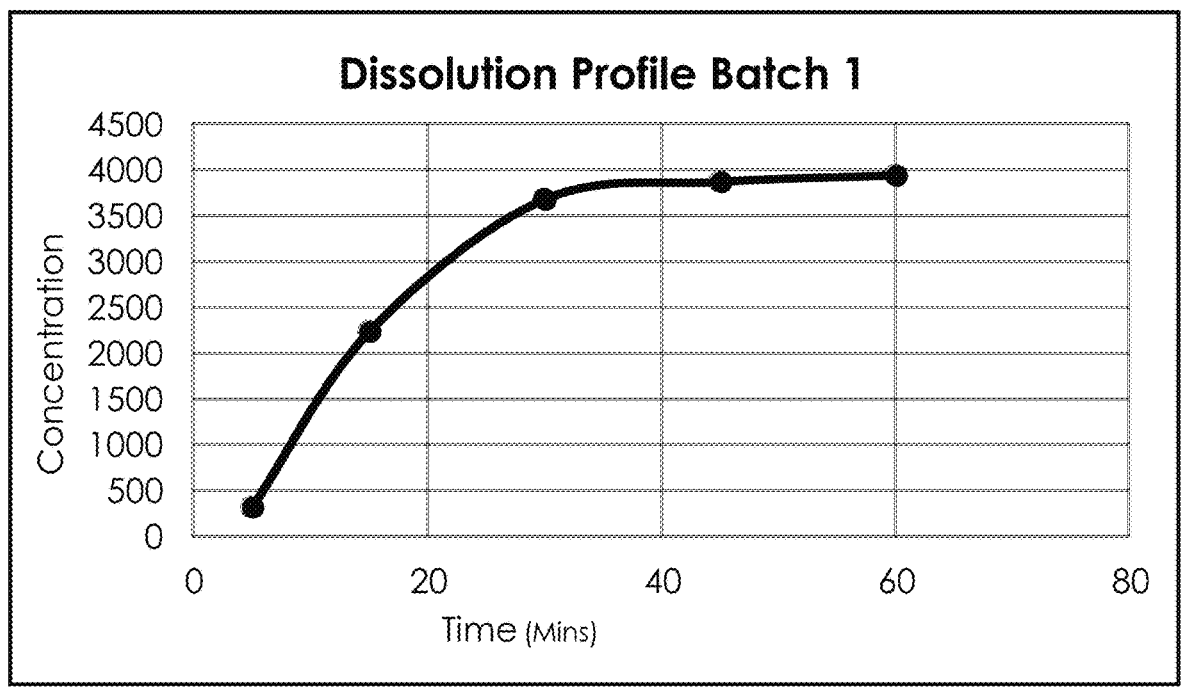
FIGS. 11A-11F: Dissolution Profiles of different batches

FIG. 11A: Dissolution Profile Batch 1

Figure 11B:
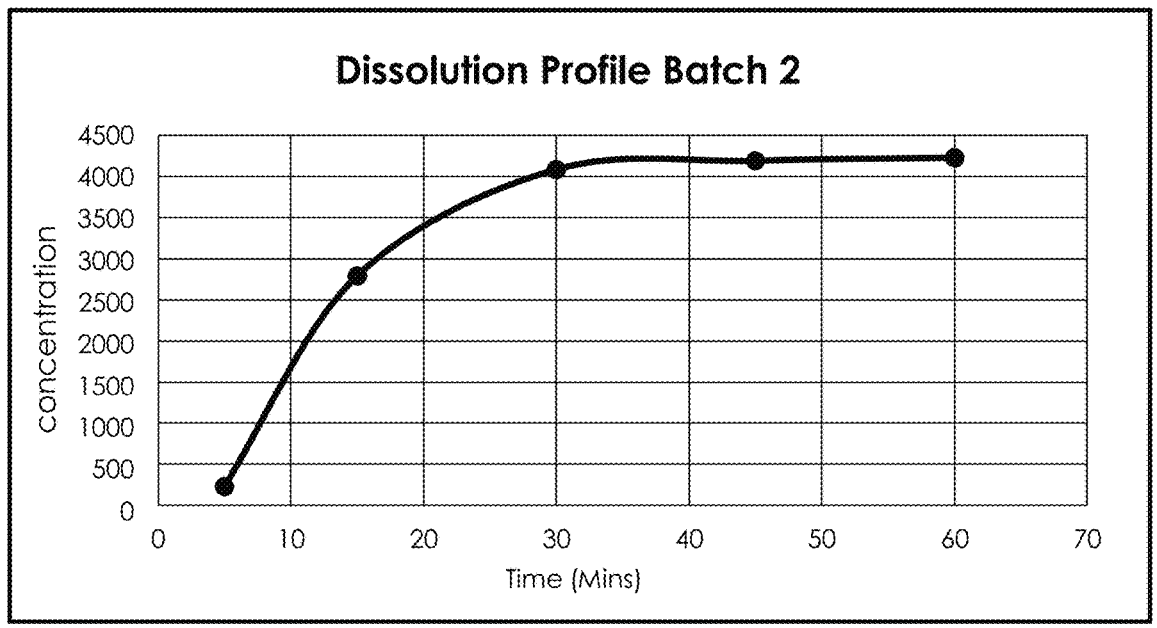

FIG. 11B: Dissolution Profile Batch 2

Figure 11C:
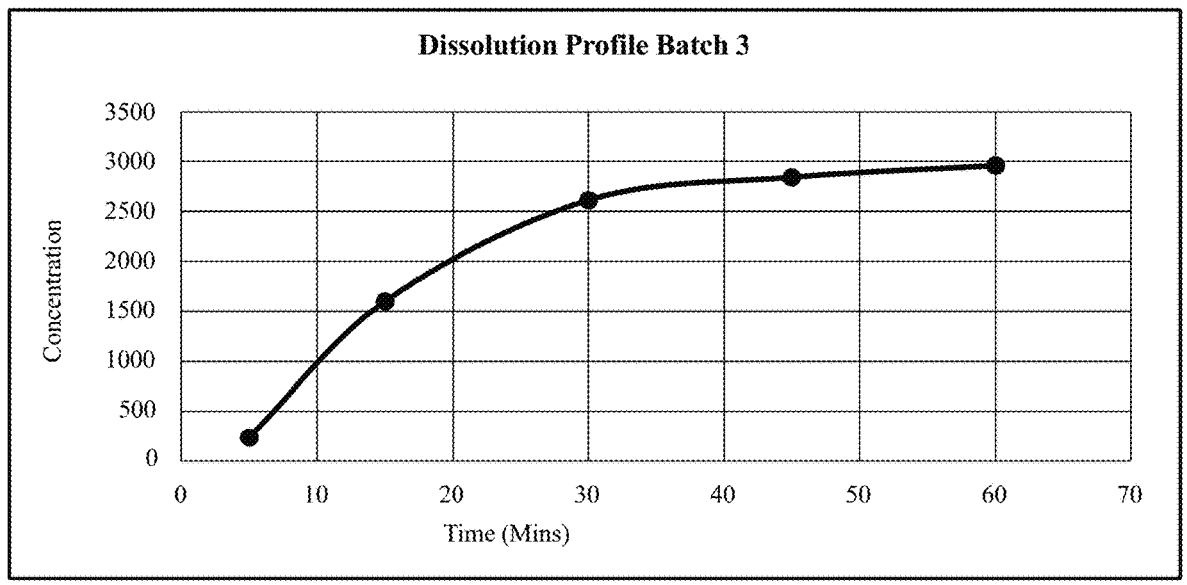

FIG. 11C: Dissolution Profile Batch 3

Figure 11D:
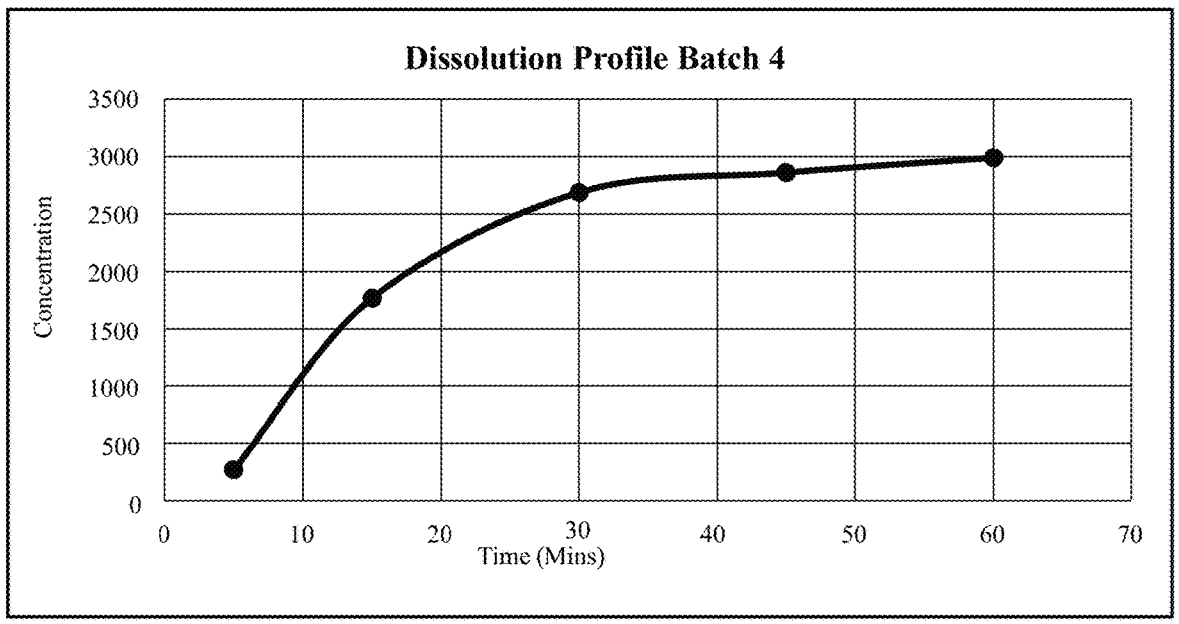

FIG. 11D: Dissolution Profile Batch 4

Figure 11E:
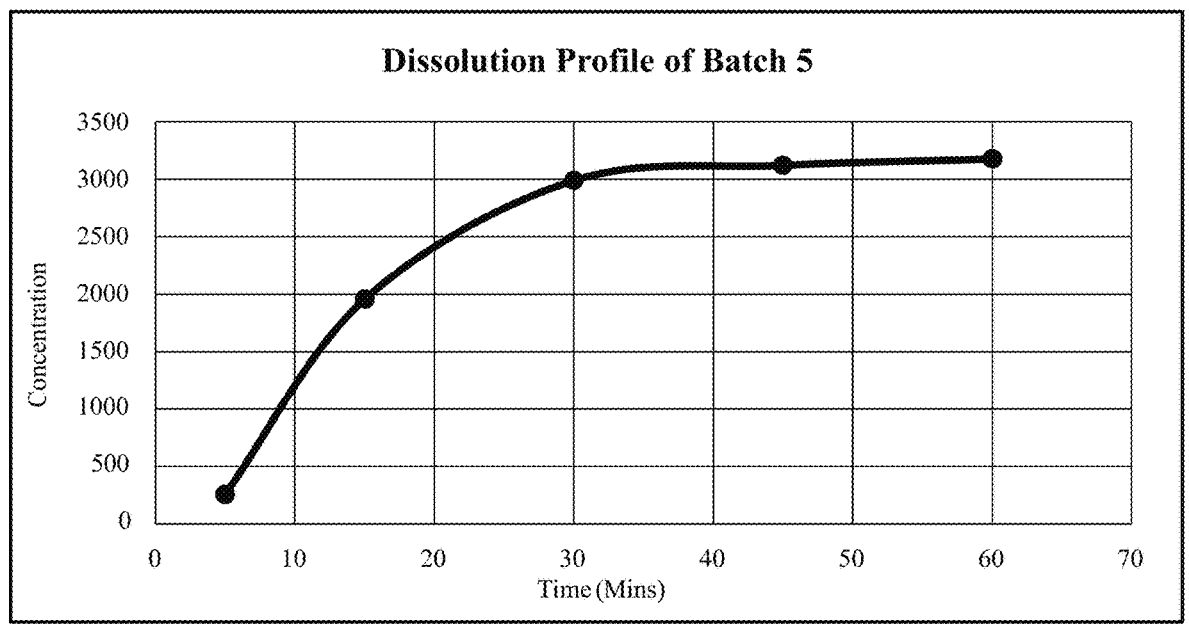

FIG. 11E: Dissolution Profile Batch 5

Figure 11F:
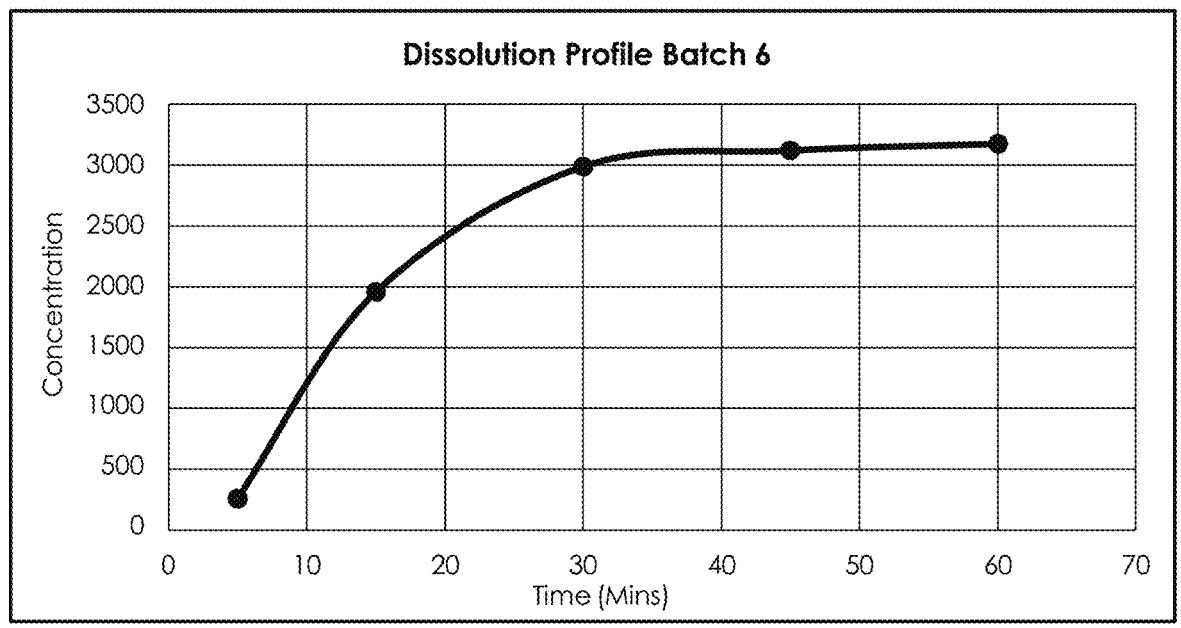
Figure 12A:
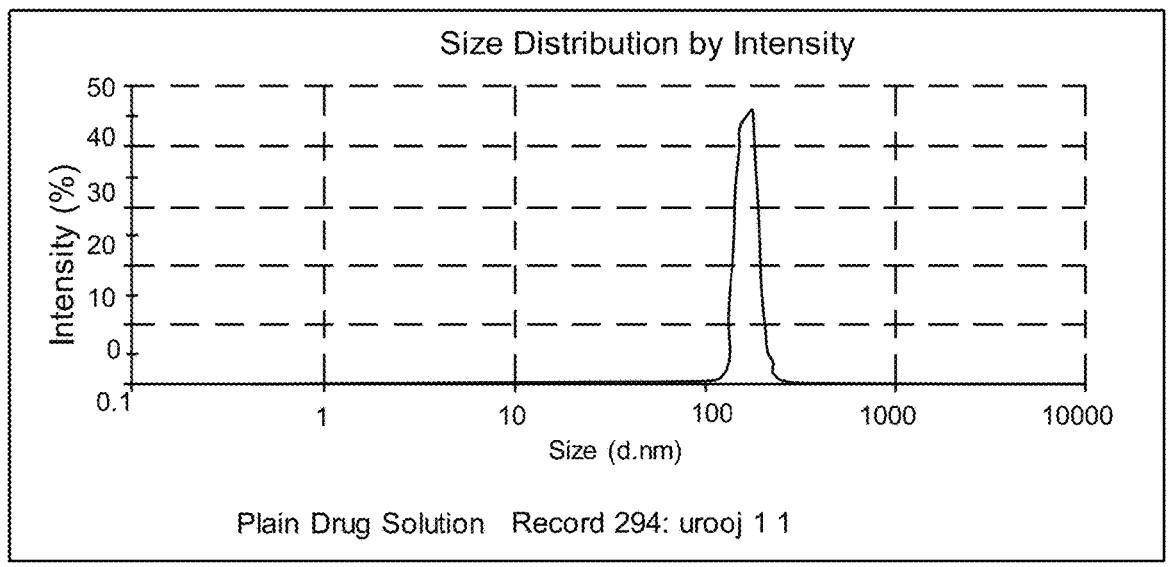
FIG. 12A-12D: Sizing results of example nanoformulations; Plain Drug Solution
Figure 12B:
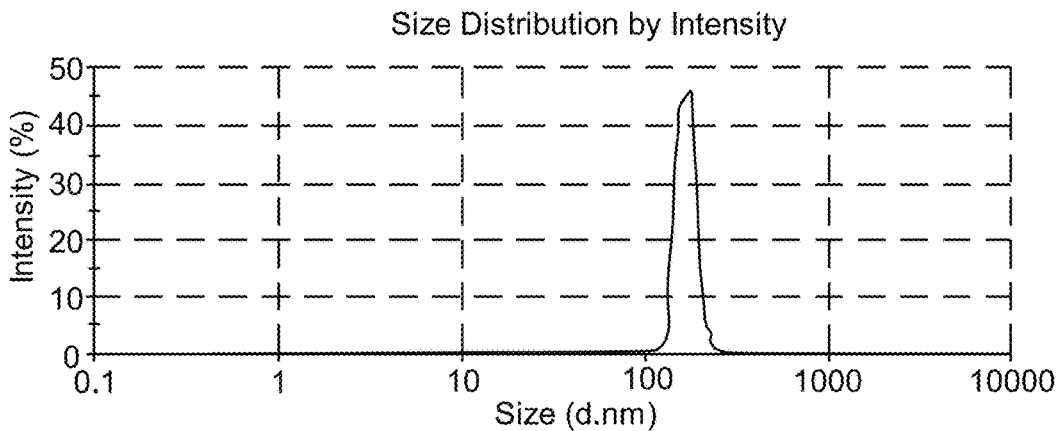
Figure 12C:
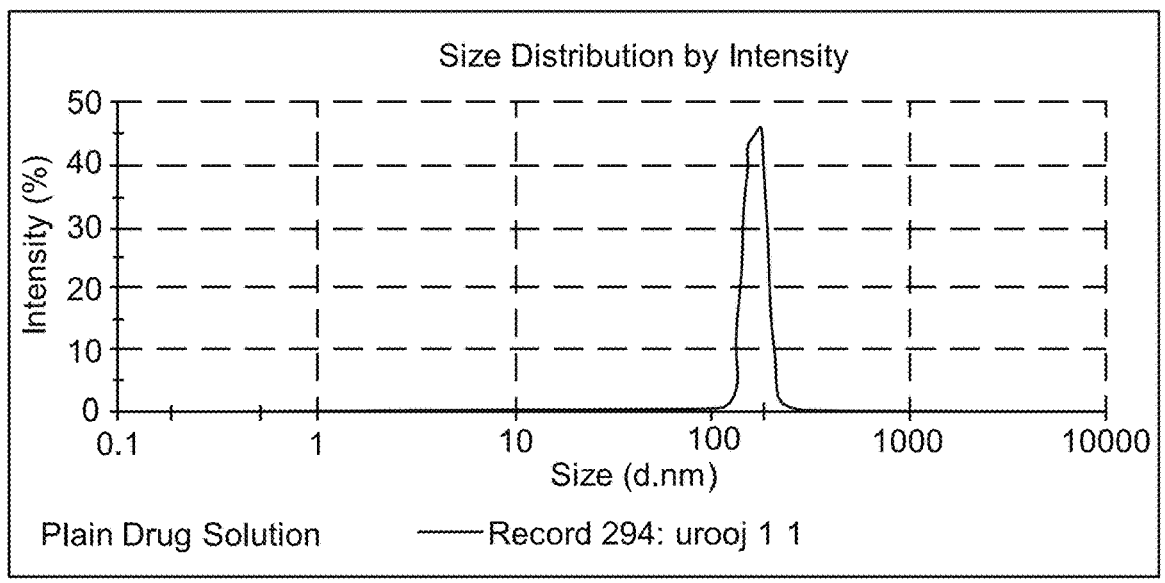
Figure 12D:
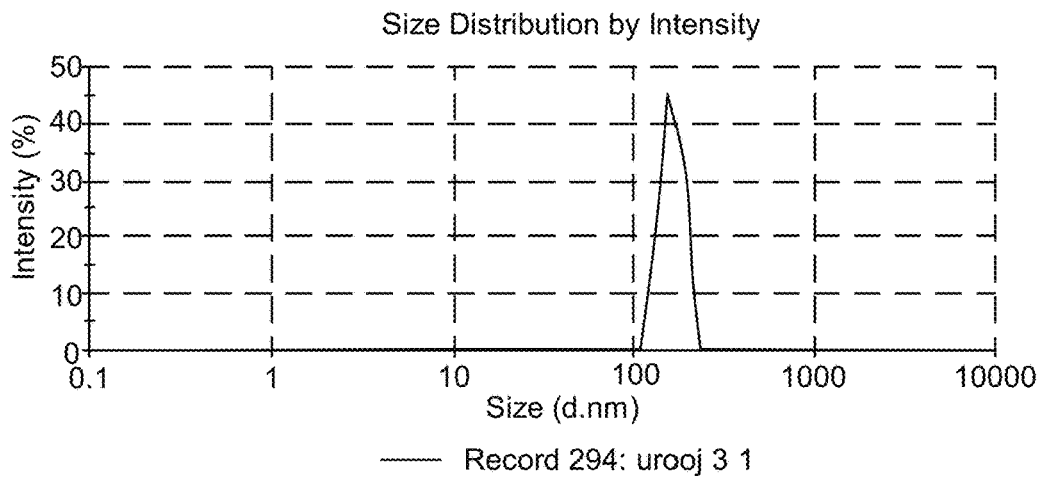

FIG. 11F: Dissolution Profile Batch 6

Results of Dissolution Experiment

Results of Dissolution Experiment

After conducting the experiments it was found that equal ratios of piperine and fulvic acid may be included in the tablets Conditions for the tablets were determined per the results.

Batch 1 and 2 gave good release profiles as indicated by higher drug content release with time.

Evaluation of Oral Formulations

Weight Variation 20 tablets were weighed and weight variations was calculated

It was found within the range of 5% which is in accordance with IP

Hardness Evaluation

It was carried out using Monsanto hardness tester

IP gives the limit of 4-10 kg for hardness

The tablets were found to have hardness in the range 5.5-6 kg

Disintegration Test

It was performed using disintegration test apparatus

It was carried out in 1 litre beaker having distilled water at 37 degree Celsius The apparatus undergoes 29-32 cycles per minute The disintegration time was found to be 15 minutes.

Friability Testing

It was performed using Roche Friabilator at 25 rpm for 4 minutes

IP has limits of 0.5-1%

The tablets show friability of less than 1%

Novel Lipid Based Nanoparticulate Formulation of 3HX

Stearic acid, poloxamer 188, tween 80 and PEG 400 have been used to emulsify the drug Nanosizing has been achieved by homogenizing the prepared batch using sonicator and dyno mill About 15 cycles were performed Samples have been sent for size analysis.

Work to be Done:

In vitro drug release study by dialysis membranes for the different oral formulations Nano sized extract tablets Lipid nanoparticle formulation Ex vivo gut permeation studies for different batches of tablets and lipid formulation.

Comparative Dissolution Studies for different types of formulations:

Different batches of Nano sized extract tablets

Lipid nanoparticle formulation

Interaction Studies to study compatibility of ingredients

Formulation Finalization

Stability studies of example formulation according to the ICH guidelines: Stability chamber studies for 25 degree Celsius and 40 degree Celsius.

Accelerated stability studies

Update on oral formulation

Work to be Done in Next Two Weeks:

Formulation of 2 more batches of lipid formulations by varying different excipients.

vitro drug release study by dialysis membranes for the different oral formulations Nano sized extract tablets (Batches 1,2,3,4,5,6)

Lipid nanoparticle formulation (Batches 1,2,3)

Ex vivo gut permeation studies for different batches of tablets and lipid formulation.

Nano sized extract tablets (Batches 1,2,3,4,5,6)

Lipid nanoparticle formulation (Batches 1,2,3)

Sizing Results

Figure 13A:
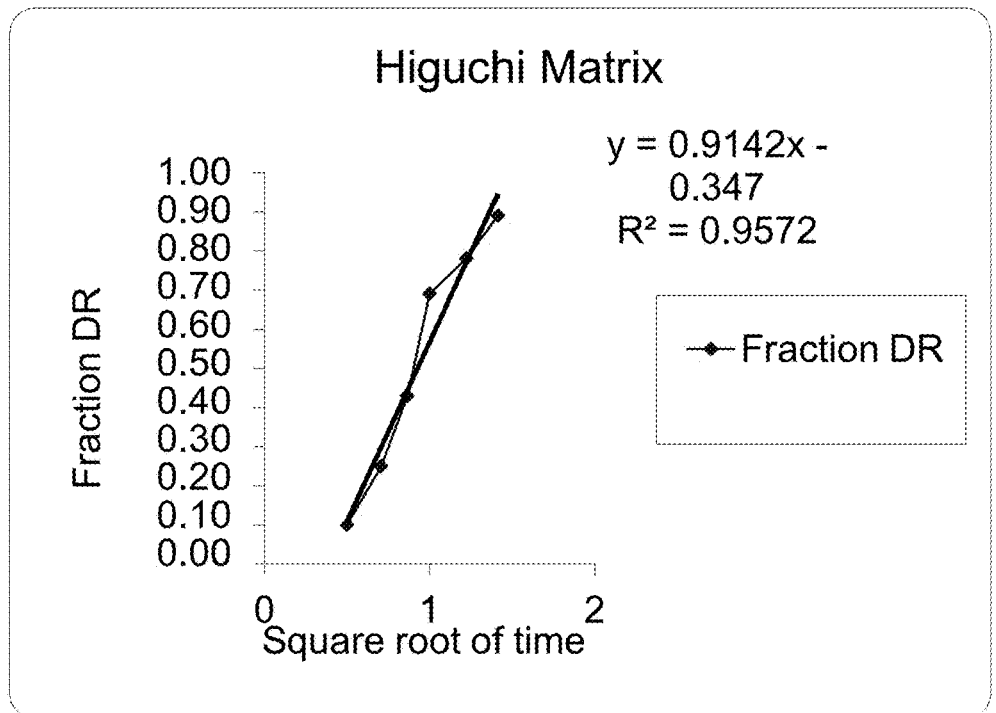
FIGS. 13A-13E: Release models

FIG. 12A-12D: Sizing results of example nanoformulations; Size Distribution by Intensity; Plain Drug Solution In vitro Release Studies Release models FIGS. 13A-13E: Release models FIG. 13A: Higuchi Matrix, Fraction DR and Square root of time, y=0.9142x−0.347 and $R^2$=0.9572

Figure 13B:
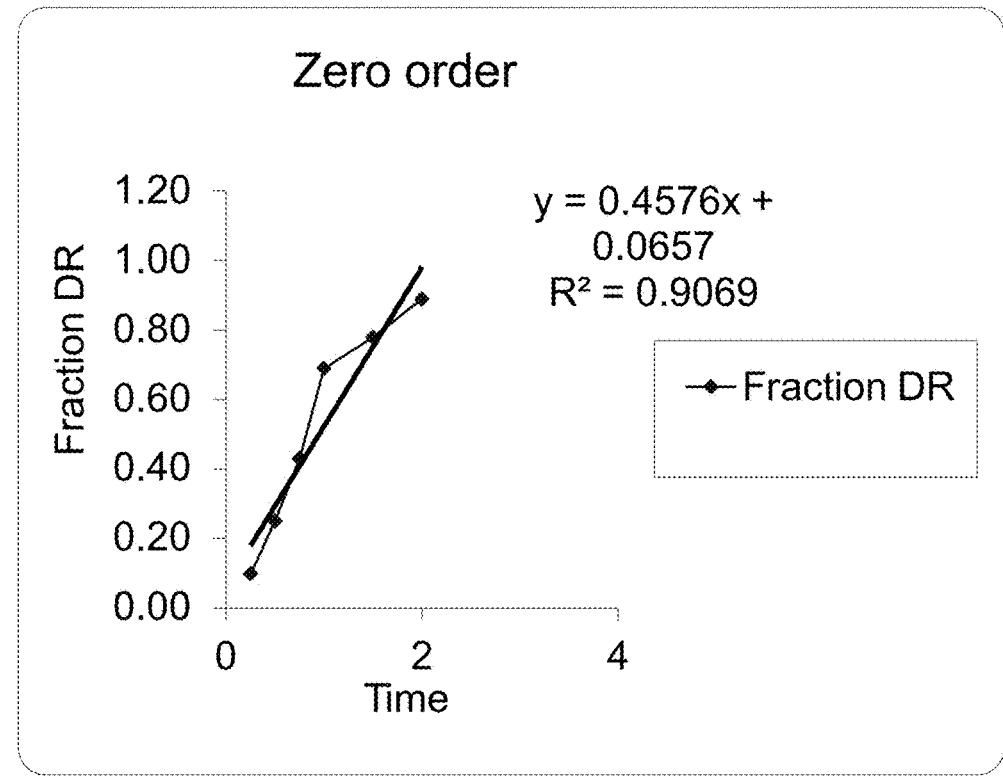

FIG. 13B: Zero order, Fraction DR and Time, y=0.4576x+0.0657 and $R^2$=0.9069

Figure 13C:
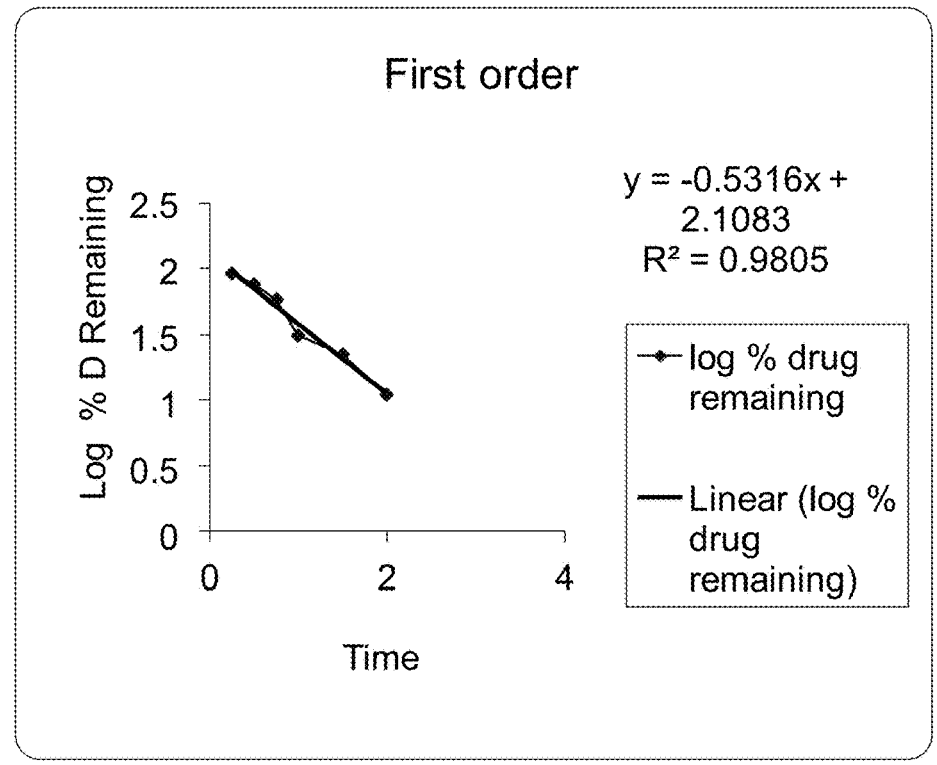

FIG. 13C: First order, Log % D Remaining and Time, y=−0.5316x+2.1083 and $R^2$=0.9805

Figure 13D:
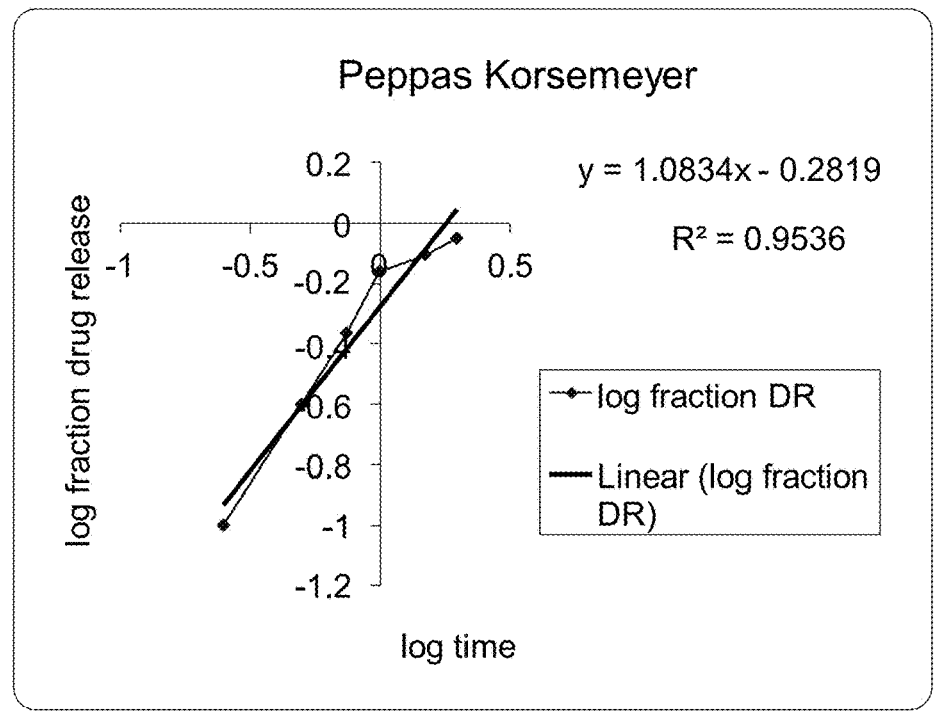

FIG. 13D: Peppas Korsemeyer, Log Transaction Drug Release and log time, y=1.0834x−0.2819 and $R^2$=0.9536

Figure 13E:
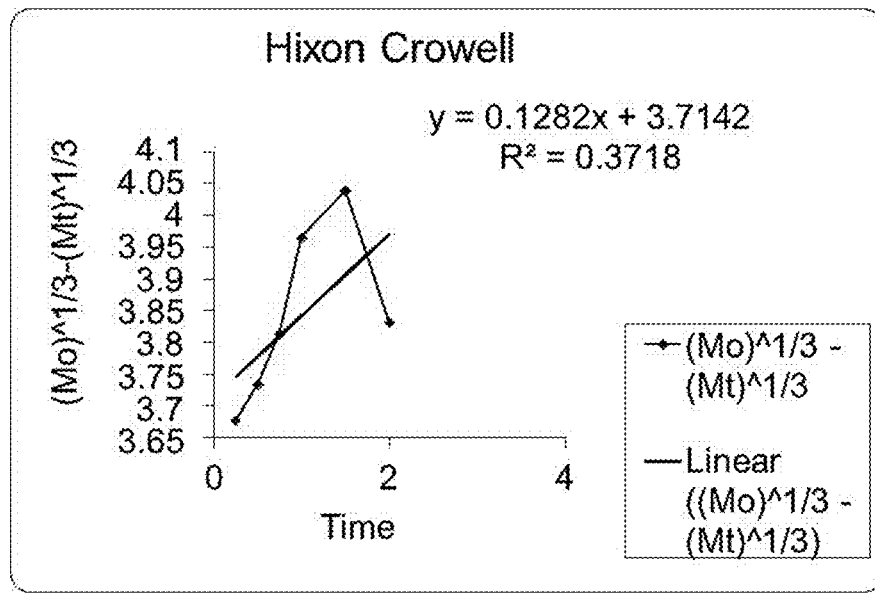

FIG. 13E: Hixon Crowell, $(Mo)$-⅓-$(Mt)$-⅓ and Time, y=0.1282x+3.7142 and $R^2$=0.3718

TABLE 8

Table 8: In vitro Release Studies, Equation for Peppas Model and Peppas Model

| Equation for Peppas Model | Peppas Model |
| --- | --- |
| $Mt/M\infty = at^n$ | Slope = 0.6132 |
| $\ln(Mt/M\infty) = \ln a + n \ln t$ | Slope = n * 2.303 |
| $\log(Mt/M\infty) = \log a + n \log t/2.303$ | n = Slope of Korsemeyer Peppas/2.303 |
| where (Mt/M∞) = released fraction of drug wrt time | n = 1.0834/2.303 = 0.470 |

Ex Vivo Gut Permeation Studies

Similar strengths of: Plain drug solution. Tablet formulation with equal concentration of permeation enhancer. Novel lipid nanoparticle formulation. A suitable section of intestine of rat was obtained and filled with 1 ml dilution of each type.

The sac was ligated and suspended in Kreb's solution with aeration, constant stirring and temperature maintained at 37 degree celcius.

Method:

Wistar male rats weighing 250 g were procured. Abdomen the sack was dissected to obtain intestinal tissue measuring 5 cm in length. The assembly was set up having circulating water bath and Krebs solution with aeration (95% O2 and 5% CO2). The lower portion was ligated and tided to a thread and lowered in the assembly with solution of the formulation inside the tissue. 1 ml of aliquot was withdrawn at time intervals of 0, 0.25, 0.5, 1, 1.5 and 2 hours and replaced with fresh Krebs solution to maintain sink condition.

The samples were analyzed for drug content

Calculation of apparent permeability coefficient (APC)

The APC of plain drug solution and nanocomposite formulation was calculated from following equation:

$$APC = F/A * C_0 \text{ cm/min}$$

Where F is the permeation flux (µg/min), A is the surface area of the barrier membrane and $C_0$ is initial concentration of drug in the mucosal medium.

F is calculated by taking the slope of linear portion of the graph between cumulative amount of drug permeated against time.

Surface area was taken as 7.85 $cm^2$ taking length of sac 5 cm and assuming they have a cylindrical shape with their inner diameter being 0.5 cm considering that no villi and microvilli are present in the mucosal side.

Figure 14A:
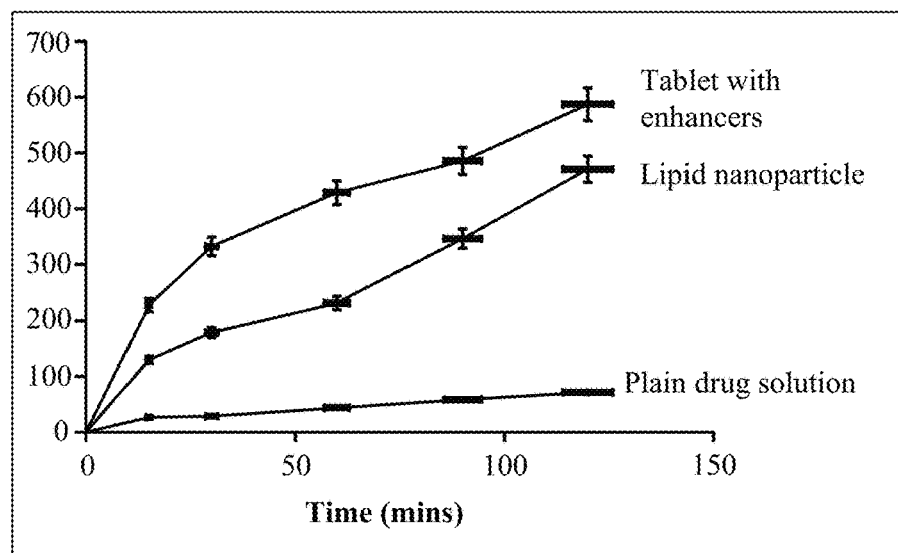
FIG. 14A: Cumulative amount of drug permeated vs Time

FIG. 14A: Cumulative amount of drug permeated vs Time

Figure 14B:
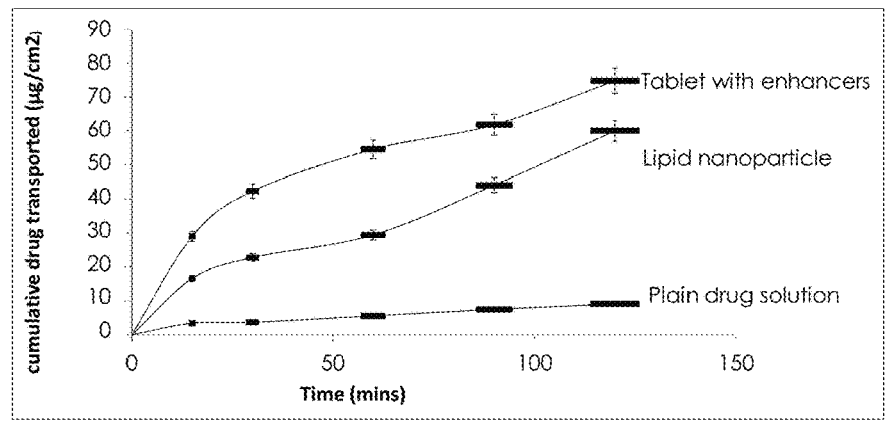
FIG. 14B: Cumulative drug transport vs Time

FIG. 14B: Cumulative drug transport vs Time

Figure 14C:
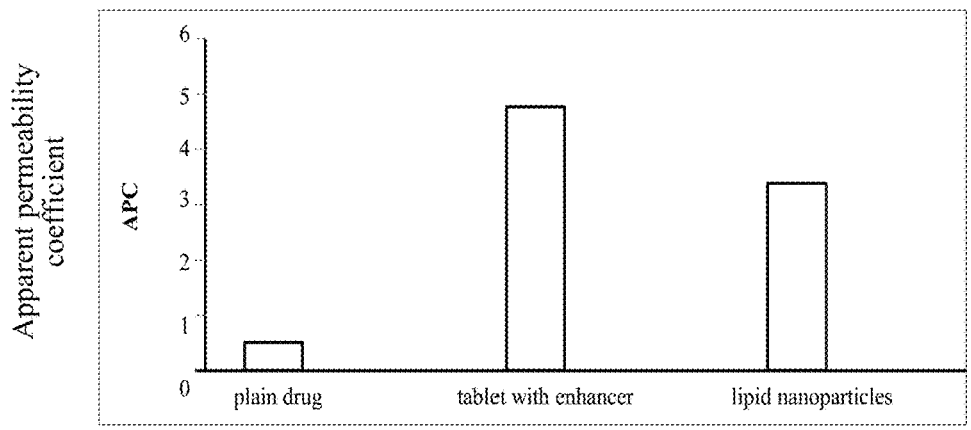
FIG. 14C: Apparent permeability coefficient

FIG. 14C: Apparent permeability coefficient

Work to be Done:

To resolve lyophilization issue of lipid nano-particle

Ex vivo gut permeation studies & in-vitro dissolution studies for different batches of tablets and lipid formulation; Comparison with existing tablet formulation. Interaction Studies to study compatibility of ingredients. SEM/TEM of Lyophilized Nano-particle Comparative analysis of the formulation prototype with DRF formulation Confocal Microscopy Finalization of example formulation prototype Stability studies of example formulation according to the ICH guidelines: Stability chamber studies for 25 degree Celsius and 40 degree Celsius.

Accelerated stability studies

Figure 15:
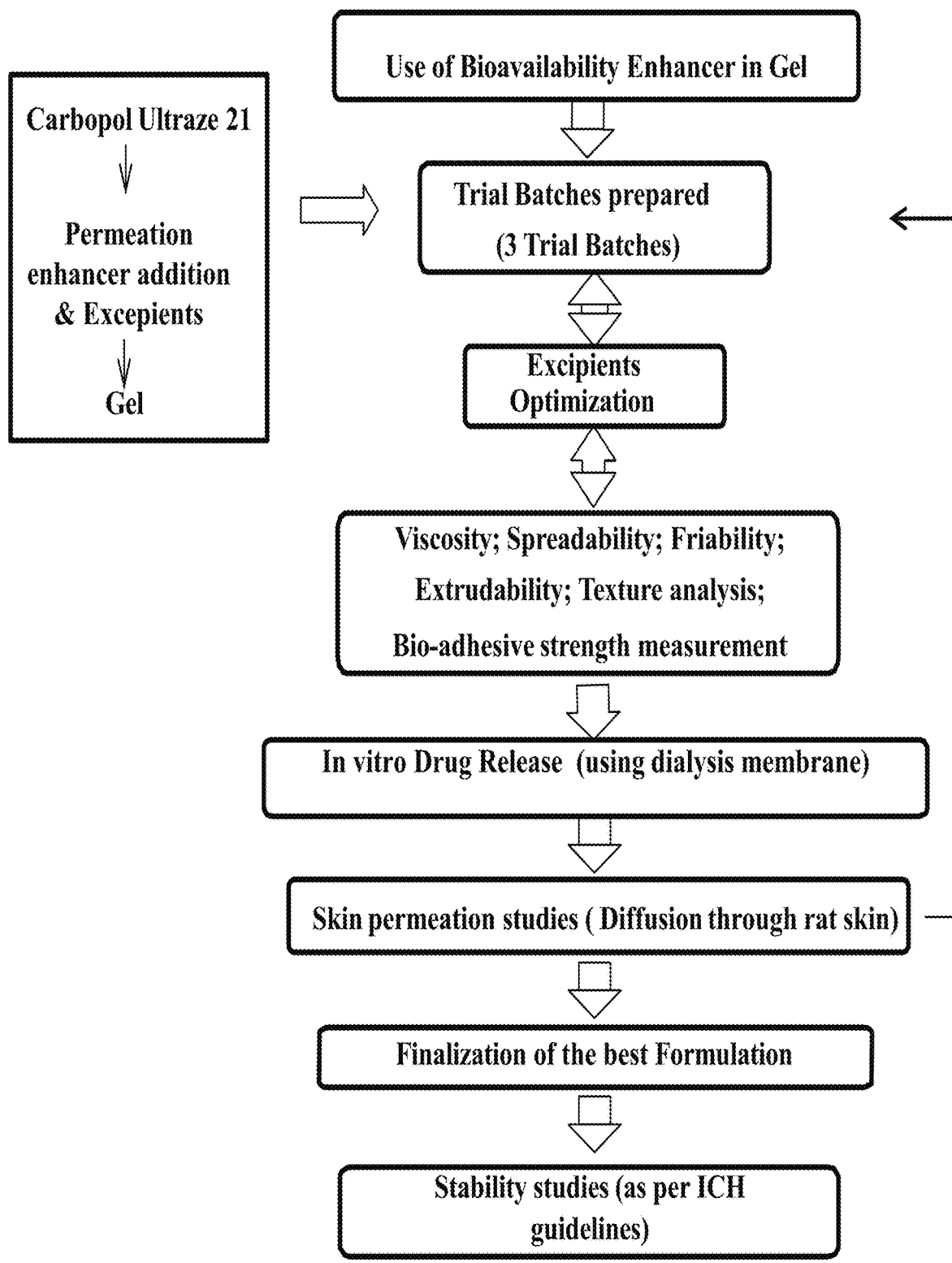
FIG. 15: Topical Gel Formulation; Strategy, Design & Method (Topical Formulation)

FIG. 15: Topical Gel Formulation; Strategy, Design & Method (Topical Formulation)

Preparation of Topical Formulation Gel

Gels were prepared by cold mechanical method. Polymer (Carbopol Ultraze 21) was weighed and it was sprinkled slowly on the surface of purified water with continuous stirring for 2 hr. After which it was stirred continuously by mechanical stirrer, till polymer soaked in the water. Now propylene glycol and Polyethylene glycol 400 (PEG 400), which behaves as penetration enhancers and DMDM Hydantoin as preservative was added to the gel, followed by menthol and isopropyl alcohol. Now the drug 3HX was added to the gel with continuous stirring till drug get dispersed in gel completely. Finally with continuous stirring, triethanolamine was added to neutralize the gel and it maintains the pH of the gel.

TABLE 9

Preparation of Topical formulation gel
Table 9: Preparation of Topical formulation gel

| Ingredients | F1 | F2 | F3 |
| --- | --- | --- | --- |
| Drug (3HX) (gm) | 2.5 | 2.5 | 2.5 |
| Carbopol Ultraze 21 (% w/v) | 2 | 2 | 2 |
| Polyethylene glycol 400 (PEG 400) (% v/v) | 5 | 5 | 10 |
| Propylene glycol (% v/v) | — | 5 | 10 |
| Menthol (% w/w) | 0.5 | 0.5 | 0.5 |
| Isopropyl alcohol (% v/v) | 0.1 | 0.1 | 0.1 |
| DMDM Hydantoin (% v/v) | 0.075 | 0.075 | 0.075 |
| Triethanolamine | q.s | q.s | q.s |
| Distilled water (ml) | 100 | 100 | 100 |

Topical Preparation (Gel)

Topical preparation i.e gel formulation was prepared using Carbopol Ultraze 21.

Initially the gel was prepared using different concentrations of Carbopol Ultraze 21 i.e 1%, 1.5%, 1.75% and 2%.

Among the 4 different gels 2% gel was selected as it was found to have the best consistency and spreadability. Therefore, for the further procedure 2% carbopol gel was selected.

Topical Preparation (Gel)

Physical appearance: The prepared gels were inspected visually for their different physical properties such as: F1, F2, F3

Topical Preparation (Gel)

Color & appearance

The color and appearance of the gel formulations F1, F2 and F3 were visually analyzed.

Homogeneity

All the developed were tested for homogeneity by visual inspection. The were tested for the presence of any aggregates or lumps.

Consistency

It was determined manually by applying on the skin.

Grittiness

The formulated gels i.e F1, F2 and F3 were evaluated for the presence of any gritty particles by applying it on the skin.

Phase Separation

The formulated gels F1, F2 and F3 were observed for any phase separation by visual observation for 1 week.

pH determination: The pH of the prepared gel was determined using a digital pH meter at room temperature. Accurately weighed 2.5 gm of gel was weighed and dispersed in 25 ml of distilled water and then pH meter was dipped in the dispersion. The measurement of pH of the formulated gel was done in triplicate and average values were calculated.

Drug Content determination: 1 gm of gel was dissolved in 50 ml of distilled water. Drug content was determined at 280 nm using UV-visible spectrophotometer and was calculated using the equation obtained by linear regression analysis of calibration curve.

Results:

Physical parameters of the prepared gels:

TABLE 10

Physical parameters of the prepared gels

| Parameters | F1 | F2 | F3 |
|---|---|---|---|
| Color & appearance | Brownish color | Brownish color | Brownish color |
| Homogeneity | Good | Good | Good |
| Phase Separation | No | No | No |
| Grittiness | No | No | No |

Topical Preparation (Gel)
pH and % drug content of the formulations:

TABLE 11

Topical Preparation (gel); pH and % drug content of the formulations

| Formulation | pH | % Drug content |
|---|---|---|
| F1 | 6.7 ± 0.09 | 98.4 ± 0.5 |
| F2 | 6.82 ± 0.04 | 98.9 ± 0.2 |
| F3 | 6.89 ± 0.20 | 99.3 ± 0.4 | n = 3

Topical Preparation (Gel)

In vitro release study by artificial membrane (using cellophane membrane):

The in vitro drug release study is done in two steps:
a) Activation of cellophane membrane
b) In vitro drug release using cellophane membrane carried out in buffer pH 7.4

In Vitro Drug Release Study
a) Activation of cellophane membrane

Cellophane Membrane Specification:

Size: 100/pk Cellophane dimension: 21.6×23.5 cm

Activation Procedure:

The membrane was washed distilled water for 1 hour and soaked in solvent system (phosphate buffer pH 7.4)

b) In vitro drug release study by artificial membrane:

Diffusion studies were carried out by using Franz type diffusion cell for F1 formulation in pH 7.4 phosphate buffer solution. 500 mg of gel (F1) was placed on the cellophane membrane which was then mounted on the Franz diffusion cell. The receptor medium with the pH 7.4 phosphate buffer was maintained at constant temperature of 37° C. The medium was stirred continuously on a magnetic stirrer at 100 rpm. 2 ml of aliquots were withdrawn at present time intervals and replaced by an equal volume of fresh dissolution medium. The samples were then analyzed for using UV-visible method spectrophotometry.

% Cumulative Drug Release is Calculated by Using the Formula:

Concentration×volume of dissolution medium×Dilution Factor×100 Amount of drug (μg)

In vitro drug release study of formulation 1 (F1) using Franz diffusion cell in phosphate buffer pH 7.4

In vitro drug release study

Work to be done

In vitro drug release of formulation F3 and comparative analysis for cream

Permeation studies of the example formulation with comparative analysis for cream through rat skin Evaluation of the example gel formulation:

Determination of viscosity

Determination of spreadability

Determination of extrudability

Evaluation of the gel formulation:

Texture analysis by using texture analyzer

Bio-adhesive strength measurement

Stability studies of the example gel formulation according to the ICH guidelines Preparation of Topical Formulation Gel Gels were prepared by cold mechanical method. Polymer (Carbopol Ultraze 21) was weighed and it was sprinkled slowly on the surface of purified water with continuous stirring for 2 hr.

After which it was stirred continuously by mechanical stirrer, till polymer soaked in the water.

Now Propylene glycol and Polyethylene glycol 400 (PEG 400), which behaves as penetration enhancers and DMDM Hydantoin as preservative was added to the gel, followed by menthol and isopropyl alcohol.

Now the drug 3HX was added to the gel with continuous stirring till drug get dispersed in gel completely.

Finally with continuous stirring, triethanolamine was added to neutralize the gel and it maintains the pH of the gel.

Preparation of Topical Formulation Gel

TABLE 12

Preparation of Topical formulation gel

| Ingredients | F1 | F2 | F3 |
|---|---|---|---|
| Drug (3HX) (gm) | 2.5 | 2.5 | 2.5 |
| Carbopol Ultraze 21 (% w/v) | 2 | 2 | 2 |
| Polyethylene glycol 400 (PEG 400) (% v/v) | 5 | 5 | 10 |
| Propylene glycol (% v/v) | — | 5 | 10 |
| Menthol (% w/v) | 0.05 | 0.05 | 0.05 |
| Isopropyl alcohol (% v/v) | 0.1 | 0.1 | 0.1 |
| DMDM Hydantoin (% v/v) | 0.075 | 0.075 | 0.075 |
| Triethanolamine | q.s | q.s | q.s |
| Distilled water (ml) | 100 | 100 | 100 |

In-Vitro Drug Release Study

TABLE 13

In-vitro drug release study (Time (hrs) and % Cumulative release)

| Time (hrs) | % Cumulative release |
|---|---|
| 0.25 | 5.011 |
| 0.5 | 8.034 |
| 1 | 19.27 |

TABLE 13-continued

In-vitro drug release study (Time (hrs) and % Cumulative release)

| Time (hrs) | % Cumulative release |
|---|---|
| 2 | 24.76 |
| 4 | 33.23 |
| 8 | 45.99 |
| 12 | 58.56 |
| 18 | 64.89 |
| 24 | 75.54 |

Figure 16A:
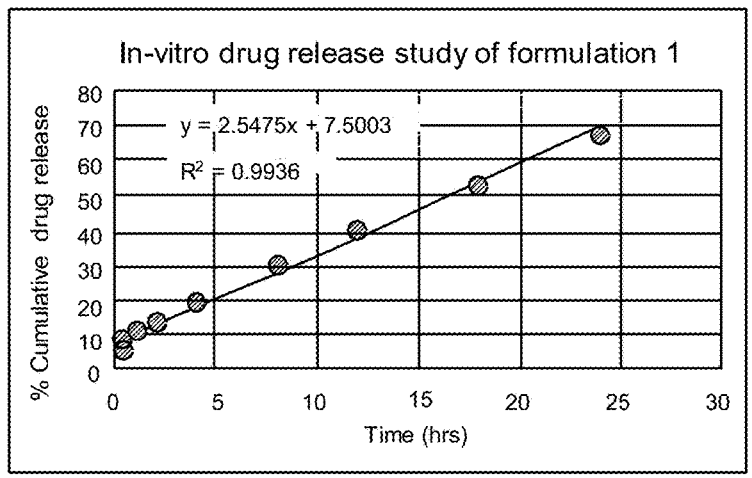
FIG. 16A: In vitro drug release study of Formulation 1
Figure 16B:
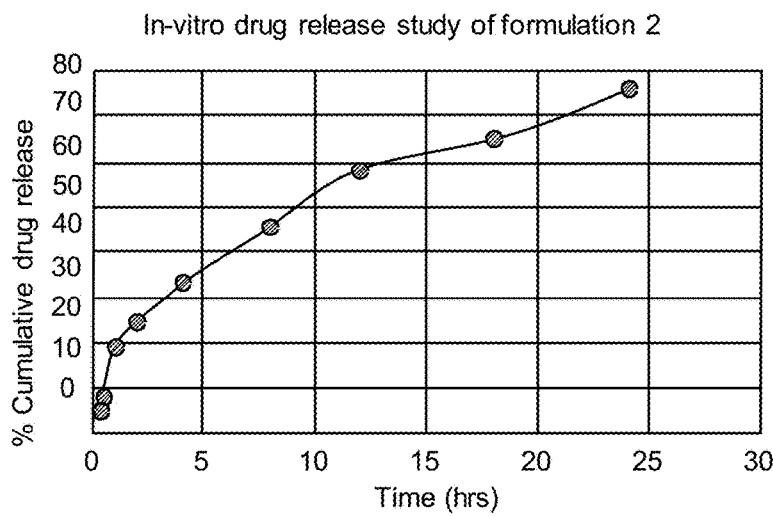
FIG. 16B: In vitro drug release study of Formulation 2
Figure 16C:
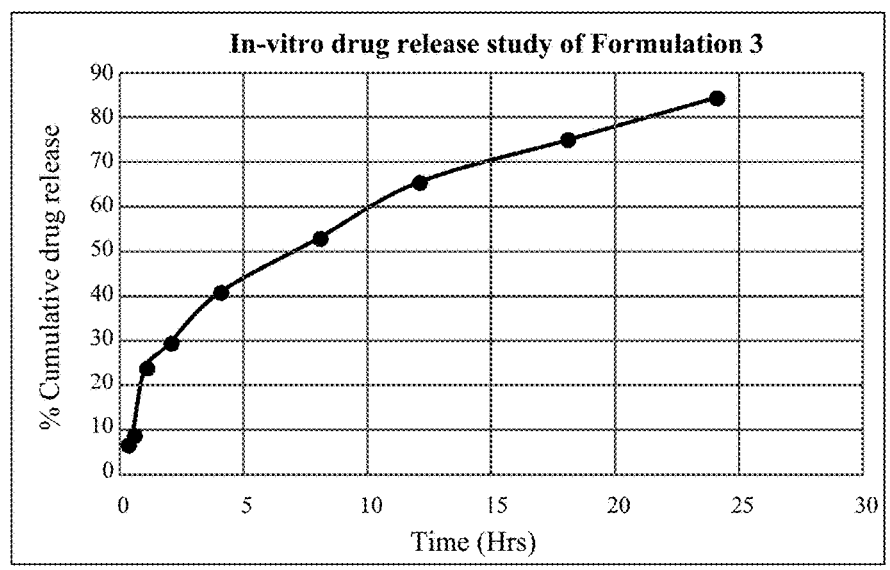
FIG. 16C: In vitro drug release study of Formulation 3
Figure 17A:
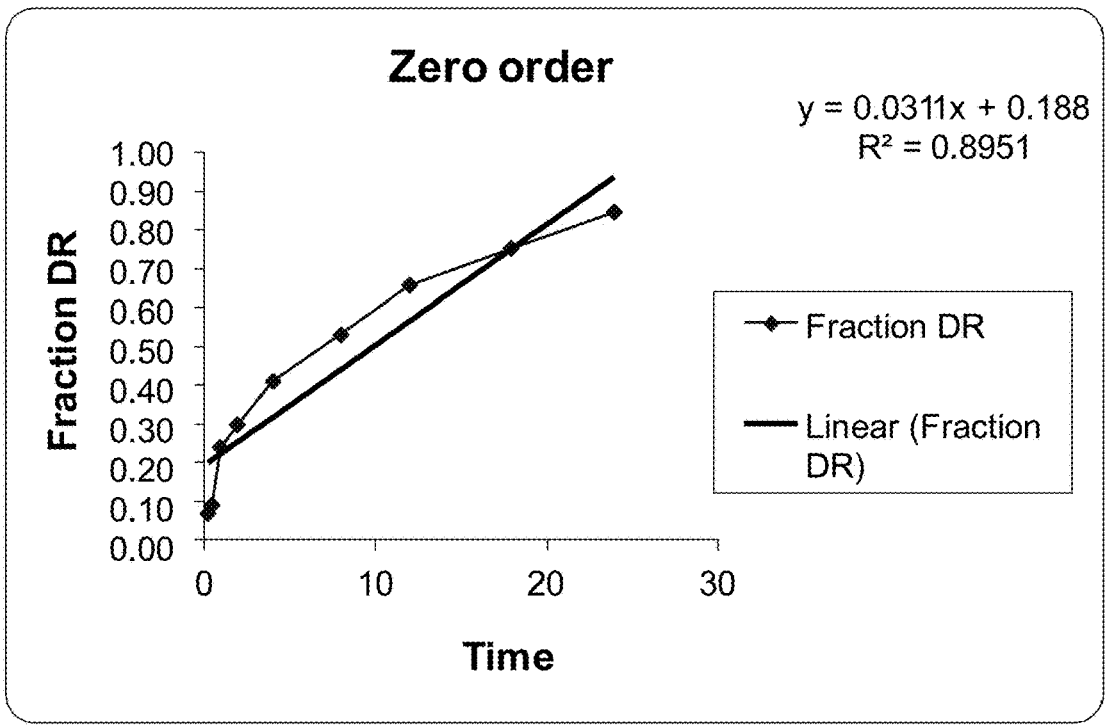
FIGS. 17A-17E: —In-vitro release kinetics model
Figure 17B:
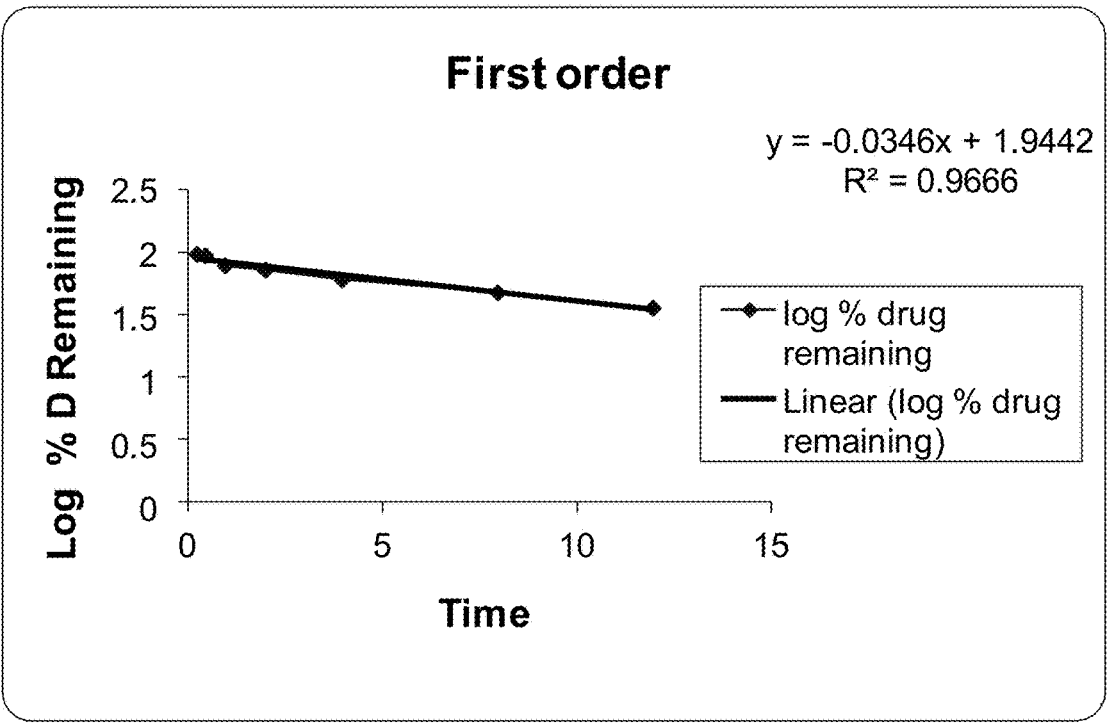
Figure 17C:
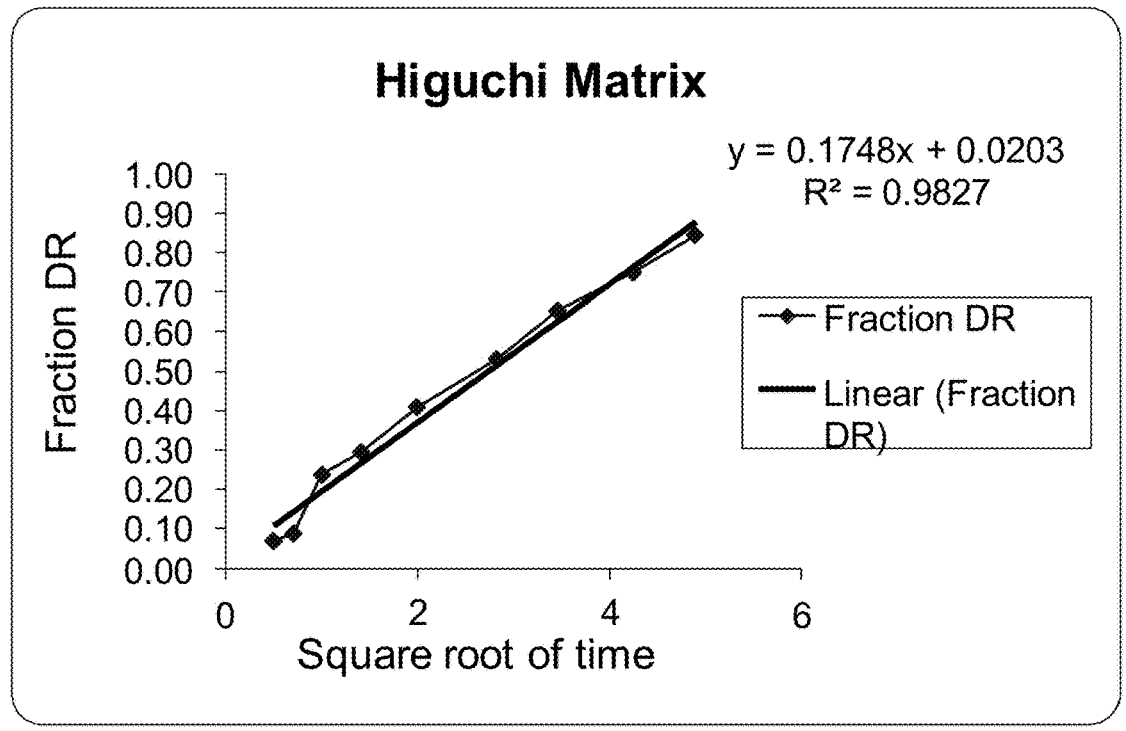
Figure 17D:
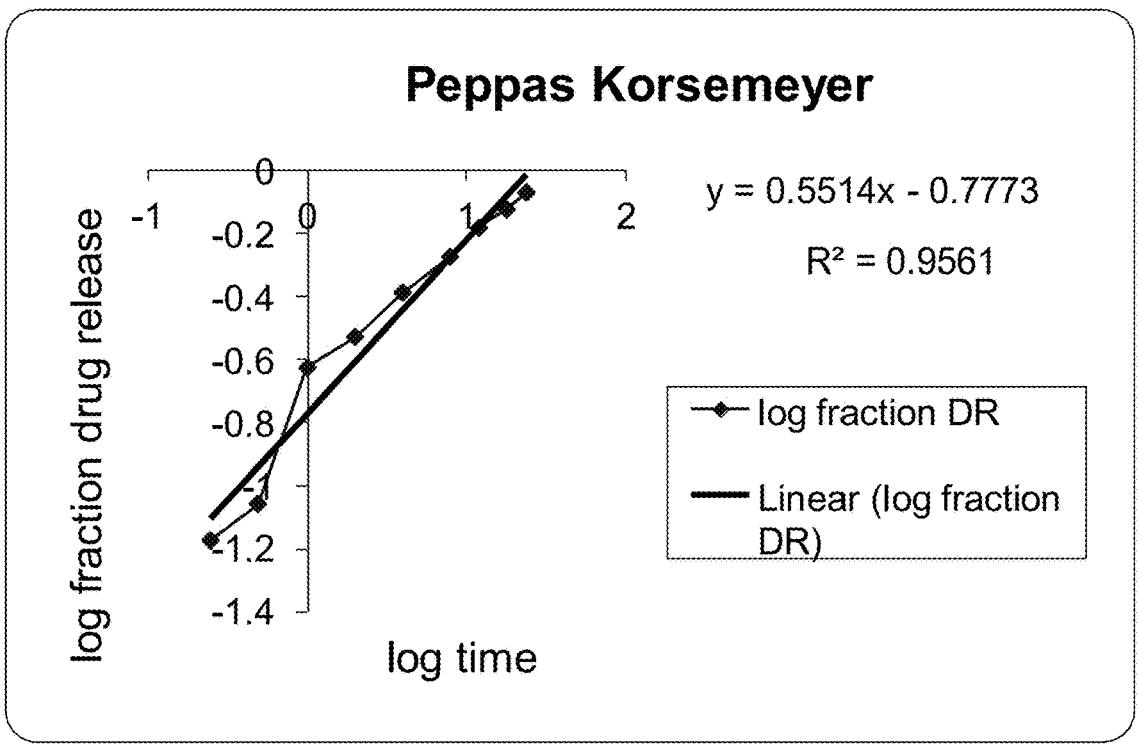
Figure 17E:
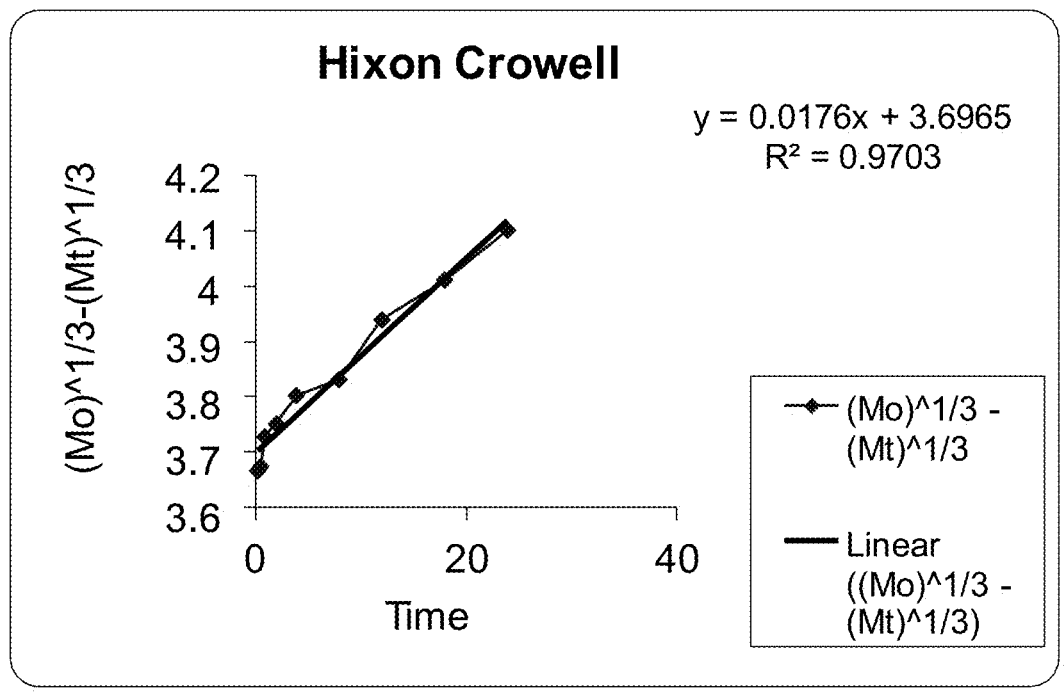

FIG. 16B: In vitro drug release study of Formulation 2

In-Vitro Drug Release Study

TABLE 14

In-vitro drug release study (Time (hrs) and % Cumulative release)

| Time (hrs) | % Cumulative release |
|---|---|
| 0.25 | 6.66 |
| 0.5 | 8.68 |
| 1 | 23.68 |
| 2 | 29.34 |
| 4 | 40.67 |
| 8 | 52.89 |
| 12 | 65.31 |
| 18 | 74.78 |
| 24 | 84.23 |

In-Vitro Release Kinetics Model

| Model | R2 |
|---|---|
| Zero Order | 0.8951 |
| First Order | 0.9666 |
| Higuchi | 0.9827 |
| Peppas Kors | 0.9561 |
| Hixon Crowell | 0.9703 |

In-Vitro Drug Release Study Outcomes

On the basis of in-vitro drug release study of formulation F1, F2 and F3 the release profile of F3 was found to be best.

The amount of the drug released was incorporated into various release kinetic models as Zero order model, first-order model, Higuchi model, Hixcon-Crowell model and Korsmeyer—Peppas model, among them the best fit model was determined on the basis of regression co-efficient ($R^2$) value.

The observed best fit model was Higuchi model followed by First order release model with $R^2$ 0. 0.9827 and 0.9666 respectively.

Therefore, for the further evaluation formulation F3 was selected.

Evaluation of the example formulation (F3)

Determination of viscosity

Determination of extrudability

Texture analysis by using texture analyzer

Bio-adhesive strength measurement

Evaluation of the example formulation (F3)

Determination of viscosity

The viscosity of the example formulation (F3) was measured using rheometer (MCR 101. Rheoplus, Anton Paar India Pvt. Ltd., India). It was done by using cone plate probe and carried out for 6 seconds.

Evaluation of the Example Formulation (F3)

Determination of Extrudability

It is test to measure the force to extrude the gel from the tube.

On application of weight, the amount of gel extruded from the aluminium tube was determined. The gel extruded should be at least 0.5 cm ribbon in 10 s.

More quantity of gel extruded better is extrudability. The extrudability of the example formulation was measured in triplicate.

Evaluation of the Example Formulation (F3)

Texture analysis by using texture analyzer (Tensile strength measurement)

Tensile strength of the gel was determined by using TA.XT2 texture analyzer (Stable Micro Systems, Goldalming, UK).

The mechanical properties have been assessed using the texture analyzer with a load of 5 kg loaded cell. Data acquisition and mathematical was done using Texture Expert® software.

Cohesiveness, firmness and consistency were determined for the example formulation (F3).

Texture analysis by using texture analyzer (Tensile strength measurement)

Evaluation of the example formulation (F3)

Bio-Adhesive Strength Measurement

Bio-adhesion measurement was done by means of a tensile test, which indicates the gel bio-adhesive potential.

The maximum force for detaching a piece of skin from gel, after an initial period of the contact was determined.

The forces involved in the process were measured by texture analyzer.

Average maximum positive force (adhesiveness) was determined for the example gel formulation (F3).

Evaluation of the Example Formulation (F3)

T.A Settings

TABLE 15

Evaluation of the example formulation (F3); T.A Settings

| | |
|---|---|
| Pre test speed | 0.5 mm/s |
| Test speed | 1.0 mm/s |
| Post test speed | 10.0 mm/s |
| Force | 500 g |
| Time | 1.0 s |
| Distance | 3 mm |
| Trigger type | Auto-5 kg |
| Tare mode | Auto |
| Data Acquisition Rate | 500 pps |

Evaluation of the Example Formulation (F3)

Bio-adhesive strength measurement

Sample was placed on the blank plate of Heavy Duty Plate. A holed plate is then placed on top of the sample, central to the probe, allowing passage.

This plate provides weight around the test region to prevent lifting of the sample when the probe is withdrawn, hence avoiding stickiness.

The adhesive test is then commenced. The probe should be cleaned between the tests.

Evaluation of the Example Formulation (F3)

Bio-adhesive strength measurement

Figure 18A:
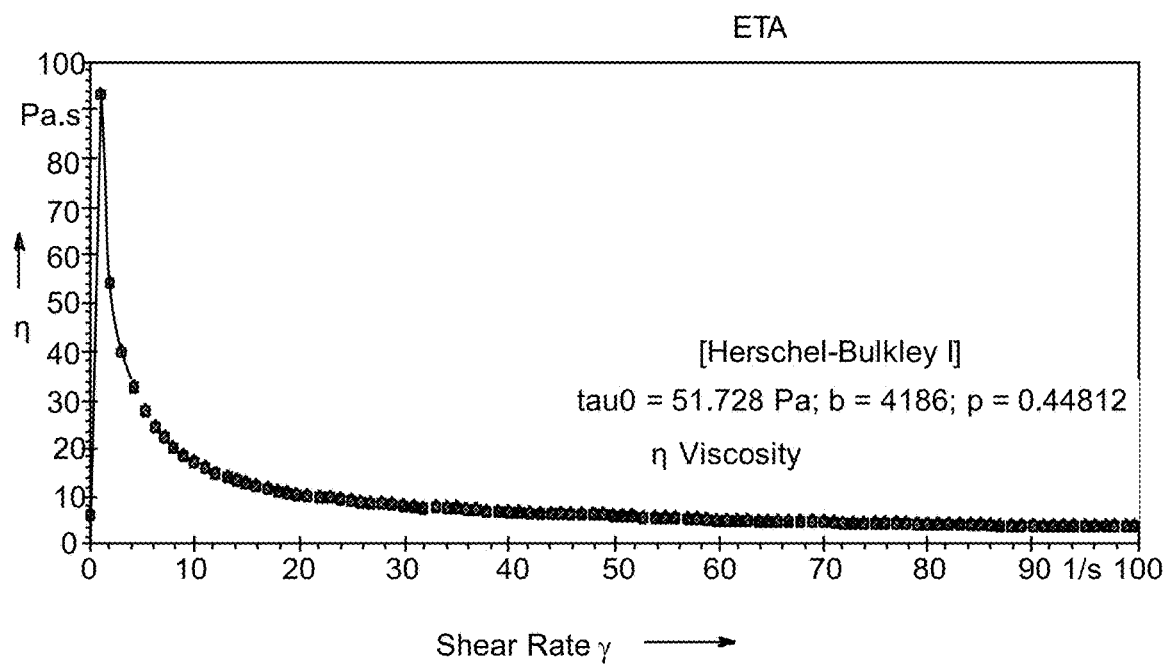
FIGS. 18A-18C: Evaluation of the example formulation (F3); RESULTS, Viscosity
Figure 18B:
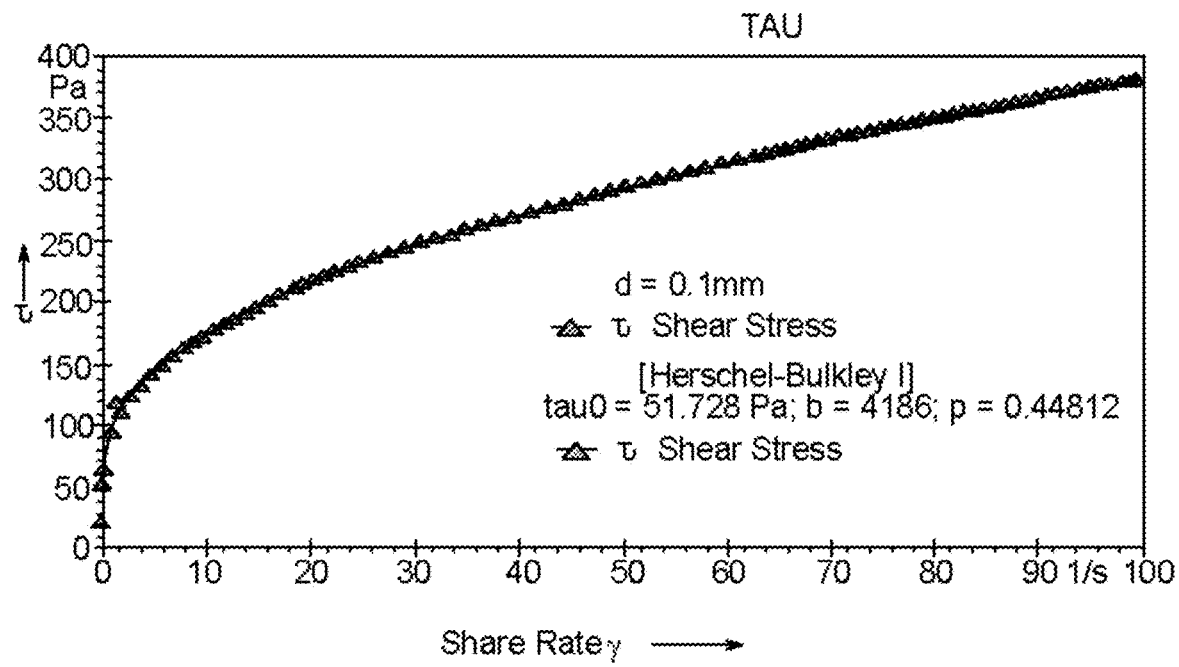
Figure 18C:
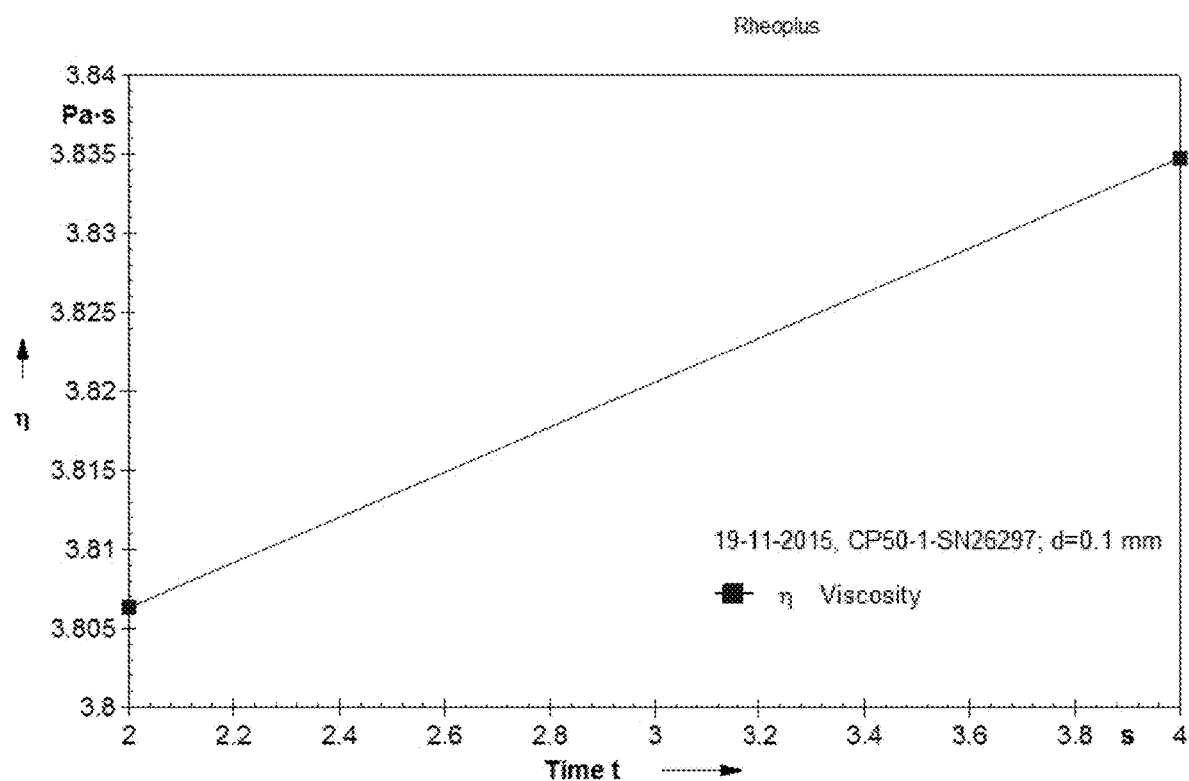

FIGS. 18A-18C: Evaluation of the example formulation (F3); RESULTS, Viscosity

Evaluation of the Example Formulation (F3)

Viscosity

The viscosity of the example formulation F3 was found to be 3830 cP.

Extrudability

The extrudability of the example formulation F3 was found to be 1.5±0.65 (g/cm2)

Evaluation of the Example Formulation (F3)

Texture Analysis

TABLE 16

Evaluation of the example formulation (F3); Texture analysis

| Texture profile | Gel |
|---|---|
| Firmness (g) | 0.8 * 1000 |
| Consistency (gs) | 0.45 * 1000 |
| Cohesiveness (−value) (g) | −0.8 * 1000 |

Figure 19A:
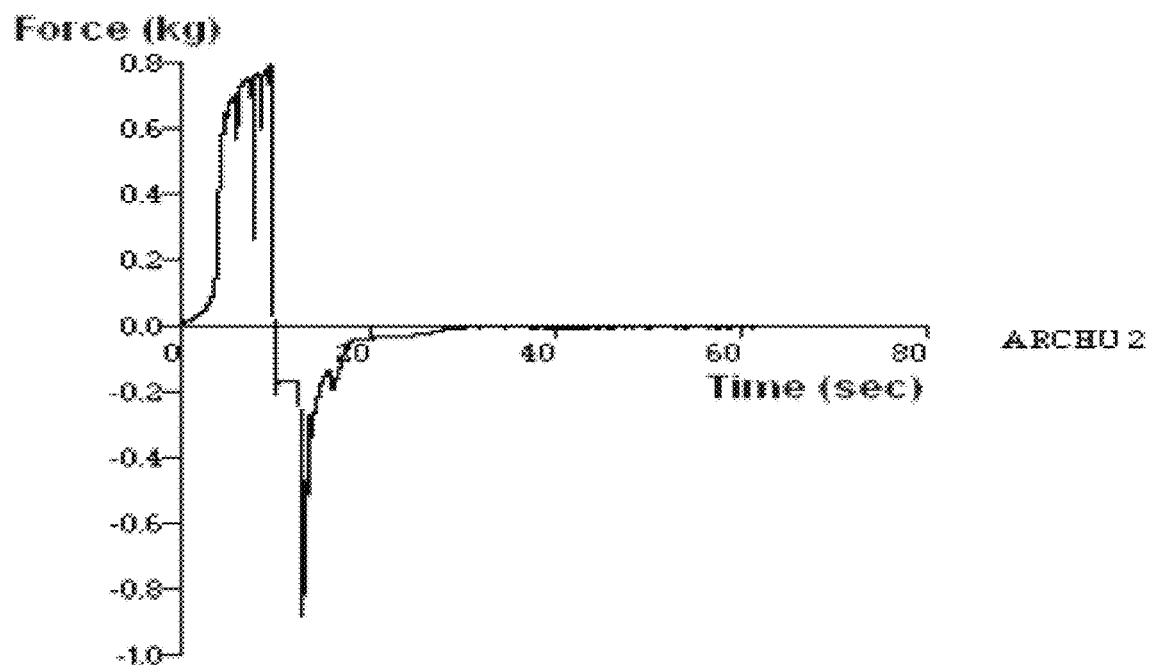
Figure 19B:
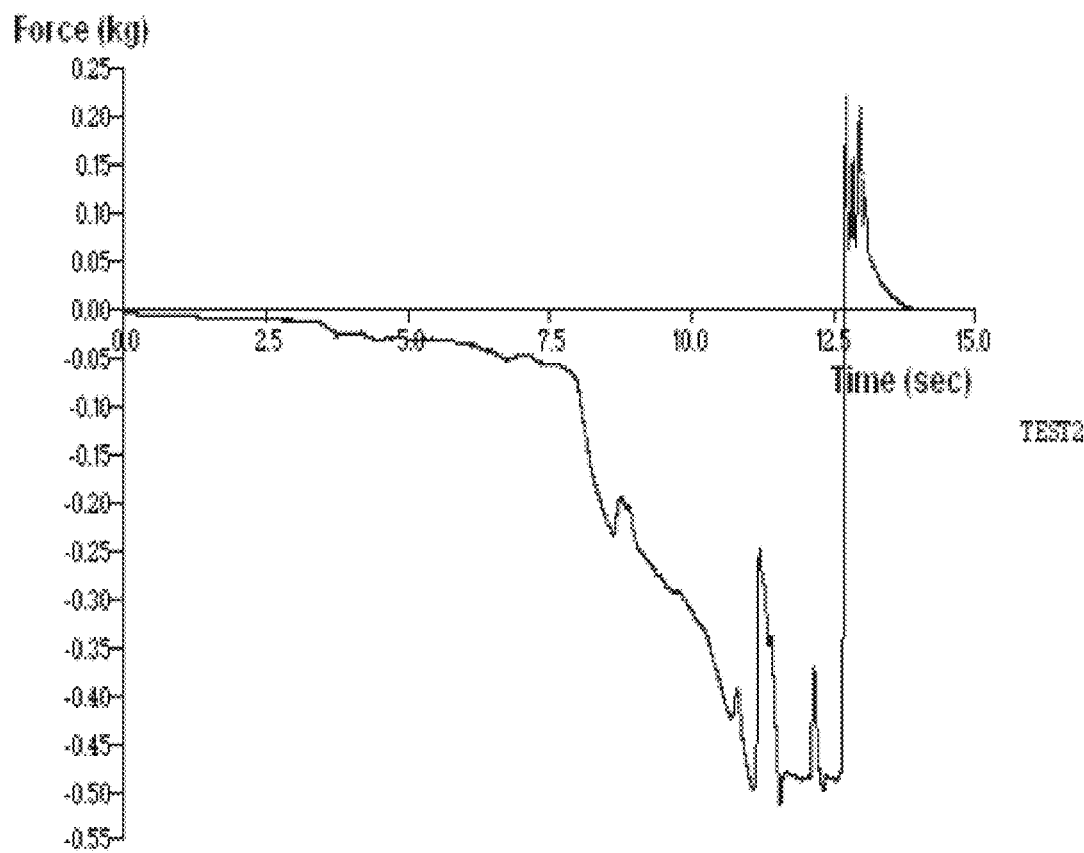
FIG. 19B: Bio-adhesive strength measurement

FIG. 19B: Bio-adhesive strength measurement

The Mean Maximum Positive Force "Adhesiveness" (g)=22.4±0.85

Work to be Done

In vitro drug release of formulation F3 and comparative analysis for cream

Figure 20:
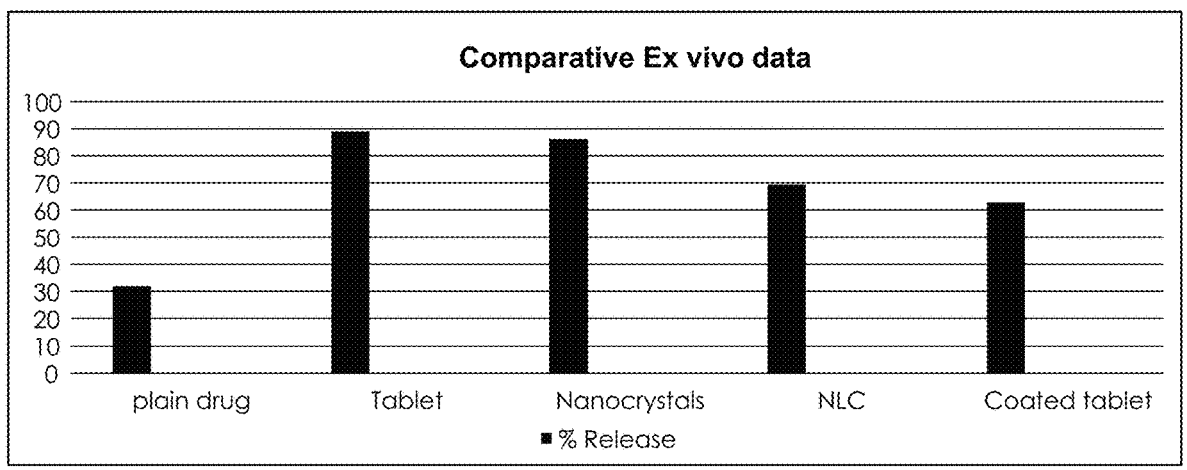
FIG. 20: Oral Formulation; Ex-Vivo Drug Release Studies; Comparative Ex vivo data

Permeation studies of the example formulation with comparative analysis for cream through rat skin Stability studies of the example gel formulation according to the ICH guidelines Oral Formulation Ex-Vivo Drug Release Studies FIG. 20: Comparative Ex vivo data About Coated Tablets Retarded Dissolution Has Been Recorded The Apparent Permeability Coefficient Value Has Been Found To Be Very Low As Compared To The Prepared Formulations.

Drug Loading Studies

TABLE 17

Drug Loading Studies

| FORMULATION | % DRUG LODING |
|---|---|
| Nanocrystal | 86.56% |
| Nano Structured Lipid Carrier | 61.22% |

These studies were performed by taking about 2 ml of each formulation and centrifuging them at 10,000 rpm for 15 mins.

Thereafter the supernatant was collected and analysed by developed UV method of analysis.

Interaction Studies

These were performed using differential scanning calorimetry.

Melting point of pure drug 3 HX was found to be 180.789 degree Celsius.

The peak for pure drug has shifted in both the nanocrystals and NLC

The peaks obtained in case of nanocrystal is sharp and prominent indicating effective incorporation of drug.

Similar is the case with NLC.

Figure 21A:
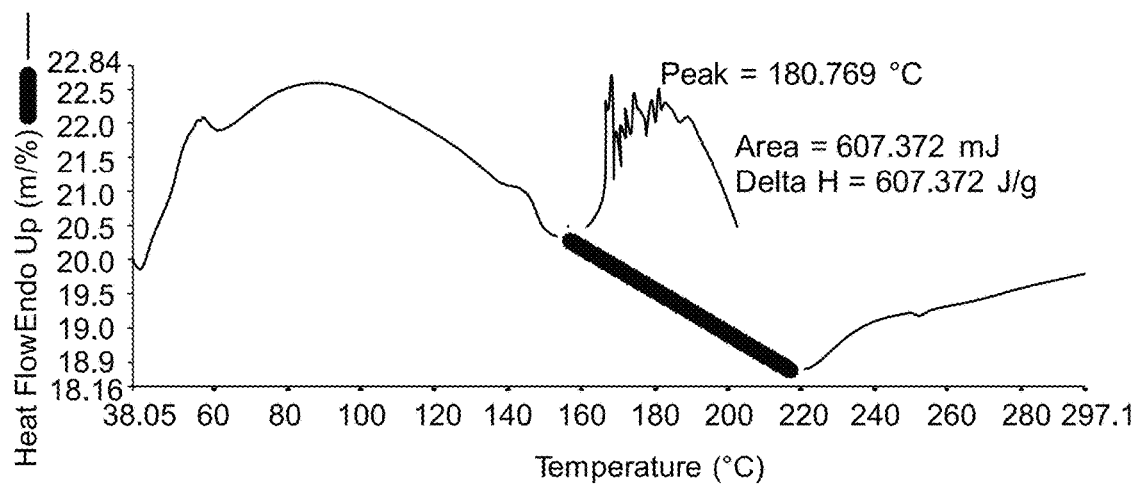
FIG. 21A: DSC curve for Drug 3HX

FIG. 21A: DSC curve for Drug 3HX

Figure 21B:
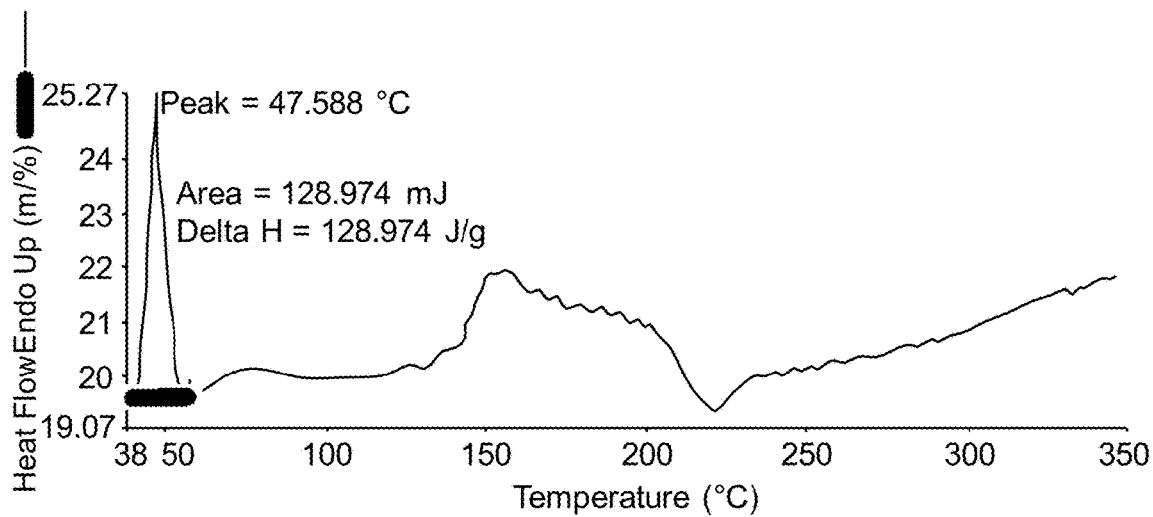
FIG. 21B: DSC curve for Nanocrystals

FIG. 21B: DSC curve for Nanocrystals

Figure 21C:
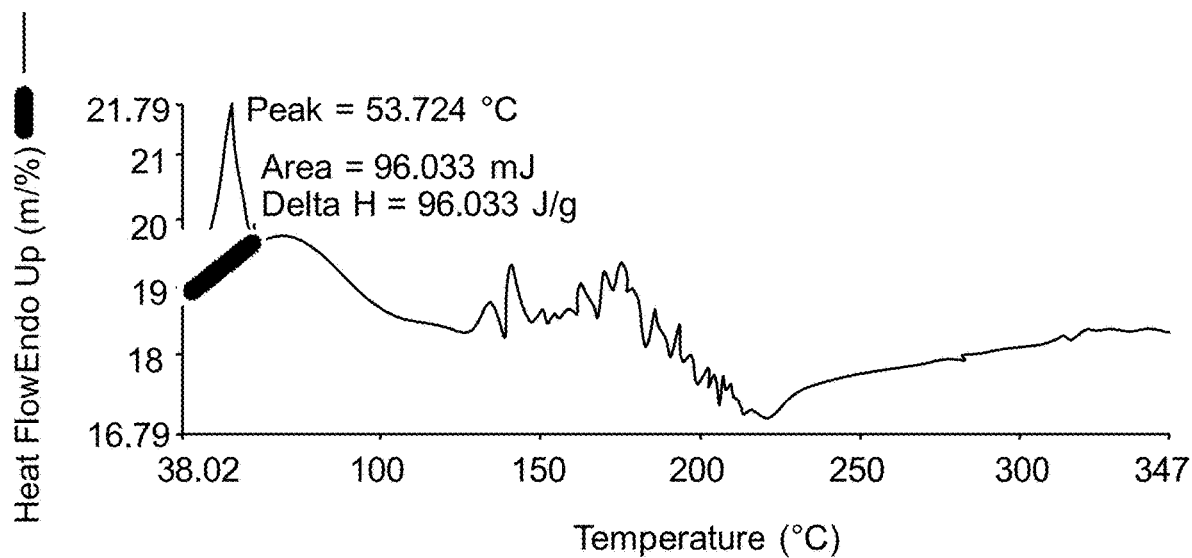
FIG. 21C: DSC curve for NLC

FIG. 21C: DSC curve for NLC

Figure 22A:
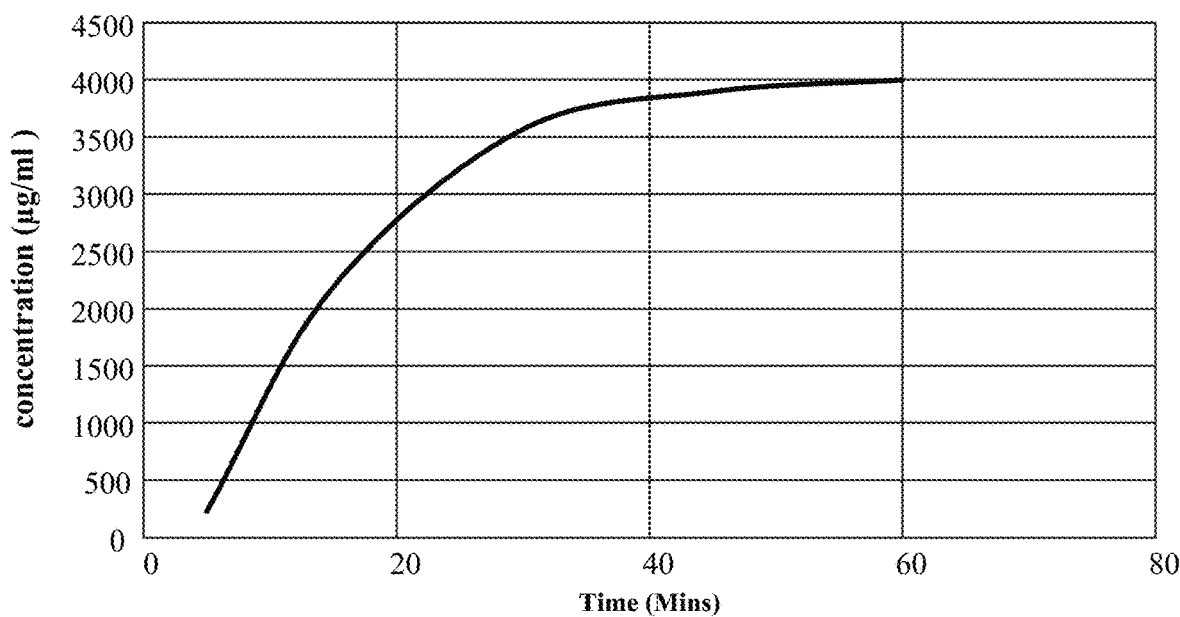
FIG. 22A: Dissolution Profile of 3HX

FIG. 22A: Dissolution Profile of 3HX

Figure 22B:
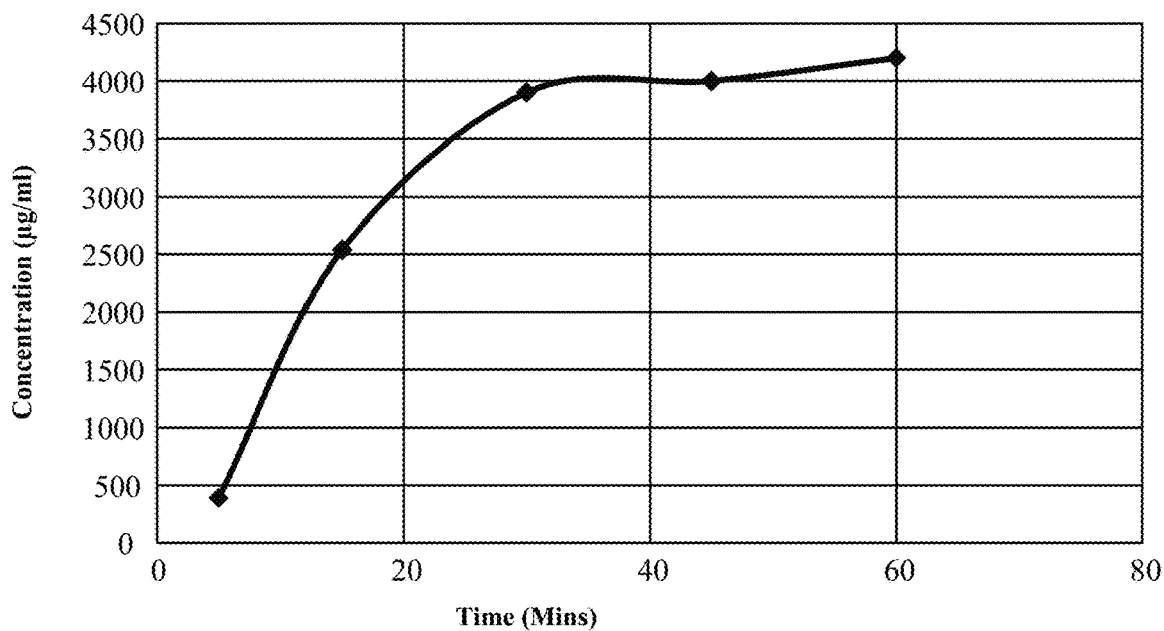
FIG. 22B: Dissolution Profile Of Nanocrystals

FIG. 22B: Dissolution Profile Of Nanocrystals

Figure 23B:
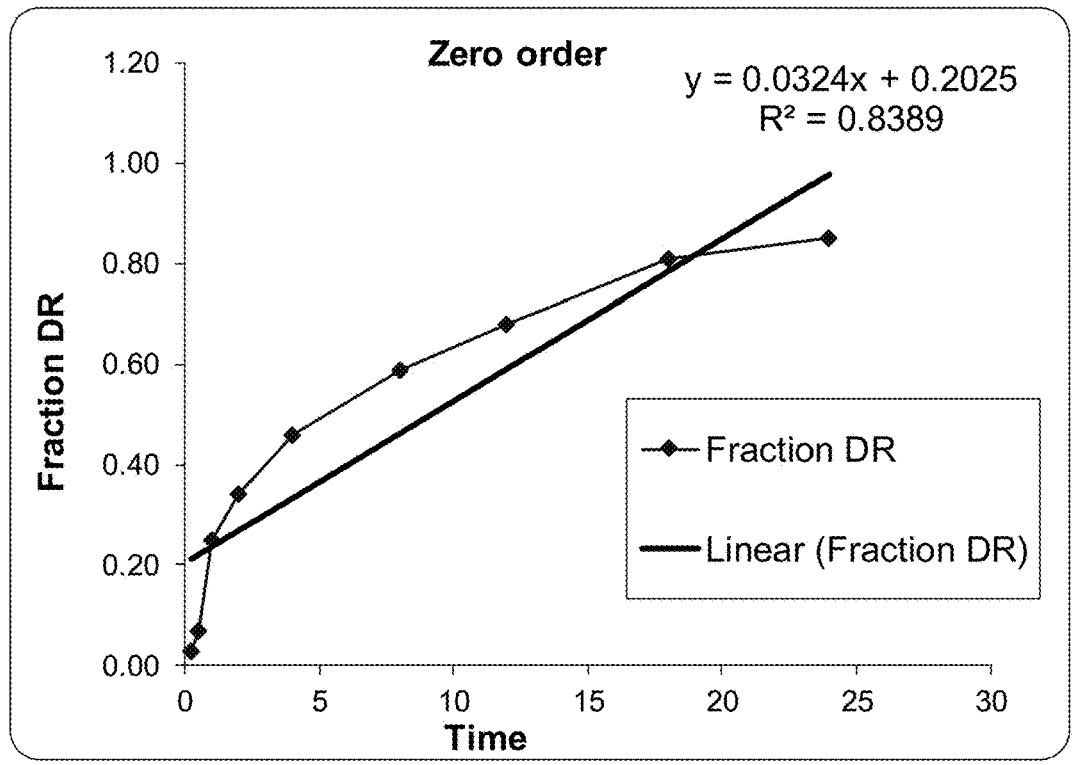
FIG. 23B: Higuchi Matrix

FIG. 23B: Higuchi Matrix

Figure 23C:
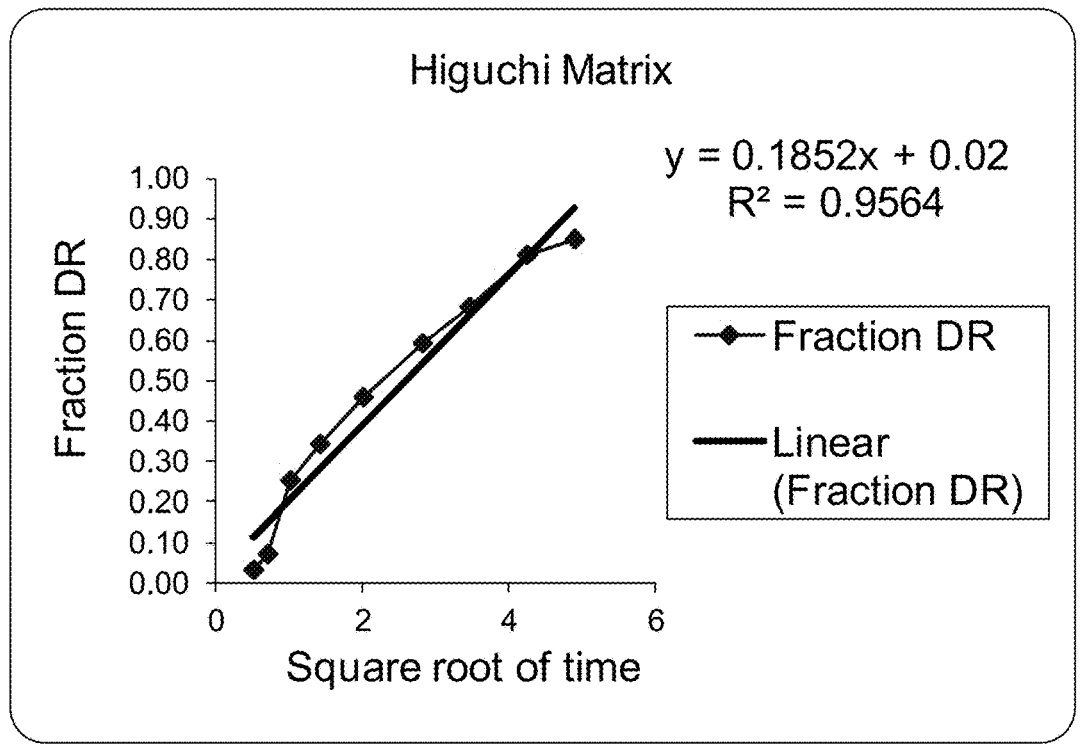
FIG. 23C: Peppas Korsemeyer

FIG. 23C: Peppas Korsemeyer

Figure 23D:
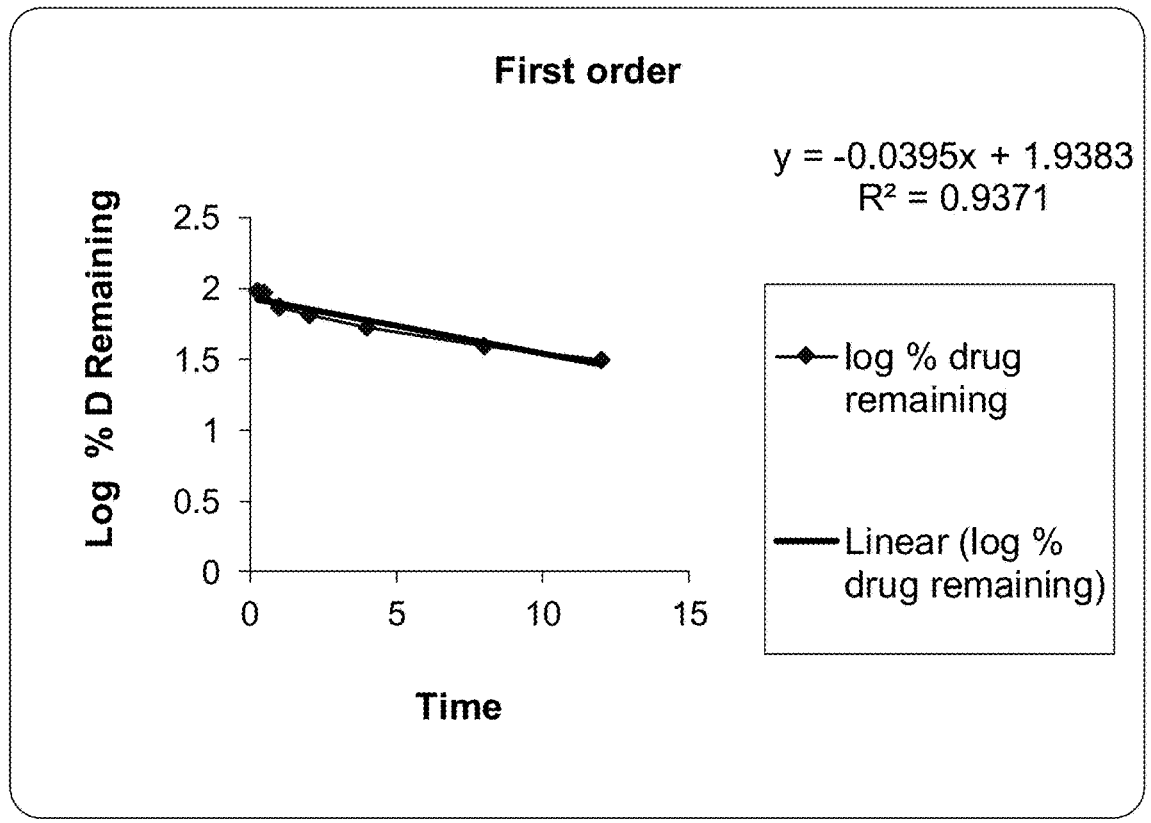
FIG. 23D: First order

FIG. 23D: First order

Figure 23E:
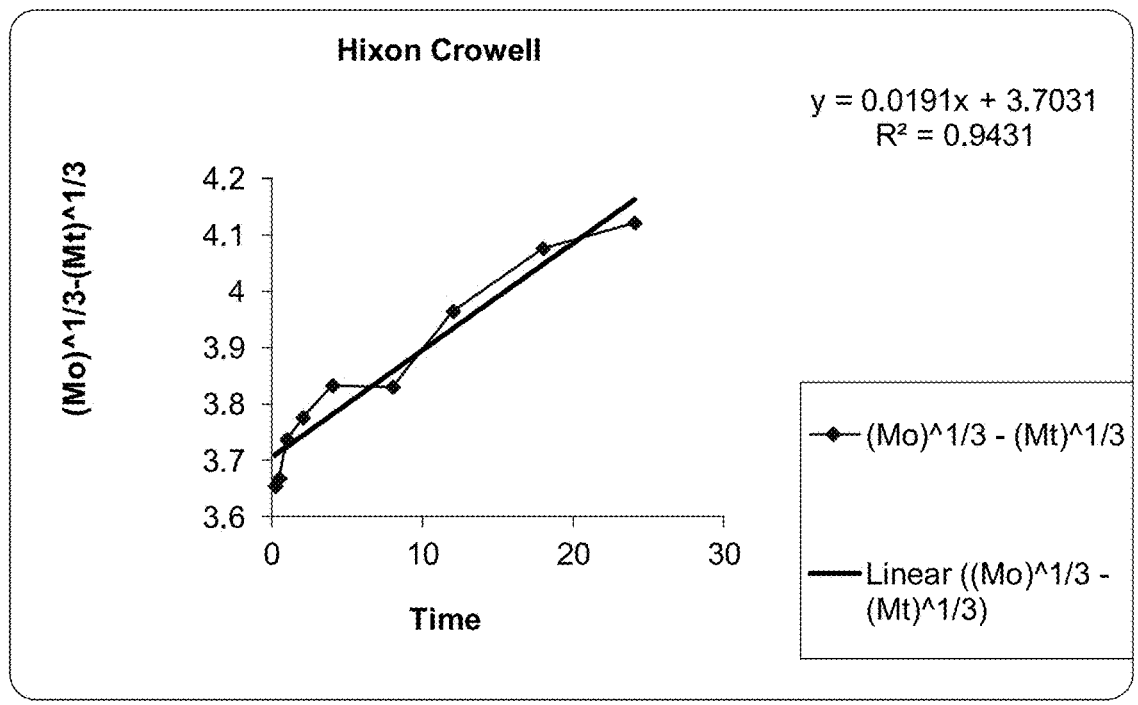
FIG. 23E: Hixon Crowell
FIGS. 24A-24B schematically illustrate example steps in a cooking process in accordance with certain embodiments.
Figure 24A:
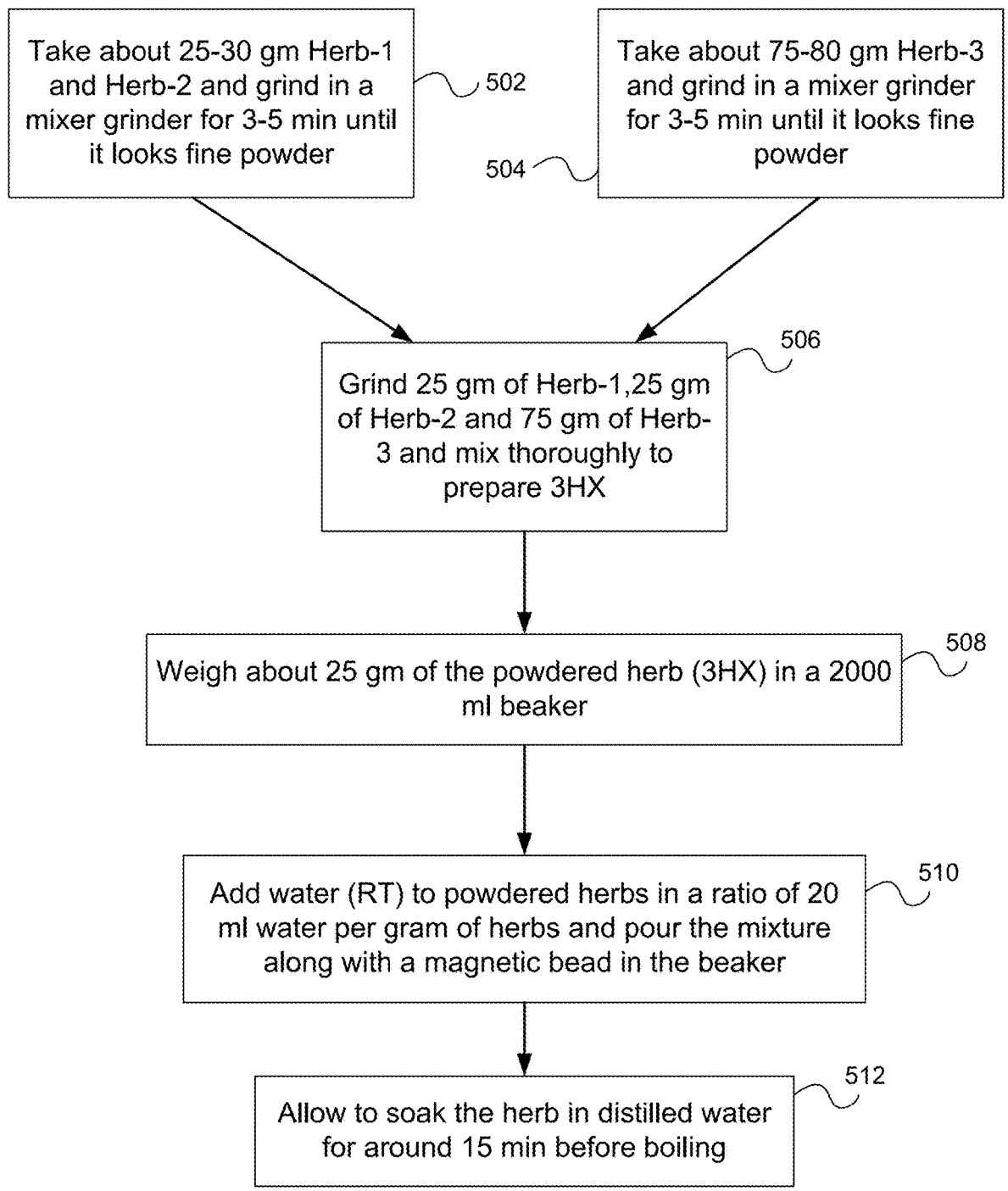
Figure 24B:
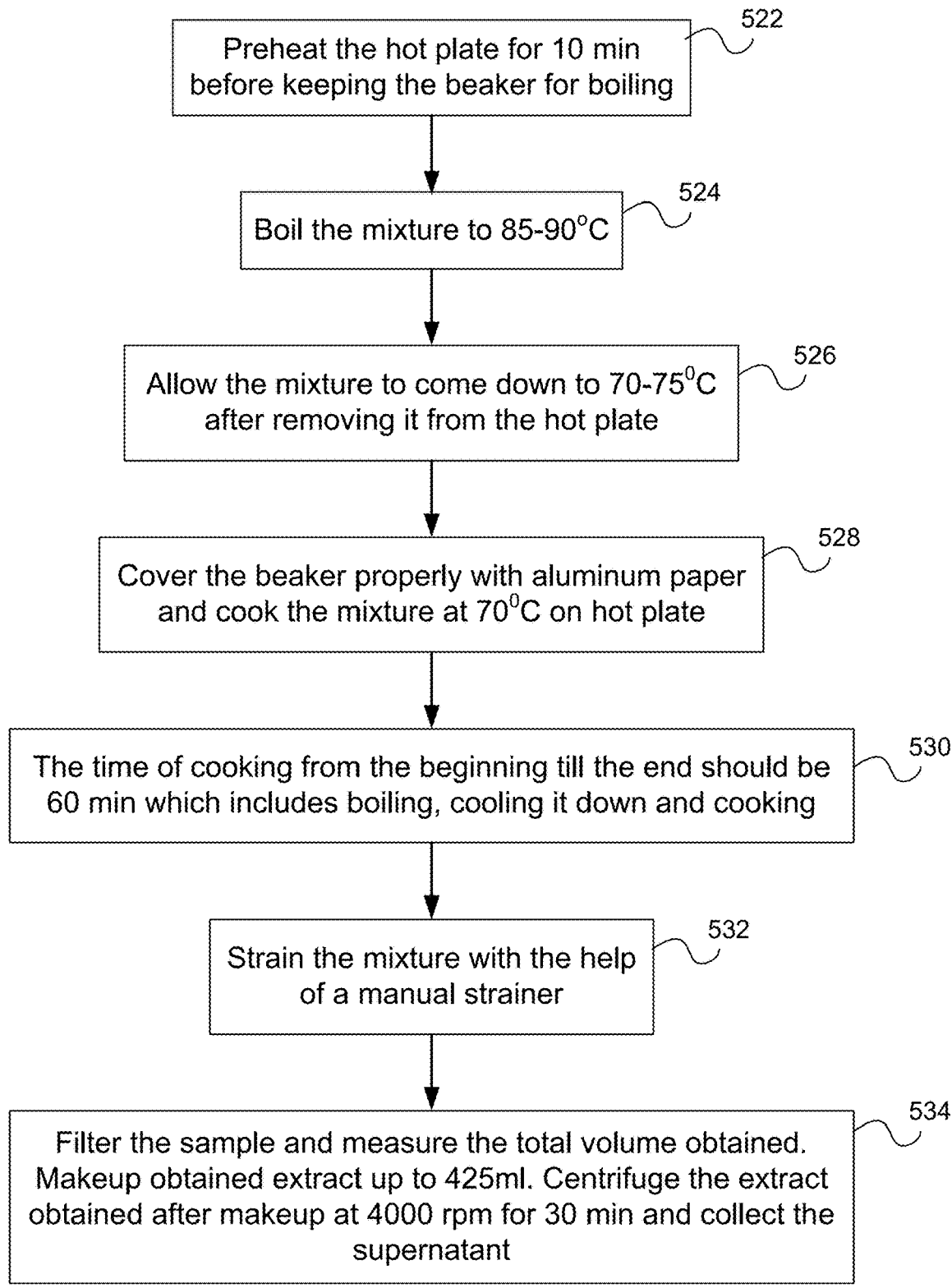
Figure 25:
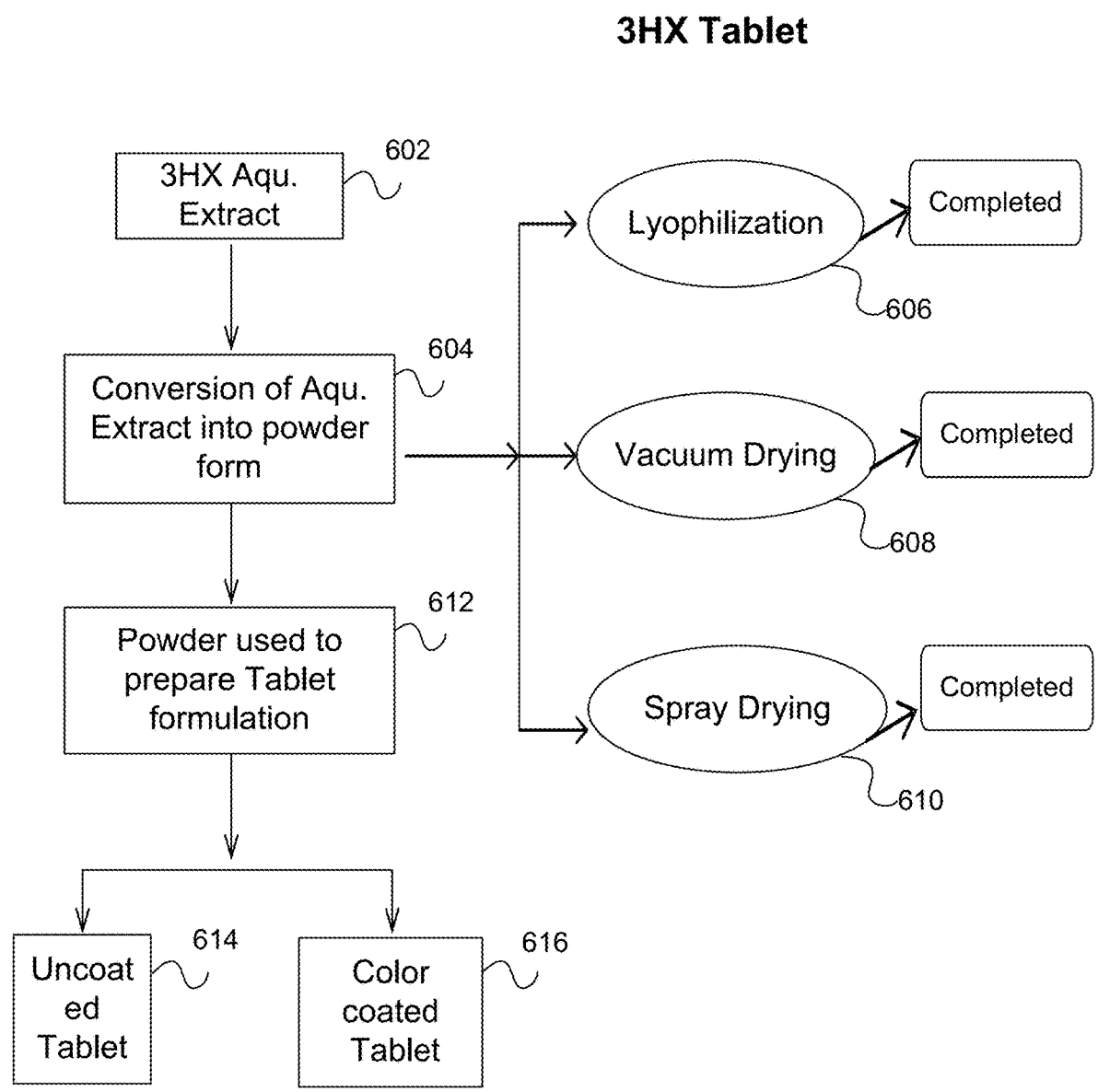
FIG. 25 schematically illustrates example steps on a tablet formulation process in accordance with certain embodiments.
Figure 26:
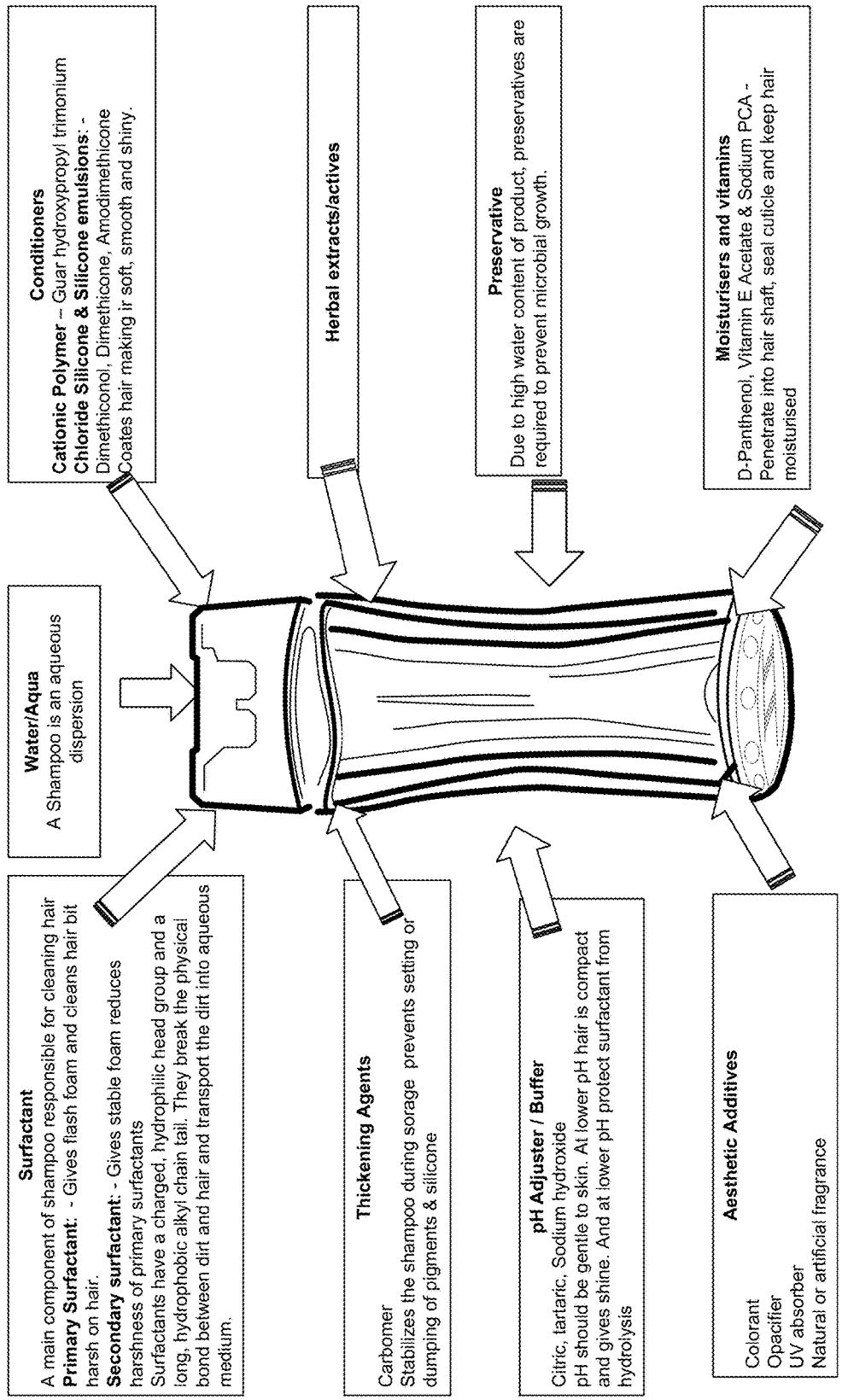
FIG. 26 illustrates the components of a shampoo in accordance with certain embodiments.

FIG. 23E: Hixon Crowell

Stability Studies

All the samples were stored at different temp conditions. They are required to be submitted for HPLC studies.

Samples at various pre-determined intervals have been collected.

Organoleptic Evaluation

TABLE 18

Organoleptic evaluation

| Parameters | Results |
|---|---|
| Colour | Brown |
| Odour | Distinct, As That Of Extract |
| Hygroscopicity | Not Hygroscopic As That Of Extract |
| Texture | Smooth |

Nanogel Formulation and Method of Preparing a Nanogel

A nanogel, nanochrystals and/or another nano-particulate formulation is provided in accordance with certain embodiments, as are methods of preparing such nano-particulate formulation and methods of treating certain conditions with an herbal nano-particulate combination including da huang, sheng di huang or jin yin hua, or combinations thereof, alone or in combination with one or more known or discovered medicines, e.g., one or more of the known medicines for treatment one or more of the conditions described herein.

A nano-particulate preparation process may include grinding and/or homogenizing to reduce the particle size of the herbal mixture to approximately 500 nm average particle size or lower. In certain embodiments, grinding and/or homogenizing may include Dyno milling, e.g., run once to reduce the herbal mixture particulate size to an average 250 nm particle size or lower, or run multiple times to reduce the herbal mixture particulate size to approximately an average 150 nm particle size or lower.

A high pressure homogenizer may be used. The mixture may be pushed through a filter, e.g., 0.2 μm or 0.1-0.3 μm or 0.1-0.4 μm or 0.15-0.3 μm or 0.15-0.4 μm).

The process may include sonication. A step in the process of formulating a nano-particulate mixture may include utilizing ultrasound.

A cooking process may be performed before or after the nano-particulate mixture is prepared that includes Da Huang, Sheng di Huang or Jin Yin Hua, or combinations thereof, in accordance with certain embodiments.

A straining process may be performed to get an aqueous extract. Note that there is a limit on the volume of extract that can be tolerated by a human patient for administration of medicine and/or a medicinal supplement.

A process of preparing a nano-particulate mixture may include lyophilization or freeze drying. For preparation of in vitro formulations, DMSO may be used, but not for in vivo formulations because of the toxicity of DMSO in animals and humans.

A process of preparing a nano-particulate mixture in certain embodiments may include solubilization and/or selection of a concentration of extract. The process may include formulation of a cream, lotion, gel, shampoo, tablet, capsule, nano-lipid carrier, nanogel, nano-chystals, nano-particulates, patch, IV or subdermal formulation or other formulation described herein or as understood by those skilled in the art for administering medicine and/or medicinal supplements to a patient.

Example Nanogel/Nano-Particulate Topical Formulation

An example nanogel formulation may include 1-20%, or or 1-15%, 1-10%, or 2.5-10% or 2.5-5% or approximately 2.5% or approximately 5% of an herbal mixture that includes Da Huang, Sheng Di Huang or Jin Yin Hua or combinations thereof. An example nanogel formulation in accordance with certain embodiments may include fulvic acid, e.g., up to 1-10% or 2.5-10% or 2.5-5% or 1-5% or 5-10%.

An example nanogel or nano-particulate lotion, cream, ointment or shampoo formulation may include carbopol ultraze 21/polymer surfactant. Triethanolomine may be advantageously used to convert lotion to gel and/or to neutralize a level of ph to between 5-8, 5.5-7.5 or 6-7 for topical application.

Propylene glycol and/or polyethylene glycol may be included in a nanogel or other nano-particulate topical formulation, e.g., each 0%-15% each or 5%-10% each, or up to 15% total, or up to 20% total or up to a concentration level wherein spreadability may begin to become too low depending on other ingredients and topical administration considerations.

An example nanogel or other nano-particulate topical formulation may include DMDM Hydantoin.

A nano-liquid carrier may be included in a nano-particulate topical formulation in accordance with certain embodiments, e.g., stearic acid. The nano-particulate topical formulation may be lyophilized and homogenized with a dynomill, not exceeding a lipid limit, in an example embodiment.

Certain embodiments specifically do not include any parabins nor benzoid, as these have been deemed capable of effecting long term toxicity issues in certain patients or in a certain percentage of patients.

Hydrophyllic capacity is advantageously taken into account in certain embodiments such that permeability is greatly enhanced in a nanogel or other nano-particulate topical formulation including less than 450 nm particulates.

An example nano-particulate tablet formulation may include piperine, e.g., 1-10% or 2.5-10%, or 5-10% or 1-5% or 2.5-5%. A tablet formulation may be hardened above 40° C.-50° C. A nano-particulate tablet formulation may be reduced in size for ease of oral administration due to the enhanced permeability of nano-particulates compared with larger particulate sizes, e.g., above 450 nm. The permeability may be increased, e.g., from 10-20% to 20-80% or 30-70% or 40-60% or 50-60% and nano-particulates in accordance with certain embodiments advantageously may be packed stably into tablets of smaller sizes.

A nanogel or other nano-particulate topical formulation may include 1-20% or 1-15% or 1-10% or 2.5-10% or 2.5%-5% of the nano-particulate mixture. Nano-particulates may be 150-450 nm or 150-350 nm or 150-250 nm, or 100-300 nm or 100-400 nm or 100-450 nm or 50-450 nm, which serve to administer more of the medicine or medicinal supplement to a patient than the 10-20% permeability or lower of example formulations having 450 nm and above particulate sizes, because of reduced cumulative dose toxicities, better stability, and enhancement of treatment for the patient regarding tolerance and saturation issues.

A nano-emulsion, which tends to be oily, may include 100 nm or less particulate sizes. Treatment methods and medicinal compositions are provided for treating eczema, and other skin conditions. Certain embodiments involve the use of herbal combinations and combinations of certain herbs, certain herbal extracts and/or certain molecular components of certain herbs, alone or in combination with or supplemental to one or more other known or novel or experimental treatments. Certain embodiments are formulated as a shampoo, conditioner, cream, ointment or other topical scalp or hair treatment.

Methods and medicinal compositions are provided to treat eczema, and/or other skin conditions such as psoriasis, psoriatic arthritis, or other inflammatory skin disorders, dandruff including seborreic dandruff, seborrhea, acne, burns, dermatitis including atopic dermatitis, warts, keratosis, acne, alopecia, hirsutism or capitis, melanoma or non-melanoma skin cancer, basal cell cancer (BCC), squamous cell cancer (SCC), scleroderma, dermatofibrosarcoma protuberans, Merkel cell carcinoma, Kaposi's sarcoma, capuche sarcoma, keratoacanthoma, spindle cell tumors, sebaceous carcinomas, microcystic adnexal carcinoma, Paget's disease of the breast, atypical fibroxanthoma, leiomyosarcoma, and angiosarcoma, Marjolin's ulcers, kidney failure, nerve damage caused by a skin condition, or skin burrowing mites, or warts or burns, or another skin ailment, lesion or sore, particularly of the scalp and also for other skin regions affected by an ailment that is susceptible to topical or hair treatment, as well as hair fall or hair loss conditions.

In certain embodiments, herbs are advantageously combined as herbal combinations including Da Huang and Sheng Di Huang. Certain embodiments also include Jin Yin Hua. Other embodiments include one or more of Mu Dan Pi, Di Gu Pi, Xian He Cao, and Chun Gen Pi. Certain embodiments include herbal extracts or molecular components such as emodin, digoxin, and/or other molecules such as aucubin, beta-sitosterol, vanillic acid, rhein, rhapontin and carvacrol. Combinations of these and other herbs, herbal extracts and/or molecules described herein are provided in various embodiments.

Along with certain combinations of herbs and/or herbal extracts, emotives or molecular components as described herein, a shampoo, conditioner, cream, ointment or other topical eczema treatment in accordance with certain embodiments may include one or more other components including one or more surfactants and/or co-surfactants, thickening agents, pH adjusters, buffers, aesthetic additives, water, hydro-alcoholic hair serum and/or another dispersive agent, solvent, solubilizer or vehicle, hair-fall or hair-loss control actives, conditioners, preservatives and/or moisturizers and/or vitamins, humectants, one or more cationic polymers, silicone, a suspending agent, perfume and/or other additives that may be consistent with a healthy shampoo, conditioner, cream, ointment or other topical eczema treatment.

Example Treatments and Medicinal Dosage Compositions

Treatment methods in accordance with certain embodiments may include administering periodic doses of an herbal combination of one or more herbs described herein, such as Da Huang, Sheng Di Huang or Jin Yin Hua, or combinations thereof, as a medicine or medicinal supplement, alone or in combination with a known or discovered treatment, for treating a patient with psoriasis, inflammatory disorders, autoimmune disorders, scalp psoriasis, dermatitis, atopic dermatitis, eczema, herpes, shingles, rheumatoid arthritis (RA), arthritic psoriasis/psoriatic arthritis, Alzheimer's, Parkinson's, irritable bowel syndrome (IBS), colitis, prostitis, vasculitis, osteoarthritis, seborrheic dermatitis, acne, colitis, skin lesions, diabetes, hypertension, allergies, asthma, capuche sarcoma, autoimmune or inflammation related symptoms or disorders, dermatologic or cardiovascular conditions, metabolic syndrome, hypotension, coronary artery disease, depression, lupus, sarcoidosis, muscular sclerosis, crohn's disease, UV exposure, burns, warts, dandruff, seborrheic dandruff, chronic inflammation, seborrhea, keratosis, alopecia, hirsutism, capitis, melanoma or non-melanoma skin cancer, basal cell cancer (BCC), squamous cell cancer (SCC), scleroderma, dermatofibrosarcoma protuberans, Merkel cell carcinoma, Kaposi's sarcoma, keratoacanthoma, spindle cell tumors, sebaceous carcinomas, microcystic adnexal carcinoma, Paget's disease of the breast, atypical fibroxanthoma, leiomyosarcoma, and angiosarcoma, Marjolin's ulcers, kidney failure, nerve damage caused by a skin condition, or skin burrowing mites, or a skin ailment, lesion or sore, particularly of the scalp and also for other skin regions affected by an ailment that is susceptible to topical or hair treatment, as well as hair fall or hair loss conditions, or combinations thereof.

A treatment method in accordance with certain embodiments may include administering periodic doses methotrexate, and/or another known treatment regimen described herein or as understood by those skilled in the art, along with an herbal combination of one or more herbs described herein, for treating a patient with psoriasis, eczema, melanoma, inflammation or a form of cancer that is known to be effectively treated with methotrexate such as cancer of the breast, skin, head and neck, or lung or rheumatoid arthritis, psoriasis or leukemia.

A treatment method in accordance with certain embodiments may include administering periodic doses of Pemetrexed, Pralatrexate, Methotrexate sodium, Pemetrexed Disodium or a folate analog metabolic inhibitor, alone or in combination with methotrexate, and/or another known treatment regimen described herein or as understood by those skilled in the art, along with an herbal combination of one or more of Da Huang, Sheng Di Huang, and Jin Yin Hua, and/or one or more of the other herbs described herein, for treating a patient with psoriasis, eczema, melanoma, inflammation or another inflammatory or autoimmune disease or form of cancer that is known to be effectively treated with methotrexate or another known treatment described herein or a discovered treatment such as for treating cancer of the breast, skin, bladder, head and neck, or lung, osteosarcoma, lymphoma, or trophoblastic neoplasms, or inflammation, or an autoimmune disease such as rheumatoid arthritis, juvenile dermatomyositis, psoriasis, psoriatic arthritis, lupus, sarcoidosis, capuche sarcoma, Crohn's disease, eczema and many forms of vasculitis, or leukemia or conditions for which immunosuppressive drugs are commonly used, or combinations thereof.

A treatment method in accordance with certain embodiments may include administering periodic doses of an herbal combination of one or more of Da Huang, Sheng Di Huang, and Jin Yin Hua, along with one or more of a class of drugs that are specifically understood for their effectiveness at treating auto immune diseases and/or for curbing bodily rejections after implantation or transplantation of an organ or bone marrow, including drugs that influence lymphocytes such as Azathioprine, Mycophenolate mofetil, Methotrexate and/or Cyclophosphoamide, and/or drugs that slow down meiosis of lymphocytes such as Cyclosporine, Tacrolimus, Sirolimus (Rapamycin) and/or drugs that neutralize cytokines such as Infliximab, Etanercept, Adalimunab and/or Anikra.

A treatment regimen may also include a known or discovered treatment and one or more of the herbs described herein in combination with approximately 1 ug/ml-15 ug/ml of emodin, or approximately 5 ug/ml-10 ug/ml or more of emodin, alone or in combination with respectively 0.1 ug/ml-0.15 ug/ml of digoxin or 0.05 ug/ml-0.10 ug/ml or more of digoxin before, during and/or after administration of a known or discovered treatment regimen, such as those described herein or that may be understood by those skilled in the art or that may be discovered. Other combinations may be used in the treatment, including combining 5 ug/ml or more of emodin, alone or with at least approximately 0.10 ug/ml digoxin, or at least approximately 10 ug/ml emodin, alone or with at least approximately 0.10 ug/ml digoxin, or more than 5 ug/ml of emodin, alone or with at least approximately 0.05 ug/ml digoxin, or at least approximately 10 ug/ml emodin, alone or with at least approximately 0.05 ug/ml digoxin. Other combinations may be used and prescribed by physicians depending on factors such variances in weight, age, gender, family or patient history, or other characteristics specific to patients.

The treatment regimen may include once or twice daily doses, or several doses per day, or two or more weekly doses or otherwise. Doses may be taken more than once or twice a day, while the amounts of each dose would be determined according to the periodicity of the treatments.

Example Dosage Compositions and Combination Therapies

Effective doses of an herbal combination of Da Huang, Sheng Di Huang and Jin Yin Hua have been demonstrated in mice between 1500 mg/kg and 500 mg/kg. Very low doses of 250 mg/kg may also be administered with modest effectiveness and elevated doses between 1500 mg/kg and 3000 mg/kg may be administered as tolerated with enhanced curative potential. This effective dose range in humans is approximately between 162.0 mg/kg and 40.50 mg/kg, while very low formulations of 20.25 mg/kg and high doses between 162 mg/kg and 324 mg/kg are also capable of formulation. The proportions of the three herbs have been shown to be effective at approximately one part Da Huang, one part Jin Yin Hua and between two and four parts Sheng Di Huang.

An elevated dose example for a 100 kg patient includes 2.4 grams Da Huang, 2.4 grams Jin Yin Hua and 7.2 grams Sheng Di Huang. For a 50 kg patient, an elevated dose example includes 1.2 grams Da Huang, 1.2 grams Jin Yin Hua and 3.6 grams Sheng Di Huang.

A medium dose example for a 100 kg patient includes 1.6 grams Da Huang, 1.6 grams Jin Yin Hua and 4.8 grams Sheng Di Huang. For a 50 kg patient, a medium dose example includes 0.8 grams Da Huang, 0.8 grams Jin Yin Hua and 2.4 grams Sheng Di Huang.

A low dose example for a 100 kg patient includes 0.8 grams Da Huang, 0.8 grams Jin Yin Hua and 2.4 grams Sheng Di Huang. For a 50 kg patient, a medium dose example includes 0.4 grams Da Huang, 0.4 grams Jin Yin Hua and 1.2 grams Sheng Di Huang.

A very low dose example for a 100 kg patient includes 0.4 grams Da Huang, 0.4 grams Jin Yin Hua and 1.2 grams Sheng Di Huang. For a 50 kg patient, a medium dose example includes 0.2 grams Da Huang, 0.2 grams Jin Yin Hua and 0.6 grams Sheng Di Huang.

An elevated dose example for a 100 kg patient includes 2.4-4.8 grams Da Huang, 2.4-4.8 grams Jin Yin Hua and 7.2-14.4 grams Sheng Di Huang. For a 50 kg patient, a high dose example includes 1.2-2.4 grams Da Huang, 1.2-2.4 grams Jin Yin Hua and 3.6-7.2 grams Sheng Di Huang.

In accordance with these examples, formulations may be prepared for and administered to 100 kg patients that include 0.4-4.8 grams Da Huang, 0.4-4.8 grams Jin Yin Hua and 1.2-14.4 grams Sheng Di Huang, and to 50 kg patients including 0.2-2.4 grams Da Huang, 0.2-2.4 grams Jin Yin Hua and 0.6-7.2 grams Sheng Di Huang. A moderate range example for 100 kg patients includes 0.8-2.4 grams Da Huang, 0.8-2.4 grams Jin Yin Hua and 2.4-7.2 grams Sheng Di Huang, and that for 50 kg patients includes 0.4-1.2 grams Da Huang, 0.4-1.2 grams Jin Yin Hua and 1.2-3.6 grams Sheng Di Huang. These example dosage compositions may be administered multiple times in a treatment regimen lasting a few days or weeks or even months at intervals of a few hours to daily, every other day or as needed.

In another example, a treatment regimen may include 1-10 gram daily doses of combinations of Da Huang, Sheng Di Huang and Jin Yin Hua. A treatment regimen may include 2-5 gram daily doses, or approximately 3 gram daily doses. In the 3.0 gram daily dose example, 1.5 gram doses may be administered twice daily, i.e., 1.5 grams twice a day. A total daily dose may be administered in the form of four (4) tablets, e.g., 2 tablets, twice a day, of 1.0 gram each containing 750 mg of a combination of Da Huang, Sheng Di Huang and Jin Yin Hua as well as 250 mg of excipients.

In another example, a psoriasis treatment regimen may include administration of combinations of two or more of Da Huang, Sheng Di Huang and Jin Yin Hua along with Ustekinumab (by Janssen) and/or with another IL-12 and/or IL-23 inhibitor.

In another example, a psoriasis treatment regimen may include administration of combinations of two or more of Da Huang, Sheng Di Huang and Jin Yin Hua along with Humira (by Abbott) and/or with another TNF alpha inhibitor.

In another example, a psoriasis treatment regimen may include administration of combinations of two or more of Da Huang, Sheng Di Huang and Jin Yin Hua along with Tofacitinib (by Pfizer) and/or with another JAK and/or STAT inhibitor.

In another example, a psoriasis treatment regimen may include administration of combinations of two or more of Da Huang, Sheng Di Huang and Jin Yin Hua along with Secukinumab (by Novartis) and/or another IL-17 inhibitor.

In another example, a psoriasis treatment regimen may include administration of combinations of two or more of Da Huang, Sheng Di Huang and Jin Yin Hua along with Otezla/Apremilast (by Celgene) and/or another PDE4 inhibitor.

In another example, a psoriasis treatment regimen may include administration of combinations of two or more of Da Huang, Sheng Di Huang and Jin Yin Hua along with Briakinumab and/or another p40 subunit of IL-12 and/or IL-23 and/or a humanized p40 monoclonal antibody.

In another example, a psoriasis treatment regimen may include administration of combinations of two or more of Da Huang, Sheng Di Huang and Jin Yin Hua along with Fezakinumab (by Pfizer) and/or another IL-22 inhibitor.

In another example, a psoriasis treatment regimen may include administration of combinations of two or more of Da Huang, Sheng Di Huang and Jin Yin Hua along with an IL-20 inhibitor.

In another example, a psoriasis treatment regimen may include administration of combinations of two or more of Da Huang, Sheng Di Huang and Jin Yin Hua along with an IL-23/p19 inhibitor.

In another example, a psoriasis treatment regimen may include administration of combinations of two or more of Da Huang, Sheng Di Huang and Jin Yin Hua along with a JAK3 inhibitor.

In another example, a psoriasis treatment regimen may include administration of combinations of two or more of Da Huang, Sheng Di Huang and Jin Yin Hua along with a Th1, Th17 and/or Th22 cell inhibitor.

In another example, a psoriasis treatment regimen may include administration of combinations of two or more of Da Huang, Sheng Di Huang and Jin Yin Hua along with an IFN gamma inhibitor.

In another example, a psoriasis treatment regimen may include administration of combinations of two or more of Da Huang, Sheng Di Huang and Jin Yin Hua along with an IL-17R, IL-19, IL-20, IL-22, sPLA2, NO (nitric oxide), VEGF, IL-24, key tyrosine and/or topoisomerase inhibitor.

In another example, a treatment regimen for IBS (irritable bowel syndrome) and/or colitis may include administration of combinations of two or more of Da Huang, Sheng Di Huang and Jin Yin Hua, alone, for example Da Huang and Sheng Di Huang as 2HX or including Jin Yin Hua as 3HX, or along with a TNF, IL-8, MIP-3-α, and/or ICAM-1 inhibitor, and/or one or more other inflammatory marker inhibitors. Moreover, a diagnostic or prognostic kit may include a test kit for measuring levels in gastrointestinal cells of one or more of TNF, IL-8, MIP-3-α, and/or ICAM-1 and/or one or more of, or a panel of several, inflammatory markers, and indicating an IBS and/or colitis diagnosis and/or prognosis for treatment.

Diagnostic and/or prognostic test kits are provided herein for each recited condition that include test kits for measuring one or more of, or a panel of several, markers associated with such recited condition, and indicators that provide diagnostics and/or prognostics for a patient. The prognostic and/or diagnostic kits may include one or more of Da Huang, Sheng Di Huang and Jin Yin Hua and/or one or more other herbs, molecules, and/or biologic, protein, molecule or receptor inhibitors or enablers, and/or treatments and/or medicines recited herein.

In another example, a psoriasis treatment regimen may include administration of combinations of two or more of Da Huang, Sheng Di Huang and Jin Yin Hua along with one or more of: a topical therapy such as Vitamin D, Calcipotriol, Corticosteroids, Dithranol, Retinoids, Tacrolimus, and/or Salicylic acid; a systemic therapy such as Methotrexate, Cyclosporine, Hydrea (hydroxyurea), and/or Retinoids; a phototherapy such as UV-B, Psoralen plus ultraviolet therapy and/or excimer laser; a combination therapy such as Methotrexate+Etanercept, Adalimumab (Humira®)+Calcipotriol+Betamethasone Dipropionate, and/or Alefacept+ultraviolet B (UVB) phototherapy, methotrexate, cyclosporine, and/or systemic retinoids; an herbal therapy such as Duzhong (Eucommia ulmoides Oliv.), Yerba mate (Ilex paraguariensis), Linseed oil, Fish oil, Indigo naturalis, Turmeric and/or Aloe Vera; and/or a biological and/or small molecule inhibitor and/or an enzyme inhibitor such as Denilukin diftitox, Efalizumab, Alefacept, Ustekinumab and/or Etanercept.

In another example, a rheumatoid arthritis (RA) treatment regimen may include administration of combinations of two or more of Da Huang, Sheng Di Huang and Jin Yin Hua along with Humira (by Abbott) and/or with another TNF alpha inhibitor.

In another example, a rheumatoid arthritis (RA) treatment regimen may include administration of combinations of two or more of Da Huang, Sheng Di Huang and Jin Yin Hua along with methotrexate.

In another example, a rheumatoid arthritis (RA) treatment regimen may include administration of combinations of two or more of Da Huang, Sheng Di Huang and Jin Yin Hua along with Enbrel (by Amgen & Pfizer) and/or another TNF alpha inhibitor approved for RA or for both psoriasis & RA.

In another example, a rheumatoid arthritis (RA) treatment regimen may include administration of combinations of two or more of Da Huang, Sheng Di Huang and Jin Yin Hua along with Remicade (by Janssen & Merck) and/or another TNF alpha inhibitor approved for RA or for two or more of psoriasis, RA and IBD (irritable bowel disease).

In another example, a rheumatoid arthritis (RA) treatment regimen may include administration of combinations of two or more of Da Huang, Sheng Di Huang and Jin Yin Hua along with Infliximab, Etanercept, Adalimumab, Anakinra, methotrexate, hydroxychloroquine, sulfasalazine and/or Leflunomide.

In another example, an Alzheimer's or Parkinson's treatment regimen may include administration of combinations of two or more of Da Huang, Sheng Di Huang and Jin Yin Hua, alone, or along with another approved Alzheimer's or Parkinson's treatment.

In another example, a rheumatoid arthritis (RA) treatment regimen may include administration of combinations of two or more of Da Huang, Sheng Di Huang and Jin Yin Hua along with an IL-17, IL-23, IL23 receptor and/or IL-23 axis inhibitor.

In another example, a RA, IBD and/or MS treatment regimen may include administration of combinations of two or more of Da Huang, Sheng Di Huang and Jin Yin Hua along with an IL-23 or IL-17 or TNF alpha inhibitor.

In another example, an RA, IBD, MS, Alzheimer's, Parkinson's, inflammatory colitis, osteoarthritis, psoriasis, eczema and/or dermatitis treatment may include administration of combinations of two or more of Da Huang, Sheng Di Huang and Jin Yin Hua along with an IL-1, IL-6 and/or IL-8 inhibitor.

In another example, an RA, IBD, MS, Alzheimer's, Parkinson's, inflammatory colitis, osteoarthritis, psoriasis, eczema and/or dermatitis treatment may include administration of combinations of two or more of Da Huang, Sheng Di Huang and Jin Yin Hua along with a BTK, SYK, ZAP-70, PI3KCD, AKT, HER-2, FLT-3, MAPK1, BRAF, and/or MEK1 inhibitor.

In another example, an approved treatment for AML, ALL, CML, CLL and/or another leukemia or other cancer medication may be supplemented by administration of combinations of two or more of Da Huang, Sheng Di Huang and Jin Yin Hua.

In another example, leukemia or other cancer or other disease treatments that include a PD-1, CD279 and/or PD-L1 inhibitor may be supplemented by administration of combinations of two or more of Da Huang, Sheng Di Huang and Jin Yin Hua.

In another example, Desatinib and/or another LYN, BTK and/or ABL inhibitor, and/or Fostamatinib and/or another SYK, FLT3, KIT, LCK, JAL1, JAK3, PLC, AKT and/or BCR inhibitor, and/or Idelalisib (GS-1101) or another PI3K delta inhibitor, and/or Ibrutinib and/or another BTK inhibitor and/or Gefitinib and/or another Zap 70 inhibitor, and/or Dasatinib and/or another Lyn inhibitor, or another approved treatment for CLL and/or another leukemia or other cancer medication may be supplemented by administration of combinations of two or more of Da Huang, Sheng Di Huang and Jin Yin Hua.

In another example, an Alzheimer's treatment may include administration of combinations of two or more of Da Huang, Sheng Di Huang and Jin Yin Hua along with a TNF-alpha, IL-6, IL-8, IL-12, GMCSF, and/or MCP-1 inhibitor.

In another example, a treatment may include administration of combinations of two or more of Da Huang, Sheng Di Huang and Jin Yin Hua along with a administration of combinations of two or more of Da Huang, Sheng Di Huang and Jin Yin Hua along with one or more kinase inhibitors, for example, an AKT1 (PKB alpha), ERBB2 (HER2), FLT3, MAPK1 (ERK2), PRKCA (PKC alpha), BRAF, BRAF V599E and/or MAP2K1 (MEK1) inhibitor.

Methods of preparing treatment medicines for psoriasis, eczema, melanoma, inflammation, leukemia or other cancer and/or an autoimmune disorder are also provided, including preparing a medicinal composition including methotrexate, or another known treatment described herein, or a discovered treatment, and an herbal combination of one or more of Sheng Di Huang, Da Huang, Jin Yin Hua, or one or more of the other herbs described herein and/or one or more molecules, molecular extracts or molecular compounds described herein.

Example Formulations

In one example formulation, a topical or oral formulation, or IV, subdermal, patch or other formulation described herein or understood to those skilled in the art may include 750 mg (milligrams) of a combination of Da Huang, Sheng Di Huang and Jin Yin Hua, e.g., 1:2:1 or 1:3:1 or 1:4:1, i.e., 187.5 mg of Da Huang, 375 mg of Sheng Di Huang and 187.5 mg of Jin Yin Hua or 150 mg of Da Huang, 450 mg of Sheng Di Huang and 150 mg of Jin Yin Hua or 125 mg of Da Huang, 500 mg of Sheng Di Huang and 125 mg of Jin Yin Hua or 100-200 mg Da Huang, 100-200 mg Jin Yin Hua and 300-600 mg Sheng Di Huang. The combination may include two herbs, e.g., 100-400 mg Da Huang or Jin Yin Hua and 300-600 mg of Sheng Di Huang or 100-650 mg of each of Da Huang and Jin Yin Hua. The combination may alternatively include 750 mg of one of Da Huang, Sheng Di Huang and Jin Yin Hua in certain embodiments including combinations with other herbs, molecules or medicines recited herein.

In another example formulation, a topical or oral formulation, or IV, subdermal, patch or other formulation described herein or understood to those skilled in the art may include 1-15% of a combination of Da Huang, Sheng Di Huang and Jin Yin Hua, e.g., 1:2:1 or 1:3:1 or 1:4:1, i.e., 0.25%-3.75% Da Huang, 0.5%-7.5% Sheng Di Huang and 0.25%-3.75% Jin Yin Hua or 0.2%-3% Da Huang, 0.6%-9% Sheng Di Huang and 0.2%-3% Jin Yin Hua or 0.15%-2.5% Da Huang, 0.5%-7.5% Sheng Di Huang and 0.15%-2.5% Jin Yin Hua or 2%, 2.5%, 3%, 4%, 5%, 6%, 7.5%, 9%, 10%, 11%, 13% 15% or 20% of a combination of Da Huang, Sheng Di Huang and Jin Yin Hua. The combination may include two herbs, e.g., 0.25%-5% Da Huang or Jin Yin Hua and 0.75%-10% Sheng Di Huang, or 0.5%-7.5% of each of Da Huang and Jin Yin Hua. The combination may alternatively include 1%-15% Da Huang, Sheng Di Huang or Jin Yin Hua alone, in certain embodiments particularly including combinations with other herbs, molecules or medicines recited herein. This example formulation may include 500 mg, 750 mg, 1000 mg or 1500 mg of a combination of Da Huang, Sheng Di Huang and Jin Yin Hua, e.g., 1:2:1 or 1:3:1 or 1:4:1, i.e., for the 750 mg example, 187.5 mg of Da Huang, 375 mg of Sheng Di Huang and 187.5 mg of Jin Yin Hua or 150 mg of Da Huang, 450 mg of Sheng Di Huang and 150 mg of Jin Yin Hua or 125 mg of Da Huang, 500 mg of Sheng Di Huang and 125 mg of Jin Yin Hua or 100-200 mg Da Huang, 100-200 mg Jin Yin Hua and 300-600 mg Sheng Di Huang.

In addition to the above active herbal combination ingredient, a medicinal tablet composition is provided for example for oral administration that may include one or more of the following further ingredients: 125 mg of MCC (Avicel), 20 mg of talc powder, 30 mg of aerosol 200, 10 mg of croscarmellose sodium and/or 30 mg of PVPK 30. This example may also include one or more of the following lubrication ingredients: 20 mg of croscarmellose sodium, 5 mg of aerosol 200, 20 mg of talc powder and/or 10 mg of magnesium sterate.

A medicinal cream is also provided for topical administration that includes the above active herbal combination ingredient, in an example concentration of 2.5%, and one or more of the following further ingredients: 2% sesame oil or *Sesamum indicum* (sesame) seed oil, 4% cetostearyl alcohol or cetearyl alcohol, 5% arlacel 165 or glyceryl stearate or PEG-100 stearate, 3% light liquid paraffin or mineral oil, 2% cresmer wax EW or ceteareth-20 or cetearyl alcohol, 3% stearyl stearate, 0.2% butyl hydroxyl toluene or BHT, 4.2% propylene glycol, 0.2% potassium sorbate, 0.2% sodium benzoate, 5% glycerol or glycerin, 0.1% sandalwood oil or santalum album (sandalwood) oil, and 68.6% water.

A medicinal cream is also provided for topical administration that includes the above active herbal combination ingredient, in aqueous extract and in an example concentration of 2.5%, and one or more of the following further ingredients: till oil, cetostearyl alcohol, arlacel 165, light liquid paraffin, cresmer wax EW, stearyl stearate, butyl hydroxyl toluene, propylene glycol, sodium methyl paraben, sodium propyl paraben, glycerol, sandalwood oil. A cream placebo may be formulated for clinical trials that substitutes F-24 chocolate brown color TAS and brilliant blue color for the above active herbal combination ingredient.

Preparation of Topical, Oral or Subdermal Medicine

Treatments described herein may be prepared for topical use for treatment of melanoma, eczema, dermatisis, BCC (basal cyr carcinoma) and inflammatory skin diseases like Psoriasis. For example, combinations of herbs and/or herbal extracts as described herein may be prepared as a cream to apply onto the skin. Another known or discovered treatment may be included or may be administered separately before, during or after the herbal treatment. The other known or discovered treatment, along with herbal combinations and/or herbal extract combinations described herein may be injected to infected areas of the skin of a patient using a syringe. An example method for preparation of an external cream in accordance with certain embodiments is provided below.

First, two of more of the herbs may be cooked, for example, as described elsewhere herein or as may be understood or determined by those skilled in the art. A cream is then prepared that may be somewhat more of less than half herbs and half cream, e.g., a 25%-75% liquid of herbs in 1:1 ratio and 25%-75% cream may be used. The herbs can also be prepared as a tincture, e.g., soaking the herbs in alcohol for a period of time such as 2 weeks in a ratio of 1:3, for example. This herbal liquid can then be mixed with the cream in the same way as described above.

The herbs may be prepared for cooking by grinding and/or homogenizing the herbs. Grinding may be achieved using a Dyno-mill run once to obtain, e.g., 250 nm particle sizes or multiple times down to, e.g., 150 nm particle sizes. A high pressure homogenizer may be used, whereby the mixture is pushed through a filter, e.g., a 0.2 μm filter. Sonication or ultrasound may also be used.

Straining may be performed to get an aqueous extract. Lyophilization or freeze drying may be performed to prepare the mixture for in vitro use. Solubilization may be performed along with selection of a concentration of the extract. A cream, tablet, capsule, nano-lipid carrier, nanogel, or nanochrystals, or nano-particulates may be formulated for administration to human or animal patients.

Treatments described herein may also be effective against immunodeficiency diseases such as HIV and AIDS, as well as other conditions affecting or caused by disorders of the immune system. Herbal combinations of one or more of Da Huang, Sheng Di Huang and Jin Yin Hua and/or one or more other herbs or molecules described herein may be administered as a nutritional supplement or as a supplement to an exercise regimen or as an energy supplement or as a pain relief supplement or as a diuretic or sleep aid. NSAIDs, such as ibuprofen, naproxen and aspirin, other non-steroidal anti-inflammatories, acetaminophen, and/or steroidal anti-inflammatories may be combined with an herbal combination of one or more of Da Huang, Sheng Di Huang and Jin Yin Hua and/or one or more other herbs or molecules described herein, with or without administration of a known or discovered treatment, before, during or after the herbal treatment, to treat inflammation or other ailments that are commonly treatable with NSAIDs, including chronic pain. Formulations may be prepared for oral or topical administration as long release, lipidized dosage compositions or as short release non-lipidized formulas.

A cooking process may be performed as in the example of FIGS. 27A-27B. Referring to FIG. 27A, a step 502 in a cooking process may include taking about 25-30 grams of a first herb, e.g., da Huang, and a second herb, e.g., Jin Yin Hua, and grinding in a mixer grinder for three to five minutes or until a fine powder has been mixed and ground. A step 504 in the process may include taking about 75-80 grams of a third herb, e.g., Sheng di Huang, and grinding in a mixer grinder for three to five minutes or until a fine powder has been mixed and ground.

A step 506 in the cooking process may further include grinding 25 grams of the first herb, e.g., da Huang, 25 grams of the second herb, e.g., Jin Yin Hua, and 75 grams of the third herb, e.g., Sheng di Huang, and mixing thoroughly to prepare a three herb combination ("3HX").

A next step 508 may include weighing about 25 grams of the powdered three herb combination 3HX in a 2000 ml beaker or other suitable container. A next step 510 may include adding water (RT) to the 25 grams of powdered three herb combination 3HX in a ratio of about 20 ml water per gram of powdered three herb combination and pouring the mixture along with a magnetic bead into the beaker. A next step 512 may include allowing the aqueous three herb combination to soak in distilled water for around 15 minutes before boiling.

Referring now to FIG. 27B, a hot plate may be pre-heated, for 10 minutes, e.g., before keeping the beaker for boiling, as indicated at step 522. A step 524 may then include boiling the mixture to 85-90° C. A step 526 may include allowing the mixture to come down to 70-75° C. after removing the mixture from the hot plate. A step 528 may include covering the beaker properly with aluminum paper and cooking the mixture at 70° C. on a hot plate. A time of cooking in accordance with the example of step 530 from the beginning to the end should be around 60 minutes which includes boiling, cooling and cooking.

A next step 532 may include straining the mixture with the help of a manual strainer. A step 534 may involve filtering the sample and measuring the total volume obtained, as well as making up an obtained extract up to 425 ml, centrifuging the extract obtained after making up at 4000 rpm for 30 minutes and collecting the supernatant.

A cream or lotion or shampoo or ointment or gel or patch or other topical formulation may be prepared. Also, a pill may be prepared in lipidized or non-lipidized form, and coated or uncoated for extended release, timed release, sustained release, modified release, immediate release, quick release, delayed release, controlled release, controlled delivery, long-acting or sustained action. Also, an IV or subdermal injection fluid may be formulated.

In the example of FIG. 28, an aqueous extract, e.g., including a herein-described one, two or three (or more) herb combination is prepared, e.g., in accordance with the example of FIGS. 27A-27B, or otherwise prepared, provided or acquired at step 602. A step 604 may include converting the aqueous extract into powder form. The converting into powder form of step 604 may include one or more of lyophilization or freeze drying 606, vacuum drying 608 and/or spray drying 610. The drying may include heating or proximate hygroscopic disposition or spinning or otherwise as may understood by those skilled in the art.

At step 612, the lyophilized or otherwise dried one, two or three (or more) herb powder may be used to formulate a tablet, pill, capsule or other orally-administered formulation. Such orally-administered formulation may be uncoated 614 or color coated 616. Batch sizes may be in multiples of one or more thousand.

Figure 29:
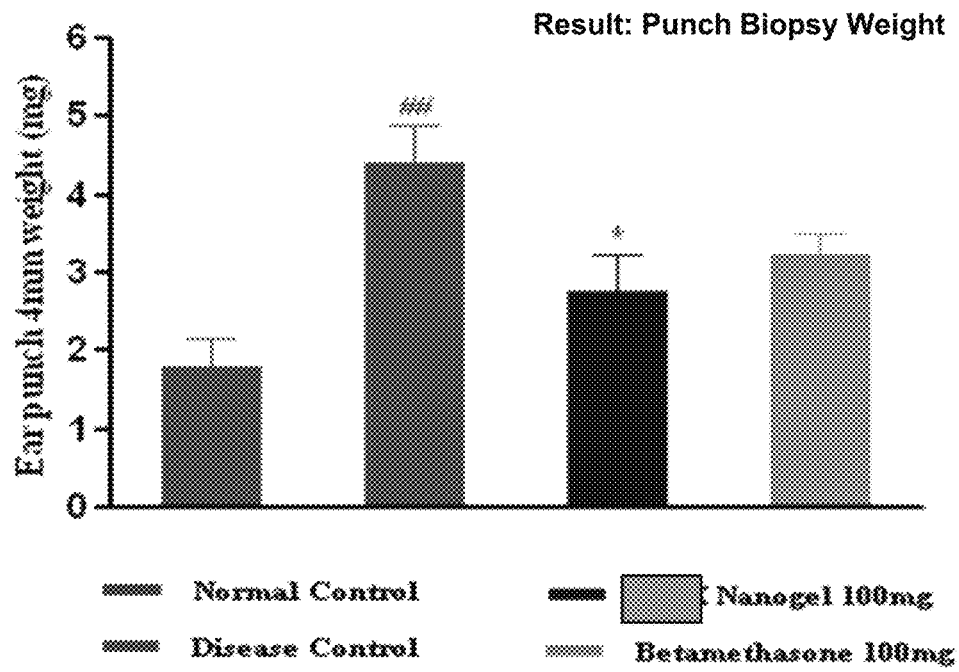
FIG. 29 includes plots of ear punch biopsy weight for 100 mg 3HX nanogel and betamethasone formulations in accordance with certain embodiments.
Figure 30:
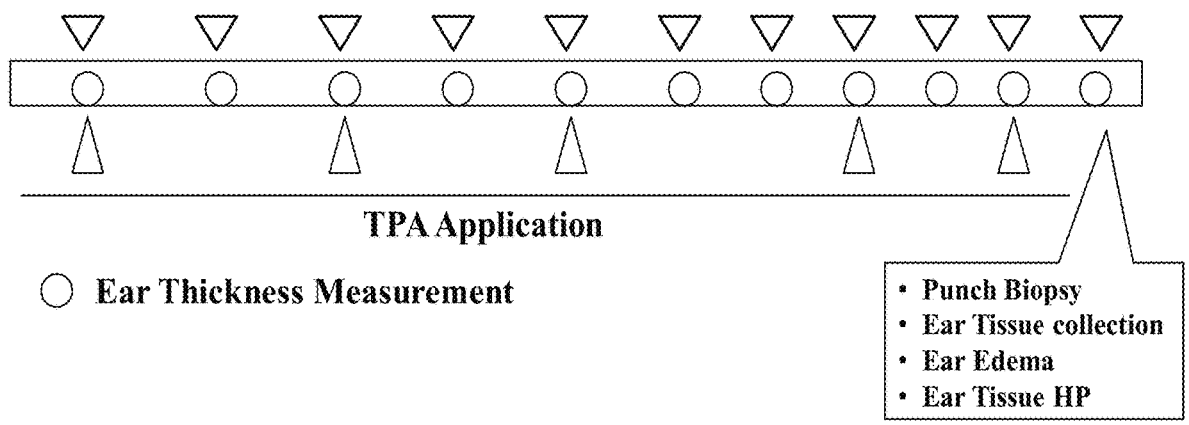
FIG. 30 illustrates study parameters for testing and comparing 3HX nanogel, 3HX cream and betamethasone formulations in accordance with certain embodiments.
Figure 31:
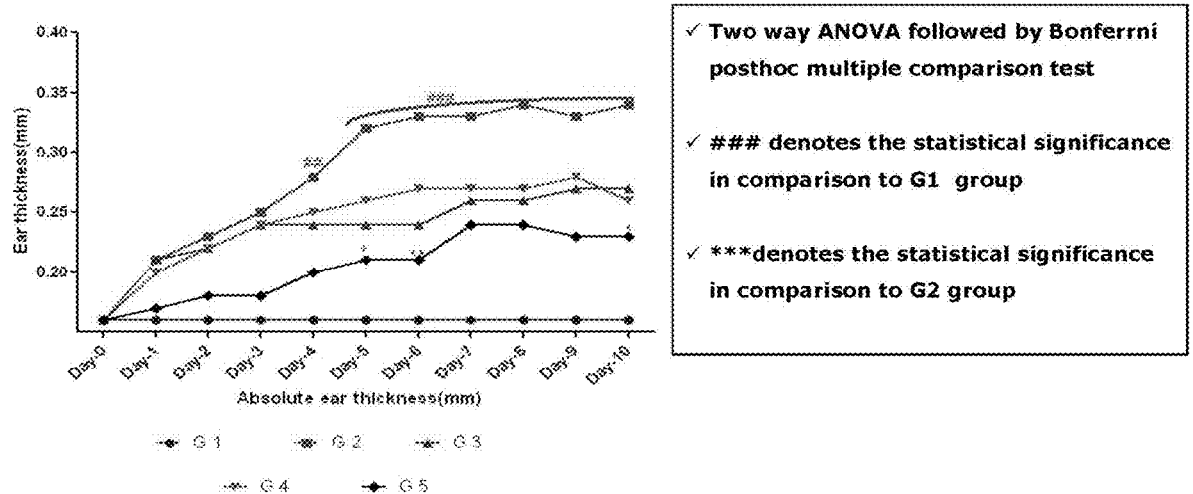
FIG. 31 includes plots of ear thickness for 3HX nanogel, 3HX cream and betamethasone formulations in accordance with certain embodiments.
Figure 33:
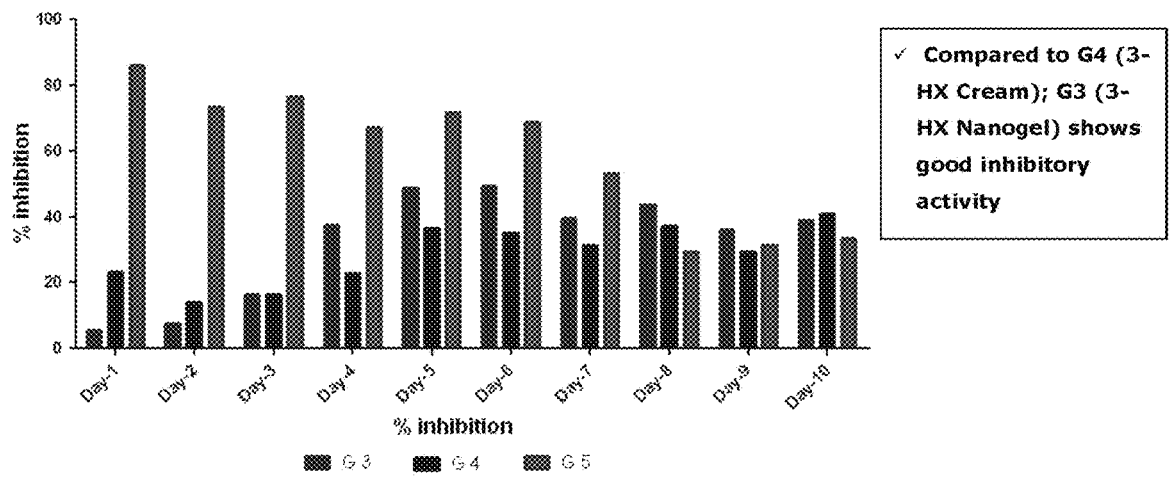
FIG. 33 includes plots of % inhibition of ear edema for 3HX nanogel, 3HX cream and betamethasone formulations in accordance with certain embodiments.
Figure 35:
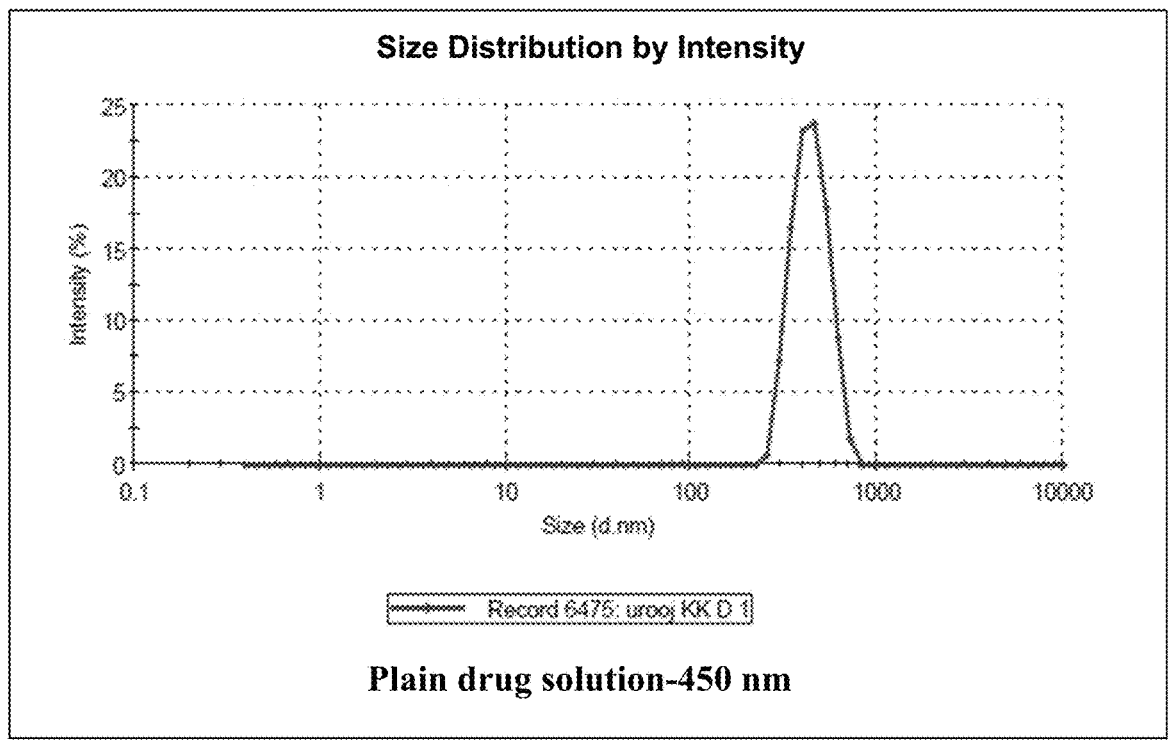
FIG. 35 is a graph showing a Plain drug solution—450 nm.
Figure 36:
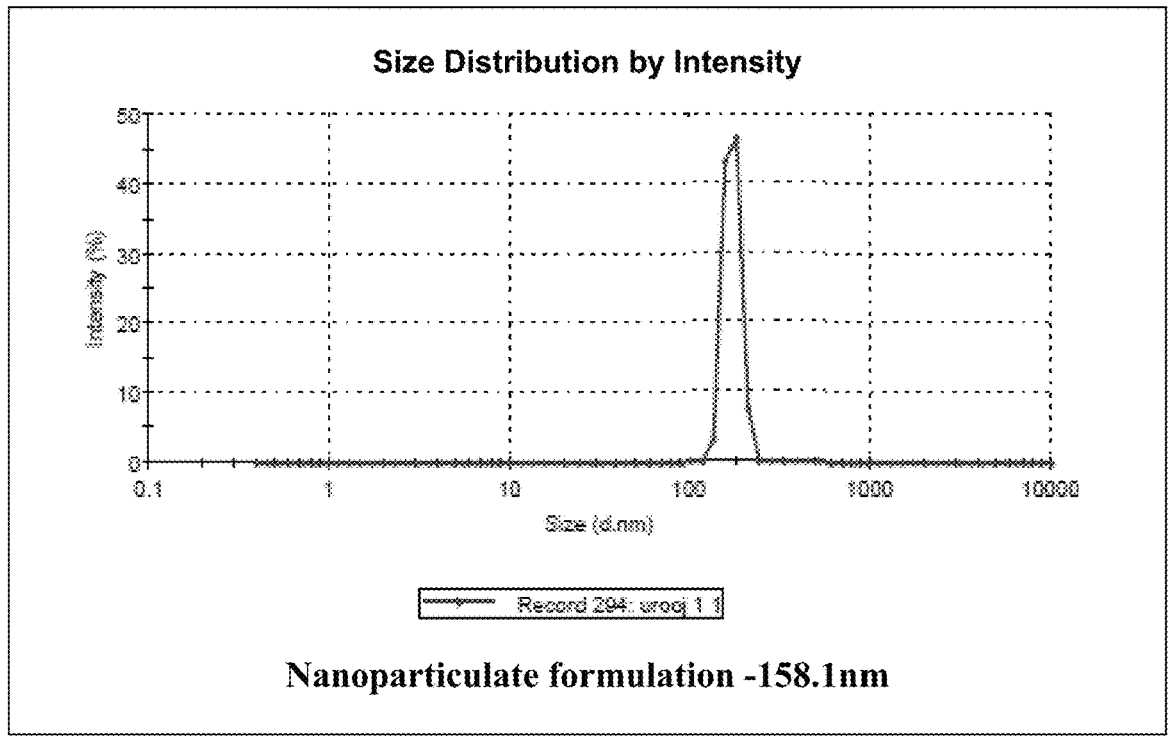
FIG. 36 is a graph showing a Nanoparticulate formulation—158.1 nm.

Referring to FIG. 29, an example of a shampoo in accordance with certain embodiments is illustrated as including nine generalized components. These nine components include a surfactant, a thickening agent, a pH adjuster/buffer, an aesthetic additive, water, a conditioner, one or more active herbs or herbal extracts or molecules, a preservative and moisturizers/vitamins. Shampoos in accordance with various alternative formulations may include fewer than all of these nine components and they may include other active or inactive components known to those skilled in the art as having some advantage when included in a shampoo formula or in a medicinal combination for treating a skin condition such as psoriasis, eczema, melanoma, or dermatitis or hair loss or another head or scalp disorder or ailment.

A shampoo in accordance with certain embodiments includes one or more surfactants that may be known or discovered as being advantageous for cleaning hair with a shampoo. A primary surfactant may be included to provide flash foam for cleaning the hair by removing dirt and other impurities. A secondary surfactant may be included to provide stable foam and to reduce the harshness of the primary surfactant. A surfactant may be used that includes a charged, hydrophilic head group and a long, hydrophobic alkyl chain tail. Surfactants are configured to break molecular bonds between dirt and hair and to transport the dirt into an aqueous medium to be rinsed free from the hair and scalp. Examples of surfactants that may be contained in a shampoo in accordance with certain embodiments include sodium laureth sulphate, ammonium laureth sulfate, and sodium cocoyl isethionate. Examples of co-surfactants include cocamide MEA and cocoamidopropyl betaine.

A shampoo in accordance with certain embodiments may include a thickening or suspending agent. Examples of thickening or suspending agents that may be contained in accordance with certain embodiments include carbomer and PEG 150 distearate. The thickening agent may be included to stabilize the shampoo during storage and/or to prevent the setting or dumping of pigments and silicone.

A pH adjuster or buffer may be included in a shampoo in accordance with certain embodiments. An example of a pH adjuster or buffer includes citric acid, tartaric and sodium hydroxide. The pH adjuster or buffer is configured to cause the shampoo to be gentle to the skin. A lower pH may cause hair to be compact and to shine and to protect the surfactant from hydrolysis, and as such, the pH adjuster or buffer may serve to lower the pH of the shampoo. However, alternative embodiments include pH adjusters that serve to raise the pH of a shampoo that contains an herbal formula that exhibits an exceptionally low pH.

An aesthetic additive may be included in a shampoo in accordance with certain embodiments. Examples of aesthetic additives include colorants, opacifiers, UV absorbers, perfumes and natural and artificial fragrances.

One or more conditioners may be included in a shampoo in accordance with certain embodiments. The one or more conditioners may include a cationic polymer such as guar hydroxypropyl trimonium chloride. The one or more conditions may include silicone and/or a silicone emulsion such as dimethiconol, dimethicone, or amodimethicone. The silicone and/or silicone emulsion may serve to coat the hair and cause the hair to become soft, smooth and shiny.

A shampoo in accordance with certain embodiments includes one or more active herbs or herbal extracts or emotives that are described in several examples herein. These one or more active herbs or herbal extracts serve to promote treatment of certain hair and scalp conditions such as psoriasis, eczema, dermatitis, melanoma, hair loss and other hair or scalp conditions described herein or understood by those skilled in the art.

A preservative may be included in a shampoo in accordance with certain embodiments. The preservative may be configured to prevent microbial growth. Examples of preservatives that may be contained in a shampoo in accordance with certain embodiments include paraben free, formaldehyde donor free and halogenated free.

A moisturizer and/or one or more vitamins may be included in a shampoo in accordance with certain embodiments. Examples include combinations of D-Panthenol, vitamin E acetate, sodium PCA, glycerine and one or more amino acids. The moisturizer and/or vitamins may be configured to penetrate into hair shaft, seal cuticles and keep hair moisturized.

A shampoo in accordance with certain embodiments may include a hydro-alcoholic hair serum. Referring to FIG. 8, a hair growth cycle includes exogen, anagen, catagen and tetogen phases. The anagen phase involves active hair growth, whereby hair follicles regenerate and generate pigmented hair shafts. The telogen phase is a resting phase. The catagen phase involves cessation of hair growth and pigmentation, and release of papilla from the bulb. A hydro-alcoholic hair serum may be configured as a concentrated product that is typically left on the hair for a more extended duration than an ordinary shampoo with a typical shower routine. The hydro-alcoholic hair serum may be configured to be light and non-sticky on the scalp and as a non-irritant, to be light and non-sticky on the hair, to have little or no effect on hair volume, to strengthen scalp and DPC, to provide keratinization and collagen synthesis, to promote hair growth or to control hair fall, or combinations thereof. For example, the attributes of a hydro-alcoholic hair serum in accordance with certain embodiments may assist or promote treatment of psoriasis, seborrhea dandruff or hair fall. A hydro-alcoholic hair serum in accordance with certain embodiments may include water, alcohol, humectant, solubilizer, water-based polymer, scalp conditioner, niacinamide, caffeine and panthenol. The ratio of alcohol, water and solubilizer may be adjusted depending of the solubilization power of the active herbal treatment composition.

Nanogel Examples

Carbopol Ultraze 21 may comprise 1-5%, 1-4%, 1-3%, or 1-2% (w/v) of an example gel formulation. Propylene glycol may comprise 1-10% of this example gel formulation. Polyethylene glycol 400 (PEG 400) may comprise 1-15% of the example gel formulation. DMDM hydantoin may comprise 0.05-1% of a gel formulation. Menthol may comprise 0.1-1% of this example gel formulation. Isopropyl alcohol may comprise 0.5-0.1% of this example gel formulation. Triethanolamine as it is a gelling agent and added to maintain the pH of gel. Therefore, Triethanolamine may be included in an amount according to the pH of the gel between 6 and 7. Distilled water may comprise 80-120 ml of this example gel formulation. The combination of Sheng Di Huang, Da Huang and Jin Yin Hua that may be cooked to prepare a medicinal composition and may have particulate sizes below 450 nm, below 350 nm, below 250 nm and even below 150 nm due to grinding or milling, e.g., dyno-milling, such that an active herbal component of a medicinal composition may be included that is between 1-15% wt. %/v of the formulation.

Example Cooking Process

A step in an example process may include taking about one part of root and rhizome of DH, one part of flowers of JYH, and three parts of root of SDH and grind in a mixer grinder for 3-5 minutes until it appears to be a fine powder. After grinding, it may look like coarse or fine powder. One part of da huang, one part of jin yin hua and three parts of sheng di huang may be mixed together in an example process, while the sheng di huang may be added separately with a cooked mixture of da huang and jin yin hua. Water may be added to herb mixture in a ratio of 20 ml water per gram of herbs initially at room temperature and raised up to boiling temperature and turned down to cook at 70° C. in one example. In one example, one liter of extract preparation may take a minimum of 5 min+3 min to boil. One liter of extract at lab scale may take 2 hours, 2.5 hours or 3 hours in different examples. After boiling, the mixture may be cooked at 70° C. for 30-40 minutes. Other steps may include, for one liter extract preparation (Lab scale): soaking time: 15 minutes (10 minutes-1 hour); boiling time: 5-8 minutes (3 minutes to 15 minutes); Cooling to 70° C.:10-15 minutes (5 minutes to 1 hour); and/or cooking at 70° C.:30-40 minutes (5 minutes to 1 hour). The mixture may be strained with the help of a 100 mesh or fine mesh filter. Nano-particulate sizes between 100 nm and 300 nm are used in certain embodiments.

Nano-sized delivery systems may be selected for drug delivery because of one or more of the following reasons:

Because of their unique size and high loading capacities, nano-formulations appear to be able to deliver high concentrations of actives to disease sites.

Deliver the herbal material in the small particle size that enhances the entire surface area, thus allocating quicker dissolution in the blood.

Allows homogenous release over a longer period. The concentration also seems to persist at the site of action for longer period.

Shows EPR (enhanced permeation and retention) effect, i.e., enhanced permeation through the barriers because of the small size, and retention.

Exhibits passive targeting to the disease site of action, even without the addition of any particular ligand moiety.

Decrease in the dose of the herb formulation.

Decrease in the compliance issues due to high doses.

See, e.g., Nanotechnology-based drug delivery systems and herbal medicines: a review. Bonifacio B V et al., International Journal of Nanomedicine 2014:9 1-15, which is incorporated by reference.

Novel drug delivery systems in general help to target into the tissues through skin layers and can provide better therapy for topical treatment of psoriasis. Stratum corneum (SC) is the major challenge for the drug to get into the target tissues, via skin layers. Penetration enhancers added in the drug carriers help to increase the penetration capacity of drug through the outermost layer of the skin. Specific permeation studies on nano-3HX through different layers of the skin will tell us more.

For the preparation of one liter extract (on lab scale), centrifuge the extract for 30 minutes at 4000 rpm, and collect the supernatant.

Tablets and Capsules

An example tablet or capsule may include lactose monohydrate. In place of lactose monohydrate microcrystalline cellulose, and/or spray dried lactose, and/or Avicel may be used. In place of polyvinyl povidone k-30 or PVP K-30, PVP K-15 or HPMC can be used. Magnesium stearate and talc may be used as glidants and/or in place of talc, colloidal silicon dioxide can be used. The bioavailability enhancers piperine (0.5-10% w/w), (fulvic acid: 0.5-50% w/w) and/or inulin (1-30%) may be included in an example tablet or capsule and/or lysergol (2-2.5%) may be included as a bioavailability enhancer.

Lipid-Based Formulation

A lipid-based formulation may be made up of solid lipid, emulsifier and water/solvent. The lipids used may be triglycerides (tri-stearin), partial glycerides (Imwitor), fatty acids (stearic acid, palmitic acid), and steroids (cholesterol) and waxes (cetyl palmitate). Various emulsifiers and their combination (Pluronic F 68, F 127) have been used to stabilize the lipid dispersion. The combination of emulsifiers might prevent particle agglomeration more efficiently.

Example Ingredients

| Name of the ingredients | Concentrations |
| --- | --- |
| Lipid | 3.33% w/v |
| Phospholipids | 0.6-1.5% |
| Glycerol | 2-4% |
| Poloxamer 188 | 1.2-5% w/w |
| Soy phosphatidyl choline | 95% |
| Compritol | 10% |
| Cetyl palmitate | 10% w/w |
| Tego care 450 (surfactant) | 1.2% w/w |
| PEG 2000 | 0.25% |
| PEG 4500 | 0.5% |
| Tween 85 | 0.5% |
| Ethyl oleate | 30% |
| Na alginate | 70% |
| Ethanol/butanol | 2% |
| Tristearin glyceride | 95% |
| PEG 400 | 5% |
| Isopropyl myristate | 3.60% |
| Pluronic F 68 | 40% |
| Tween 80 | 50% |

Excipients for preparing an example oral lipid-based formulation may include dietary oils composed of medium (coconut or palm seed oil) or long-chain triglycerides (corn, olive, peanut, rapeseed, sesame, or soybean oils, including hydrogenated soybean or vegetable oils), lipid soluble solvents (polyethylene glycol 400, ethanol, propylene glycol, glycerin), and various pharmaceutically-acceptable surfactants (Cremophor® EL, RH40 or RH60; polysorbate 20 or 80; D-α-tocopherol polyethylene glycol 1000 succinate (TPGS®); Span 20; various Labrafils®, Labrasol®, and Gelucires®). These formulations, which took the form of either bulk oral solutions or liquid-filled hard or soft gelatin capsules, were applied in instances where conventional approaches (solid wet or dry granulation, or water-miscible solution in a capsule) did not provide sufficient bioavailability, or in instances in which the drug substance itself was an oil (dronabinol, ethyl icosapentate, indometacin farnesil, teprenone, and tocopherol nicotinate). The total daily drug dose administered in these formulations, which may range in complexity from simple solutions of the drug in a dietary oil up to multi-excipient, self-emulsifying drug delivery systems (SEDDS), may range from less than 0.25 μg to greater than 2000 mg. The amount of drug contained in a unit-dose capsule product may range from 0.25 μg to 500 mg and for oral solution products, from 1 μg/ml to 100 mg/ml. The total amount of lipid excipient administered in a single dose of a capsule formulation may range from 0.5 to 5 g, and can range from as low as 0.1 ml to as high as 20 ml for oral solution products. Some of these products tolerate room temperature storage for only brief periods of time and require long-term storage at 2-8° due to chemical and/or physical stability issues.

Preparation of Nanocrystals

| Ingredients | F1 | F2 | F3 |
| --- | --- | --- | --- |
| Drug 3HX | 8 gm | 8 gm | 8 gm |
| Polyox (w/w) | 0.5% | 1% | 1.5% |
| Piperine (w/w) | 2.5% | 5% | 10% |
| Tween 80 | 0.5% | 1% | 1.5% |
| Fulvic acid (w/w) | 2.5% | 5% | 10% |
| Poloxamer 188 (w/w) | 0.5% | 1% | 1.5% |

INCORPORATION BY REFERENCE

What follows is a cite list of references which are, in addition to those references cited above and below herein, and including that which is described as background, the invention summary, brief description of the drawings, the drawings and the abstract, hereby incorporated by reference into the detailed description of the preferred embodiments below, as disclosing alternative embodiments of elements or features of the preferred embodiments not otherwise set forth in detail below. A single one or a combination of two or more of these references may be consulted to obtain a variation of the preferred embodiments described in the detailed description below. Further patent, patent application and non-patent references are cited in the written description and are also incorporated by reference into the preferred embodiments.

A treatment regimen for psoriasis, eczema, inflammation, autoimmune disease, melanoma or other skin ailment, leukemia or other cancer, or other disease including methotrexate, betamethasone or another known treatment described herein, together with administering, before, during and/or after medicinal doses of such known treatment, combinations of the herbs and/or molecules described herein may also be combined with other treatments such as may be understood by those skilled in the art and/or as may be described in literature such as the following which are hereby incorporated by reference, along with the background and brief descriptions of the drawings and priority and related applications, as disclosing alternative embodiments and compounds that may be combined with an herbal and/or molecular combination and a known or discovered treatment or other described treatment in a cocktail or other combinative therapy:

U.S. Pat. Nos. 5,872,103; 6,197,754; 6,740,665; 6,812,255; 7,268,162; 7,358,222; 7,381,535; 7,393,656; 7,563,584; 7,695,926; 7,790,905; 8,541,382; 8,547,695; 8,734,859; and United States published patent applications serial nos. 20030211180; 20050008664; 20050026849; 20050196473; 20060205679; 20070191262; 20080152700; 20080220441; 20090018088; 20090143279; 20090215042; 20090269772; 20100068198; 20100092585; 20100144647; 20100167286; 20120122807; and PCT published applications no. WO01/66123A2; WO2004/052294A2; WO2006/053049A2; WO2007/130124A1; WO2012/063134A2.

Administration in a treatment regimen of certain combinations with one or two or more of these herbs serve to treat hair and scalp conditions as provided in accordance with embodiments described herein. Specific embodiments include advantageous combinations of Da Huang and Sheng Di Huang, as indicated below and in any one or a combination of US patent applications nos. 61/413,430; 62/325,993; 62/313,709; 62/268,226; 62/259,056; 62/348,762; 15/133,056; 15/131,743; 62/297,796; 62/198,637; 14/754,266; 14/710,865; 14/815,892; 14/287,158; 14/287,153; 13/890,990; 14/981,899; 14/815,705; 13/152,039; PCT/IB11/03078; PCT/IB13/02975; PCT/US15/38341; and US published patent applications nos. 20160051553; 20160136220; 20160136219; 20160136216; 20160136223; 20160136222; 20160136221; 20160113983; 20160143980; 20160113982; 20160136218; 20140205685; and 20140206631; and U.S. Pat. Nos. 9,066,974; 9,095,606; 8,734,859; 8,597,695; and 8,541,382; which are each incorporated by reference, as well as with combinations including Jin Yin Hua with Da Huang and/or Sheng Di Huang. Further embodiments include combinations of Da Huang, Sheng Di Huang and/or Jin Yin Hua, alone or in combination with 1-4 additional herbs, such as one or more of Mu Dan Pi, Di Gu Pi, Xian He Cao, and/or Chun Gen Pi.

Further embodiments include combinations of beta-sitosterol or saw palmetto, or both, with Da Huang, Sheng Di Huang and/or Jin Yin Hua, alone or with 1-4 other herbs, such as one or more of Mu Dan Pi, Di Gu Pi, Xian He Cao, and/or Chun Gen Pi and/or one or more other herbs or molecules described herein. Further embodiments include herbal combinations of one or more of Sheng Di Huang, Da Huang and Jin Yin Hua with combinations of one or more of emodin, digoxin, beta-sitosterol, saw palmetto, aucubin, rhein, rhapontin, vanillic acid, carvacrol or other herbs or molecules described herein or as understood by those skilled in the art.

Contained within any herb are several molecular constituents. Observed reductions of psoriatic inflammation and other studied effects owing to a treatment regimen of periodic shampooing with an herbal formula in accordance with the embodiments can be as a result of various combinations of active molecules contained in Da Huang, Jin Yin Hua and/or Sheng Di Huang, and of combinations of the herbs themselves.

It is contemplated, as people with ordinary skill in the art would do, that the newly separated compounds may be each individually or in combination used as an ingredient to prepare a pharmaceutical composition for a particular treatment purpose. As it is the status of the art in the pharmaceutical industry, once substantially pure preparations of a compound are obtained, various pharmaceutical compositions or formulations can be prepared from the substantially pure compound using conventional processes or future developed processes in the industry. Specific processes of making pharmaceutical formulations and dosage forms (including, but not limited to, tablet, capsule, injection, syrup) from chemical compounds are not part of the invention and people of ordinary skill in the art of the pharmaceutical industry are capable of applying one or more processes established in the industry to the practice of the present invention. Alternatively, people of ordinary skill in the art may modify the existing conventional processes to better suit the compounds of the present invention. For example, the patent or patent application databases provided at USPTO official website contain rich resources concerning making pharmaceutical formulations and products from effective chemical compounds. Another useful source of information is Handbook of Pharmaceutical Manufacturing Formulations, edited by Sarfaraz K. Niazi and sold by Culinary & Hospitality Industry Publications Services, which is incorporated by reference.

While the invention has been described in terms of several embodiments, those skilled in the art will recognize that the invention is not limited to the embodiments described, but can be practiced with modification and alteration within the spirit and scope of the appended claims. The description is thus to be regarded as illustrative instead of limiting of the invention as set forth in the appended claims including structural and functional equivalents thereof.

What is claimed is:

1. A medicinal composition formulated as a pill, skin patch, injection pen, subdermal injection packet, IV fluid package, tablet, capsule, lipid carrier, crystalline or other particulate formulation, subcutaneous insert, or stent, comprising
one or more effective doses each between 20-160 mg/kg of an active herbal component prepared by cooking a combination of effective amounts of Sheng Di Huang, Da Huang and Jin Yin Hua with an average particulate size that is less than 250 nm; and
piperine, fulvic acid, inulin or lysergol, or combinations thereof, as a bioavailability enhancer.

2. A shampoo, conditioner, lotion, gel, cream, ointment or other topical skin, scalp or hair treatment as in claim 1, further comprising:
an effective amount of Carbopol Ultraze 21, and
wherein said effective amount of Carbopol Ultraze 21 comprises between 1-5 wt./v %.

3. A medicinal composition as in claim 1, comprising lactose monohydrate as a diluent, polyvinyl povidone k-30 as a binder, magnesium stearate as a glidant, piperine, fulvic acid or inulin or combinations thereof, as a bioavailability enhancer and talc as a glidant.

4. A medicinal formulation, comprising shampoo, conditioner, lotion, gel, cream, lotion, ointment or other topical skin, scalp or hair treatment or a pill, skin patch, nano-gel, injection pen, subdermal injection packet, IV fluid package, tablet, capsule, nano lipid carrier, nano-crystal or other nano-particulate formulation, subcutaneous insert, or stent, or combinations thereof, said medicinal formulation comprising a predetermined number of one or more effective doses, each effective dose including between 20-160 mg/kg of an active herbal composition prepared by cooking a combination of effective amounts of Da Huang, Sheng Di Huang and Jin Yin Hua having average particulate sizes between 100-300 nm.

5. The medicinal formulation of claim 4, comprising 5% or more of propylene glycol.

6. The medicinal formulation of claim 4, comprising a cumulative drug release of more than 60%.

7. The medicinal formulation of claim 4, comprising a cumulative drug release of more than 70%.

8. The medicinal formulation of claim 4, comprising an extrudability of at least 1.5 grams/cm$^2$.

9. The medicinal formulation of claim 4, comprising a spreadability of at least 443 grams.

10. The medicinal formulation of claim 4, comprising a viscosity between 3000-5000 CP.

11. The medicinal formulation of claim 4, comprising an adhesiveness between 15-30 grams.

12. A medicinal formulation comprising shampoo, conditioner, lotion, gel, cream, lotion, ointment or other topical skin, scalp or hair treatment or a pill, skin patch, gel, injection pen, subdermal injection packet, IV fluid package, tablet, capsule, lipid carrier, nano-crystal or other nano-particulate formulation, subcutaneous insert, or stent, or combinations thereof, said medicinal formulation comprising a predetermined number of one or more effective doses, each effective dose including between 1.0 wt. %-15 wt. % of an active herbal composition prepared by cooking a combination of effective amounts of Da Huang, Sheng Di Huang and Jin Yin Hua having average particulate sizes between 100-300 nm.

13. The medicinal formulation of claim 12, comprising 5% or more propylene glycol.

14. The medicinal formulation of claim 12, comprising a cumulative drug release of more than 60%.

15. The medicinal formulation of claim 12, comprising a cumulative drug release of more than 80%.

16. The medicinal formulation of claim 12, comprising an extrudability of at least 1.5 grams/cm$^2$.

17. The medicinal formulation of claim 12, comprising a spreadability of at least 443 grams.

18. The medicinal formulation of claim 12, comprising a permeability that is higher by more than 20% compared with a formulation having an average particulate size above 400 nm.

19. The medicinal formulation of claim 12, comprising a viscosity between 3000-5000 CP.

20. The medicinal formulation of claim 12, comprising an adhesiveness between 15-30 grams.

* * * * *